(12) United States Patent
Horseman

(10) Patent No.: US 9,256,711 B2
(45) Date of Patent: Feb. 9, 2016

(54) SYSTEMS, COMPUTER MEDIUM AND COMPUTER-IMPLEMENTED METHODS FOR PROVIDING HEALTH INFORMATION TO EMPLOYEES VIA AUGMENTED REALITY DISPLAY

(75) Inventor: Samantha J. Horseman, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 161 days.

(21) Appl. No.: 13/540,335

(22) Filed: Jul. 2, 2012

(65) Prior Publication Data

US 2013/0009993 A1 Jan. 10, 2013

Related U.S. Application Data

(60) Provisional application No. 61/504,638, filed on Jul. 5, 2011, provisional application No. 61/659,831, filed on Jun. 14, 2012, provisional application No. 61/659,790, filed on Jun. 14, 2012, provisional application No.

(Continued)

(51) Int. Cl.
*G09G 5/00* (2006.01)
*G06F 19/00* (2011.01)

(52) U.S. Cl.
CPC ........ *G06F 19/3418* (2013.01); *G06F 19/3406* (2013.01)

(58) Field of Classification Search
CPC . G06F 19/3418; G06F 19/3406; G06F 3/011; G06F 21/32; G06F 19/3431; G02B 2027/0187; G02B 27/017; G02B 2027/0178; G02B 2027/014; G02B 27/0093; A61B 5/11; A61B 5/1112; A61B 5/4866; G06Q 20/40145; A63B 24/0062
USPC .......................................................... 345/633
See application file for complete search history.

(56) References Cited

U.S. PATENT DOCUMENTS 5,304,112 A 4/1994 Mrklas et al.
5,542,420 A 8/1996 Goldman et al.
(Continued)

FOREIGN PATENT DOCUMENTS

AU 767533 11/2003
CN 101065752 A 10/2007
(Continued)

OTHER PUBLICATIONS

Slater et al., Taking Steps: The Infulence of a Walking Technique on Presence in Virtual Reality, Sep. 1995, ACM Transactions on Computer-Human Interaction, vol. 2, No. 3, pp. 201-219.*

(Continued)

*Primary Examiner* — Kee M Tung
*Assistant Examiner* — Yuehan Wang
(74) *Attorney, Agent, or Firm* — Bracewell & Giuliani LLP; Constance G. Rhebergen; Christopher L. Drymalla

(57) ABSTRACT

Provided are embodiments of systems, computer medium and computer-implemented methods for providing feedback of health information to an employee when the employee is engaged in their work duties. The method including receiving health data output by a set of health sensors provided on or near the employee when the employee is engaged in work duties. The health sensors comprising at least one of biometric and biomechanic sensors. The health data corresponding to biometric and/or biomechanic characteristics sensed by the set of health sensors. The method including processing the health data to identify health status information for the employee, and providing for display via an augmented reality display, augmented reality content including the health status information. The augmented reality display providing the employee with an augmented reality view including a real world view of a surrounding environment having the health status information for the employee overlaid thereon.

20 Claims, 17 Drawing Sheets

Related U.S. Application Data

61/659,796, filed on Jun. 14, 2012, provisional application No. 61/659,800, filed on Jun. 14, 2012, provisional application No. 61/659,807, filed on Jun. 14, 2012, provisional application No. 61/659,810, filed on Jun. 14, 2012, provisional application No. 61/659,818, filed on Jun. 14, 2012, provisional application No. 61/659,824, filed on Jun. 14, 2012, provisional application No. 61/664,387, filed on Jun. 26, 2012, provisional application No. 61/664,399, filed on Jun. 26, 2012, provisional application No. 61/664,414, filed on Jun. 26, 2012.

(56) References Cited

U.S. PATENT DOCUMENTS

| | | |
|---|---|---|
| 5,570,301 A | 10/1996 | Barrus |
| 5,673,691 A | 10/1997 | Abrams et al. |
| 5,792,047 A | 8/1998 | Coggins |
| 5,937,387 A | 8/1999 | Summerell et al. |
| 6,033,344 A | 3/2000 | Trulaske et al. |
| 6,104,296 A | 8/2000 | Yasuchi et al. |
| 6,190,314 B1 | 2/2001 | Ark et al. |
| 6,281,594 B1 | 8/2001 | Sarich |
| 6,291,900 B1 | 9/2001 | Tiemann et al. |
| 6,293,771 B1 | 9/2001 | Haney et al. |
| 6,307,476 B1 | 10/2001 | Smith et al. |
| 6,309,342 B1 | 10/2001 | Blazey et al. |
| 6,334,837 B1 | 1/2002 | Hein et al. |
| 6,381,577 B1 | 4/2002 | Brown |
| 6,452,862 B1 | 9/2002 | Tomotani |
| 6,572,558 B2 | 6/2003 | Masakov et al. |
| 6,585,645 B2 | 7/2003 | Hutchinson |
| 6,646,556 B1 | 11/2003 | Smith et al. |
| 6,673,027 B2 | 1/2004 | Fischer |
| 6,768,246 B2 | 7/2004 | Pelrine et al. |
| 6,828,908 B2 | 12/2004 | Clark |
| 6,832,987 B2 | 12/2004 | David et al. |
| 6,982,497 B2 | 1/2006 | Rome |
| 7,005,757 B2 | 2/2006 | Pandian |
| 7,027,621 B1 | 4/2006 | Prokoski |
| 7,109,872 B2 | 9/2006 | Balaban et al. |
| 7,188,151 B2 | 3/2007 | Kumar et al. |
| 7,233,312 B2 | 6/2007 | Stern et al. |
| 7,304,580 B2 | 12/2007 | Sullivan et al. |
| 7,315,249 B2 | 1/2008 | Littell |
| 7,407,484 B2 | 8/2008 | Korman |
| 7,598,881 B2 | 10/2009 | Morgan |
| 7,624,037 B2 | 11/2009 | Bost |
| 7,652,582 B2 | 1/2010 | Littell |
| 7,689,271 B1 | 3/2010 | Sullivan |
| 7,771,318 B2 | 8/2010 | Narayanaswami |
| 7,849,115 B2 | 12/2010 | Reiner |
| 7,958,002 B2 | 6/2011 | Bost |
| 7,972,266 B2 | 7/2011 | Gobeyn et al. |
| 8,015,022 B2 | 9/2011 | Gore |
| 8,018,346 B2 | 9/2011 | Gottlieb et al. |
| 8,030,786 B2 | 10/2011 | Jackson et al. |
| 8,081,083 B2 | 12/2011 | Hinterlong |
| 8,095,641 B2 | 1/2012 | Aggarwal et al. |
| 8,203,454 B2 | 6/2012 | Knight et al. |
| 8,428,962 B1 | 4/2013 | Brinkley et al. |
| 8,487,456 B2 | 7/2013 | Donelan et al. |
| 8,636,670 B2 | 1/2014 | Ferren et al. |
| 2001/0039372 A1 | 11/2001 | Yasushi et al. |
| 2001/0041845 A1 | 11/2001 | Kim |
| 2002/0062069 A1 | 5/2002 | Mault |
| 2002/0077534 A1 | 6/2002 | DuRousseau |
| 2002/0095099 A1 | 7/2002 | Quyen et al. |
| 2002/0132092 A1 | 9/2002 | Wagner |
| 2002/0156351 A1 | 10/2002 | Sagel |
| 2002/0167486 A1 | 11/2002 | Tan et al. |
| 2002/0183644 A1 | 12/2002 | Levendowski et al. |
| 2002/0193707 A1 | 12/2002 | Atlas et al. |
| 2003/0058111 A1 | 3/2003 | Lee et al. |
| 2003/0154107 A1 | 8/2003 | Medvedeff |
| 2003/0209113 A1 | 11/2003 | Brooks et al. |
| 2003/0212579 A1 | 11/2003 | Brown et al. |
| 2003/0226695 A1 | 12/2003 | Mault |
| 2004/0002634 A1 | 1/2004 | Nihtila |
| 2004/0152956 A1 | 8/2004 | Korman |
| 2004/0162466 A1 | 8/2004 | Quy |
| 2004/0167381 A1 | 8/2004 | Lichter et al. |
| 2004/0193068 A1 | 9/2004 | Burton et al. |
| 2005/0075542 A1 | 4/2005 | Goldreich |
| 2005/0101845 A1 | 5/2005 | Nihtila |
| 2005/0273890 A1 | 12/2005 | Flaherty et al. |
| 2006/0026036 A1 | 2/2006 | Mahmood |
| 2006/0135857 A1 | 6/2006 | Ho et al. |
| 2006/0183980 A1 | 8/2006 | Yang |
| 2006/0267747 A1 | 11/2006 | Kondo |
| 2007/0017531 A1 | 1/2007 | Large |
| 2007/0038153 A1 | 2/2007 | Basson et al. |
| 2007/0050715 A1 | 3/2007 | Behar |
| 2007/0055549 A1 | 3/2007 | Moore et al. |
| 2007/0139362 A1 | 6/2007 | Colton et al. |
| 2007/0146131 A1 | 6/2007 | Boverie |
| 2007/0179360 A1 | 8/2007 | Mikat |
| 2007/0191727 A1 | 8/2007 | Fadem |
| 2007/0225585 A1 | 9/2007 | Washbon et al. |
| 2007/0276202 A1 | 11/2007 | Raisanen et al. |
| 2007/0299325 A1 | 12/2007 | Farrell et al. |
| 2008/0001736 A1 | 1/2008 | Steadman et al. |
| 2008/0015422 A1 | 1/2008 | Wessel |
| 2008/0052837 A1 | 3/2008 | Blumberg |
| 2008/0146892 A1 | 6/2008 | LeBoeuf et al. |
| 2008/0161654 A1 | 7/2008 | Teller et al. |
| 2008/0171914 A1 | 7/2008 | Ouwerkerk et al. |
| 2008/0177158 A1 | 7/2008 | Teller et al. |
| 2008/0177614 A1 | 7/2008 | An et al. |
| 2008/0177836 A1 | 7/2008 | Bennett |
| 2008/0194995 A1 | 8/2008 | Grady-Van Den Nieuwboer |
| 2008/0200774 A1 | 8/2008 | Luo |
| 2008/0218331 A1 | 9/2008 | Baillot |
| 2008/0242521 A1 | 10/2008 | Einav |
| 2008/0306357 A1 | 12/2008 | Korman |
| 2008/0306762 A1 | 12/2008 | James |
| 2009/0002178 A1 | 1/2009 | Guday et al. |
| 2009/0030767 A1 | 1/2009 | Morris et al. |
| 2009/0047645 A1 | 2/2009 | Dibenedetto et al. |
| 2009/0055204 A1 | 2/2009 | Pennington et al. |
| 2009/0058661 A1 | 3/2009 | Gleckler et al. |
| 2009/0160640 A1 | 6/2009 | Leung et al. |
| 2009/0198521 A1 | 8/2009 | Barker |
| 2009/0209829 A1 | 8/2009 | Yanagidaira et al. |
| 2009/0216558 A1 | 8/2009 | Reisman et al. |
| 2009/0287101 A1 | 11/2009 | Ferren et al. |
| 2009/0319297 A1 | 12/2009 | Hernandez et al. |
| 2010/0014711 A1 | 1/2010 | Camhi et al. |
| 2010/0049004 A1 | 2/2010 | Edman |
| 2010/0049541 A1 | 2/2010 | Pollard et al. |
| 2010/0169219 A1 | 7/2010 | Sellers et al. |
| 2010/0225489 A1 | 9/2010 | Hinterlong |
| 2010/0240458 A1 | 9/2010 | Gaiba et al. |
| 2010/0259043 A1 | 10/2010 | Balsamo |
| 2010/0283265 A1 | 11/2010 | Rastegar et al. |
| 2011/0033830 A1 | 2/2011 | Cherian |
| 2011/0035231 A1 | 2/2011 | Firminger et al. |
| 2011/0080290 A1 | 4/2011 | Baxi et al. |
| 2011/0098056 A1* | 4/2011 | Rhoads et al. ............. 455/456.1 |
| 2011/0137669 A1 | 6/2011 | Bennett |
| 2011/0152635 A1 | 6/2011 | Morris et al. |
| 2011/0172744 A1* | 7/2011 | Davis et al. .................... 607/62 |
| 2011/0196212 A1 | 8/2011 | Peters et al. |
| 2011/0213664 A1* | 9/2011 | Osterhout et al. ......... 705/14.58 |
| 2011/0285146 A1 | 11/2011 | Kozinsky et al. |
| 2012/0007367 A1 | 1/2012 | Chang |
| 2012/0010488 A1 | 1/2012 | Henry et al. |
| 2012/0052971 A1* | 3/2012 | Bentley ....................... 473/222 |
| 2012/0071731 A1 | 3/2012 | Gottesman |
| 2012/0086249 A1 | 4/2012 | Hotary et al. |
| 2012/0139731 A1* | 6/2012 | Razoumov et al. ......... 340/573.1 |
| 2012/0143031 A1 | 6/2012 | Belalcazar et al. |
| 2012/0146795 A1 | 6/2012 | Margon et al. |

(56) References Cited

U.S. PATENT DOCUMENTS

| | | |
|---|---|---|
| 2012/0154277 A1* | 6/2012 | Bar-Zeev et al. ............. 345/158 |
| 2012/0203491 A1 | 8/2012 | Sun et al. |
| 2012/0215076 A1 | 8/2012 | Yang et al. |
| 2012/0271121 A1 | 10/2012 | Della Torre et al. |
| 2013/0009761 A1 | 1/2013 | Horseman |
| 2013/0009993 A1 | 1/2013 | Horseman |
| 2013/0011819 A1 | 1/2013 | Horseman |
| 2013/0012786 A1 | 1/2013 | Horseman |
| 2013/0012787 A1 | 1/2013 | Horseman |
| 2013/0012788 A1 | 1/2013 | Horseman |
| 2013/0012789 A1 | 1/2013 | Horseman |
| 2013/0012790 A1 | 1/2013 | Horseman |
| 2013/0012802 A1 | 1/2013 | Horseman |
| 2013/0013327 A1 | 1/2013 | Horseman |
| 2013/0013331 A1 | 1/2013 | Horseman |
| 2013/0056981 A1 | 3/2013 | Mullins et al. |
| 2013/0297344 A1 | 11/2013 | Cosentino et al. |
| 2014/0172461 A1 | 6/2014 | Rogers |

FOREIGN PATENT DOCUMENTS

| | | |
|---|---|---|
| CN | 101115438 A | 1/2008 |
| CN | 201127606 Y | 10/2008 |
| DE | 102005048496 A1 | 4/2007 |
| EP | 1407713 | 9/2008 |
| EP | 2151355 | 2/2010 |
| EP | 2248461 A2 | 11/2010 |
| JP | 05-049603 A | 3/1993 |
| JP | 2000037357 A | 2/2000 |
| JP | 2001187030 A | 7/2001 |
| JP | 2001356849 A | 12/2001 |
| JP | 2002159052 A | 5/2002 |
| JP | 2003521972 A | 7/2003 |
| JP | 2003235813 A | 8/2003 |
| JP | 2005287688 A | 10/2005 |
| JP | 2008110032 A | 5/2008 |
| JP | 2009171544 A | 7/2009 |
| JP | 2009301360 A | 12/2009 |
| JP | 2010181324 A | 8/2010 |
| WO | 9601585 A1 | 1/1996 |
| WO | 0128416 | 4/2001 |
| WO | 0186403 | 11/2001 |
| WO | 2005064447 | 7/2005 |
| WO | 2006022465 A1 | 3/2006 |
| WO | 2007016056 A2 | 2/2007 |
| WO | 2007130591 A2 | 11/2007 |
| WO | 2010048145 | 4/2010 |
| WO | 2010051037 A1 | 5/2010 |
| WO | 2011020299 | 2/2011 |

OTHER PUBLICATIONS

Campbell et al., The Rise of People-Centric Sensing, Jul./Aug. 2008, IEEE Computer Society, 1089-7801/08, p. 12-21.*

International Search Report and Written Opinion for International Application No. PCT/US2012/045427, dated Dec. 3, 2012, pp. 1-14.

International Search Report and Written Opinion for International Application No. PCT/US2012/045419, dated Dec. 6, 2012, pp. 1-16.

International Search Report and Written Opinion for International Application No. PCT/US2012/045395, dated Dec. 3, 2012, pp. 1-16.

International Search Report and Written Opinion for International Application No. PCT/US2004/045442, dated Nov. 7, 2012, pp. 1-14.

International Search Report and Written Opinion for International Application No. PCT/US2012/045452, dated Dec. 3, 2012, pp. 1-14.

"Research programs—Philips Research", retrieved from <http://www.research.philips.com/programs/index.html>, May 7, 2012. (pp. 1-2).

"Speedy Assessment | Chiropractic Assessment and Patient Education", retrieved from <http://speedyassessment.com/>, May 7, 2012. (pp. 1-3).

"Stress Thermometer", retrieved from <http://www.biof.com/onlinestore/stressthermometer.asp?redirect=yes>, May 7, 2012. (pp. 1-4).

"Biofeedback—MayoClinic.com", retrieved from <http://www.mayoclinic.com/health/biofeedback/MY01072>, May 7, 2012. (pp. 1-2)

Abstract for "Psychosocial job factors and symptoms from the locomotor system—a multicasual analysis", retrieved from <http://www.ncbi.nlm.nih.gov/pubmed/1962160>, May 7, 2012. (p. 1).

Abstract for "Signal Characteristics of EMG at Different Levels of Muscle Tension", retrieved from <http://onlinelibrary.wiley.com/doi/10.1111/j.1748-1716.1976.tb10195.x/abstract>, May 7, 2012. (p. 1).

Index for "Micro-NanoMechatronics and Human Science (MHS), 2010 International Symposium Nov. 2010", retrieved from <http://ieeexplore.ieee.org/xpl/mostRecentIssue.jsp?punumber=5658189> Ma 7, 2012, (pp. 1-5).

"Wireless measurement devices—Philips", retreved from <http://www.healthcare.philips.com/us_en/products/telehealth/Products/devices.wpd>, May 7, 2012. (pp. 1-2).

"Philips Research Technology Backgrounder—MyHeart project", retrieved from <http://www.research.philips.com/technologies/heartcycle/myheart-gen.html>, May 7, 2012. (pp. 1-3).

"SmartHeart SE102 Heart Rate Monitor", retrieved from <http://us.oregonscientific.com/cat-Sports-and-Health-sub-Heart-Rate-Monitors-prod-SmartHeart-SE102-Heart-Rate-Monitor.html>, May 7, 2012. (pp. 1-4).

"Philips Research—Download Pictures", retrieved from <http://www.research.philips.com/downloads/pictures/healthcare-personal.html>, May 7, 2012. (pp. 1-2).

"RJL Systems, Products", retrieved from <http://www.rjlsystems.com/products.shtml>, May 7, 2012. (p. 1).

"MomToBe: The Pregnancy Assistant 3.0", retreved from <http://3d2f.com/programs/4-230-momtobe-the-pregnancy-assistant-download.shtml>, Jun. 11, 2012. (pp. 1-2).

"Clever toilet checks on your health", retrieved from <http://articles.cnn.com/2005-06-28/tech/spark.toilet_1_toilet-toto-bathroom?_s=PM:TECH>, Jun. 28, 2005. (pp. 1-2).

"WorkPace : RSI Injury Prevention Software, Stretch Break Exercise Reminder Software", retrieved from <http://www.workpace.com/>, Sep. 14, 2012. (p. 1).

"Workrave", retrieved from <http://www.workrave.org/>, Sep. 14, 2012. (p. 1).

"Office Athlete Software Prevents Common Repetitive Stress Injuries", retrieved from <http://www.officeathlete.com/>, Sep. 14, 2012. (pp. 1-2).

"Cardinus Risk Management | Ergonomic & DSE Risk Assessments", retrieved from <http://www.cardinus.com/>, Sep. 12, 2012. (pp. 1-2).

"Kinect—Xbox.com", retrieved from <http://www.xbox.com/en-US/kinect>, Jun. 11, 2012. (pp. 1-3).

"Augmented Reality", retrieved from <http://en.wikipedia.org/wiki/Augmented_reality>, May 30, 2012. pp. 1-18.

"Electroencephalography (EEG)", retieved from <http://www.emedicinehealth.com/script/main/art.asp?articlekey-59319&pf=3&page=1>, Jun. 11, 2012. (pp. 1-4).

"Emotiv|EEG System|Electroencephalography", retrieved from <www.emotiv.com/index.asp>, Jun. 11, 2012. (pp. 1-2).

"EmotivEPOC Software Devlopment Kit", retrieved from <www.emotiv.com/store/hardware/epoc-bci-eeg/developer-neuroheadset/>, Jun. 11, 2012. (pp. 1-2).

Chapman, Larry S. MPH, "Meta-evaluation of Worksite Health Promotion Economic Return Studies: 2005 Update", Jul./Aug. 2005. (pp. 1-11).

"OSHA Ergonomic Solutions: Computer Workstations eTool—Checklists", retrieved from <www.osha.gov/SLTC/etools/computerworkstations/checklist.html>, Jun. 11, 2012. (pp. 1-5).

"OSHA Ergonomic Solutions: Computer Workstations eTool—Good Working Positions", retrieved from <www.osha.gov/SLTC/etools/computerworkstations/positions.html>, Jun. 11, 2012. (pp. 1-2).

"OSHA Ergonomic Solutions: Computer Workstations eTool—Work Process and Recognition", retrieved from <www.osha.gov/SLTC/etools/computerworkstations/workprocess.html>, Jun. 11, 2012. (pp. 1-2).

(56) References Cited

OTHER PUBLICATIONS

"OSHA Ergonomic Solutions: Computer Workstations eTool—Workstation Environment", retrieved from <www.osha.gov/SLTC/etools/computerworkstations/wkstation_enviro.html>, Jun. 11, 2012. (pp. 1-3).

"OSHA Ergonomic Solutions: Computer Workstations eTool—Workstations eTool", retrieved from <www.osha.gov/SLTC/etools/computerworkstations/index.html>, Jun. 11, 2012. (p. 1).

"The Wellness Imperative, Creating More Effective Organizations", World Economic Forum, 2010. (pp. 1-20).

Berry, Leonard et al., "What's the Hard Return on Employee Wellness Programs?", Harvard Business Review, Dec. 2010. (pp. 1-10).

"www.mydailyhealth.com" retrieved from the "wayback machine" (pp. 1-20).

Health/Medical Writers eHealthcareWorld 2000. (May 1). MyDailyHealth.com (pp. 1-3).

Murray Hill, Well Med Team to Offer Next Generation Online Preventive Health Services. (Nov. 3). PR Newswire, 1. (pp. 1-3).

Copending U.S. Appl. No. 14/035,670 titled "Computer Mouse for Monitoring and Improving Health and Productivity of Employees", filed Sep. 24, 2013.

Copending U.S. Appl. No. 14/035,717 titled "Computer Mouse System and Associated Computer Medium for Monitoring and Improving Health and Productivity of Employees", filed Sep. 24, 2013.

Copending U.S. Appl. No. 14/035,732 titled "Methods for Monitoring and Improving Health and Productivity of Employees Using a Computer Mouse System", filed Sep. 24, 2013.

Copending U.S. Appl. No. 14/043,898 titled "Systems, Computer Medium and Computer-Implemented Methods for Quantifying and Employing Impacts of Workplace Wellness Programs", filed Oct. 2, 2013.

USPTO Communicaiton for U.S. Appl. No. 13/540,067 mailed Oct. 17, 2013. (pp. 1-39).

"Making a Difference", World Health Organisation, Geneva: WHO, 1999, pp. 1-136.

"National health expenditure data", Centers for Medicare & Medicaid Services, available at: <http://www.cms.gov/Research-Statistics-Data-and-Systems/Statistics-Trends-and-Reports>, accessed Nov. 18, 2013, pp. 1-2.

"Piezo Electric Energy Harvester", Midé Technology Corporation, retrieved Nov. 18, 2013. pp. 1-2.

"Signal Conditioning Piezoelectric Sensors", (PDF) Texas Instruments, Application Report SLOA033A, Sep. 2000, pp. 1-6.

The constitution of the World Health Organization, World Health Organization, WHO Chronicle, 1947, pp. 1-202.

Aldana, S., "Financial Impact of health promotion programs: a comprehensive review of the literature", American Journal of Health Promotion,155, 2001, pp. 296-320.

Aldana, S., Merrill, R., Price, K., Hardy, A., and Hager, R., "Financial impact of a comprehensive multi-site worksite health promotion program", Preventive Medicine, 40, Jul. 2004, pp. 131-137.

Alfredo Vázquez Carazo, "Novel Piezoelectric Transducers for High Voltage Measurements", Jan. 2000 , pp. 1-277.

Baiker, K., Cutler, D., Song, Z., "Worksite wellness programs can generate savings", Health Affairs 29(2), Jan. 2010, pp. 1-8.

Berry, L.L., Mirabito, A.M., Baun, W.B., "What's the Hard Return on Employee Wellness Programs?", Harvard Business Review, Dec. 2010, pp. 1-10.

Chapman, L., "Expert opinions on 'best practice' in worksite health promotion (WHP)", Jul./Aug. 2004, pp. 1-13.

Chapman, L.. "Meta-evaluation of worksite health promotion economic return studies: 2012 Update", Mar./Apr. 2012, pp. 1-13.

Edington, D. W., "Emerging research: a view from one research centre", American Journal of Health Promotion, 15(5), May/Jun. 2001, pp. 341-349.

Edington, M., Karjalainen, T., Hirschland, D., Edington, D.W., "The UAW-GM Health Promotion Program: Successful Outcomes", American Association of Occupational Health Nursing Journal.50, Jan. 2002, pp. 26-31.

Hemp, P., "Presenteeism: At Work—But Out of It", Harvard Business Review, Oct. 2004, pp. 49-58.

Horseman, S. J ., "Healthy Human Capital as a Business Strategy: The Saudi Aramco Wellness Program (SAWP)", American Society of Safety Engineers (ME Chapter), (9) Conference Proceedings. Bahrain. Feb. 2010, pp. 178-185.

Horseman, S.J., "ErgoWELL : An Integrative Strategy", SPE Paper #: SPE-152629. Society of Petroleum Engineers, MEHSSE. Paper and Workshop, Abu Dhabi, 2012, pp. 1-17.

Johns, G., "Presenteeism in the Workplace: A review and research agenda", Journal of Organizational Behavior, 31, Jul. 2009, pp. 519-542.

Priya, S., "Advances in Energy Harvesting Using Low Profile Piezoelectric Transducers", Materials Science & Engineering, Springer, Mar. 2007, pp. 165-182.

Reidel, J.E., Baase, C., "The effect of disease prevention & health promotion on worksite productivity: a literature review", American Journal of Health Promotion, 15:3, Jan./Feb. 2001, pp. 167-191, 243.

Roberts, R.O.,Bergstralh, E.J., Schmidt, L., Jacobsoen,S.J., "Comparison of Self Reported and Medical Record Health Care Utilization Measures", Journal of Clinical Epidemiology, 49:9, Feb. 1996, pp. 989-995.

Copending U.S. Appl. No. 14/102,619 titled "Systems, Computer Medium and Computer-Implemented Methods for Harvesting Human Energy in the Workplace", filed Dec. 11, 2013.

Copending U.S. Appl. No. 14/180,529 titled "Chair Pad System and Associated, Computer Medium and Computer-Implemented Methods for Monitoring and Improving Health and Productivity of Employees" filed Feb. 14, 2014.

Copending U.S. Appl. No. 14/180,533 titled "Chair Pad System and Associated, Computer Medium and Computer-Implemented Methods for Monitoring and Improving Health and Productivity of Employees" filed Feb. 14, 2014.

Copending U.S. Appl. No. 14/180,536 titled "Floor Mat System and Associated, Computer Medium and Computer-Implemented Methods for Monitoring and Improving Health and Productivity of Employees" filed Feb. 14, 2014.

Copending U.S. Appl. No. 14/180,471 titled "Floor Mat System and Associated, Computer Medium and Computer-Implemented Methods for Monitoring and Improving Health and Productivity of Employees" filed Feb. 14, 2014.

Copending U.S. Appl. No. 14/180,993 titled "Systems, Computer Medium and Computer-Implemented Methods for Monitoring and Improving Biometric Health of Employees" filed Feb. 14, 2014.

Copending U.S. Appl. No. 14/181,006 titled "Systems, Computer Medium and Computer-Implemented Methods for Monitoring and Improving Biomechanical Health of Employees" filed Feb. 14, 2014.

Copending U.S. Appl. No. 14/180,978 titled "Systems, Computer Medium and Computer-Implemented Methods for Monitoring and Improving Health and Productivity of Employees" filed Feb. 14, 2014.

International Preliminary Report on Patentability for International Application No. PCT/US2012/045395, dated Jan. 7, 2014. (pp. 1-12).

International Preliminary Report on Patentability for International Application No. PCT/US2012/045401, dated Jan. 7, 2014. (pp. 1-9).

International Preliminary Report on Patentability for International Application No. PCT/US2012/045407, dated Jan. 7, 2014. (pp. 1-8).

International Preliminary Report on Patentability for International Application No. PCT/US2012/045410, dated Jan. 7, 2014. (pp. 1-8).

International Preliminary Report on Patentability for International Application No. PCT/US2012/045414, dated Jan. 7, 2014. (pp. 1-8).

International Preliminary Report on Patentability for International Application No. PCT/US2012/045419, dated Jan. 7, 2014. (pp. 1-11).

International Preliminary Report on Patentability for International Application No. PCT/US2012/045427, dated Jan. 7, 2014. (pp. 1-10).

International Preliminary Report on Patentability for International Application No. PCT/US2012/045435, dated Jan. 7, 2014. (pp. 1-10).

International Preliminary Report on Patentability for International Application No. PCT/US2012/045452, dated Jan. 7, 2014. (pp. 1-9).

(56) References Cited

OTHER PUBLICATIONS

International Preliminary Report on Patentability for International Application No. PCT/US2012/045447, dated Jan. 7, 2014. (pp. 1-8).
International Preliminary Report on Patentability for International Application No. PCT/US2012/045442, dated Jan. 7, 2014. (pp. 1-10).
Centers for Disease Control and Prevention, 2011, "Chronic diseases and health promotion", [online] Availableat: http://www.cdc.gov/chronicdisease/ overview, [Accessed Feb. 2, 2011].
"Pulse Oximetry" SparkFun Electronics, Oct. 7, 2005. (p. 1).
International Search Report & Written Opinion for International Application No. PCT/US2012/045447, dated Jan. 18, 2013. (pp. 1-12).
International Search Report & Written Opinion for International Application No. PCT/US2012/045407, dated Jan. 23, 2013. (pp. 1-15).
International Search Report & Written Opinion for International Application No. PCT/US2012/045401, dated Feb. 5, 2013. (pp. 1-13).
International Search Report & Written Opinion for International Application No. PCT/US2012/045435, dated Jan. 25, 2013. (pp. 1-14).
International Search Report & Written Opinion for International Application No. PCT/US2012/045410, dated Jan. 31, 2013. (pp. 1-13).
International Search Report & Written Opinion for International Application No. PCT/US2012/045414, dated Mar. 25, 2013. (pp. 1-13).
Copending U.S. Appl. No. 13/540,028 titled "Systems, Computer Medium and Computer-Implemented Methods for Monitoring and Improving Cognitive and Emotive Health of Employees", filed Jul. 2, 2012.
Copending U.S. Appl. No. 13/540,067 titled "Computer Mouse System and Associated, Computer Medium and Computer-Implemented Methods for Monitoring and Improving Health and Productivity of Employees", filed Jul. 2, 2012.
Copending U.S. Appl. No. 13/540,095 titled "Chair Pad System and Associated, Computer Medium and Computer-Implemented Methods for Monitoring and Improving Health and Productivity of Employees", filed Jul. 2, 2012.
Copending U.S. Appl. No. 13/540,124 titled "Floor Mat System and Associated, Computer Medium and Computer-Implemented Methods for Monitoring and Improving Health and Productivity of Employees", filed Jul. 2, 2012.
Copending U.S. Appl. No. 13/540,153 titled "Systems, Computer Medium and Computer-Implemented Methods for Monitoring and Improving Biometric Health of Employees", filed Jul. 2, 2012.
Copending U.S. Appl. No. 13/540,180 titled "Systems, Computer Medium and Computer-Implemented Methods for Monitoring and Improving Biomechanical Health of Employees", filed Jul. 2, 2012.
Copending U.S. Appl. No. 13/540,208 titled "Systems, Computer Medium and Computer-Implemented Methods for Coaching Employees Based Upon Monitored Health Conditions Using an Avatar", filed Jul. 2, 2012.
Copending U.S. Appl. No. 13/540,300 titled "Systems, Computer Medium and Computer-Implemented Methods for Monitoring Health of Employees Using Mobile Devices", filed Jul. 2, 2012.
Copending U.S. Appl. No. 13/540,374 titled "Systems, Computer Medium and Computer-Implemented Methods for Monitoring Health and Ergonomic Status of Drivers of Vehicles", filed Jul. 2, 2012.
Copending U.S. Appl. No. 13/540,262 titled "Systems, Computer Medium and Computer-Implemented Methods for Monitoring and Improving Health and Productivity of Employees", filed Jul. 2, 2012.
Bed-Check Co., Bed-Check Monitoring Systems, 2006.
Final Office Action for co-pending U.S. Appl. No. 13/540,067 dated Jun. 3, 2014.
Office Action for co-pending U.S. Appl. No. 13/540,095 dated May 22, 2014.
Office Action for co-pending U.S. Appl. No. 13/540,124 dated Jul. 3, 2014.
Office Action for co-pending U.S. Appl. No. 13/540,208 dated Jun. 20, 2014.
The American Heritage Dictionary of the English Language, definition of planar, 2000.
"Footrests—Adjustable Footrest Solutions for the Office", Ergo in Demand, Aug. 20, 2009, pp. 1-4, Ergo In Demand Inc., www.ergoindemand.com/footrest.html.
Berger et al., "Investing in Healthy Human Capital", Journal of Occupational Environmental Medicine vol. 45, No. 12, dated Dec. 2003; pp. 1213-1225.
Brown et al., "Prowess Proactive Wellness Environment Support System", Dec. 10, 2009, pp. 1-19, www.hsi.gatech.edu/onsitecenter/index.php/PROWESS.
Campbell et al., "The Rise of People-Centric Sensing", IEEE Computer Society, 2008, pp. 12-21, IEEE.
Georgia Tech, "Prowess Proactive Wellness Environment Support System", Dec. 12, 2009, pp. 1-27, www.hsi.gatech.edu/onsitecenter/index.php/PROWESS.
Goetzel et al., "Estimating the Return-on-Investment From Changes in Employee Health Risks on The Dow Chemical Company's Health Care Costs", Journal of Occupational Environmental Medicine vol. 47, No. 8, dated Aug. 2005; pp. 759-768.
Goetzel et al., "Health, Absence, Disability, and Presenteeism Cost Estimates of Certain Physical and Mental Health Conditions Affecting U.S. Employers", Journal of Occupational Environmental Medicine vol. 46, No. 4, dated Apr. 2004; pp. 398-412.
Goetzel et al., "Second-Year Results of an Obesity Prevention Program at The Dow Chemical Company", Journal of Occupational Environmental Medicine vol. 52, No. 3, dated Mar. 2010; pp. 291-302.
Goetzel et al., "The Health and Productivity Cost Burden of the "Top 10" Physical and Mental Health Conditions Affecting Six Large U.S. Employers in 1999", Journal of Occupational Environmental Medicine vol. 45, No. 1, dated Jan. 2003; pp. 5-14.
Goetzel et al., "The Long-Term Impact of Johnson & Johnson's Health & Wellness Program on Employee Health Risks", Journal of Occupational Environmental Medicine vol. 44, No. 5, dated May 2002; pp. 417-424.
Goetzel et al., "The Relationship Between Modifiable Health Risks and Health Care Expenditures: An Analysis of the Multi-Employer HERO Health Risk and Cost Database", Journal of Occupational Environmental Medicine, vol. 40, No. 10; pp. 1-30.
Goetzel et al., "The Workforce Wellness Index", Journal of Occupational Environmental Medicine vol. 55, No. 3, dated Mar. 2013; pp. 272-279.
Goetzel et al., "The Predictive Validity of the HERO Scorecard in Determining Future Health Care Cost and Risk Trends", Journal of Occupational Environmental Medicine vol. 56, No. 2, dated Feb. 2014; pp. 136-144.
Kelly et al., "The Novartis Health Index: A Method for Valuing the Economic Impact of Risk Reduction in a Workforce" Journal of Occupational Environmental Medicine vol. 52, No. 5, dated May 2010; pp. 528-535.
Prochaska et al., "The Well-Being Assessment for Productivity", Journal of Occupational Environmental Medicine vol. 53, No. 7, dated Jul. 2011; pp. 735-768.
Slater et al., "Taking Steps: The Influence of a Walking Technique on Presence in Virtual Reality", ACM Transactions on Computer-Human Interaction, Sep. 1995, pp. 201-219, vol. 2 No. 3.
Sullivan, "Making the Business Case for Health and Productivity Management", Journal of Occupational Environmental Medicine vol. 46, No. 6 suppl, dated Jun. 2004; pp. S56-S61.
World Economic Forum, "The Workplace Wellness Alliance-Making the Right Investment: Employee Health and the Power of Metrics" dated Jan. 2013; pp. 1-36.
USPTO Communication for U.S. Appl. No. 13/540,262, mailed Apr. 9, 2014. (pp. 1-56).
USPTO Communication for U.S. Appl. No. 13/540,153, mailed Apr. 9, 2014. (pp. 1-50).
USPTO Communication for U.S. Appl. No. 13/540,180, mailed Apr. 9, 2014. (pp. 1-49).

(56) References Cited

OTHER PUBLICATIONS

USPTO Communication for U.S. Appl. No. 13/540,335, mailed Apr. 25, 2014. (pp. 1-48).
Final Office Action for co-pending U.S. Appl. No. 13/540,095 dated Jan. 16, 2015.
Final Office Action for co-pending U.S. Appl. No. 13/540,153 dated Jan. 23, 2015.
Final Office Action for co-pending U.S. Appl. No. 13/540,180 dated Jan. 23, 2015.
Final Office Action for co-pending U.S. Appl. No. 13/540,262 dated Jan. 22, 2015.
Office Action for co-pending U.S. Appl. No. 13/540,028 dated Mar. 5, 2015.
Office Action for co-pending U.S. Appl. No. 13/540,300 dated Feb. 12, 2015.
Nintendo Wii Fit, https://www.youtube.com/watch?v=-Taruqvk30E, May 11, 2008.
"Statement in accordance with the Notice from the European Patent Office dated Oct. 1, 2007 concerning business methods" Nov. 1, 2007, 1 page, XP002456414.
EPO: "Notice from the European Patent Office dated Oct. 1, 2007 concerning business methods" Official Journal EPO, vol. 30, No. 11, Nov. 1, 2007, pp. 592-593, XP007905525.
Kymissis et al. "Parasitic Power Harvesting in Shoes" Digest of Papers, Second International Symposium on Wearable Computers, Pittsburgh, PA, Oct. 19-20, 1998, pp. 132-139, XP032385438.

* cited by examiner

US 9,256,711 B2

SYSTEMS, COMPUTER MEDIUM AND COMPUTER-IMPLEMENTED METHODS FOR PROVIDING HEALTH INFORMATION TO EMPLOYEES VIA AUGMENTED REALITY DISPLAY

RELATED APPLICATIONS

This application claims the benefit of U.S. Provisional Patent Application No. 61/664,399 filed on Jun. 26, 2012 and titled "SYSTEMS, COMPUTER MEDIUM AND COMPUTER-IMPLEMENTED METHODS FOR PROVIDING HEALTH INFORMATION TO EMPLOYEES VIA AUGMENTED REALITY DISPLAY", U.S. Provisional Patent Application No. 61/504,638 filed on Jul. 5, 2011 and titled "SYSTEM, COMPUTER PROGRAM PRODUCT AND COMPUTER-IMPLEMENTED METHOD FOR IMPROVING AND MONITORING THE HEALTH AND PRODUCTIVITY OF EMPLOYEES", U.S. Provisional Patent Application No. 61/659,831 filed on Jun. 14, 2012 and titled "SYSTEMS, COMPUTER MEDIUM AND COMPUTER-IMPLEMENTED METHODS FOR MONITORING AND IMPROVING HEALTH AND PRODUCTIVITY OF EMPLOYEES", U.S. Provisional Patent Application No. 61/659,790 filed on Jun. 14, 2012 and titled "SYSTEMS, COMPUTER MEDIUM AND COMPUTER-IMPLEMENTED METHODS FOR MONITORING AND IMPROVING COGNITIVE AND EMOTIVE HEALTH OF EMPLOYEES", U.S. Provisional Patent Application No. 61/659,796 filed on Jun. 14, 2012 and titled "COMPUTER MOUSE SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", U.S. Provisional Patent Application No. 61/659,800 filed on Jun. 14, 2012 and titled "CHAIR PAD SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", U.S. Provisional Patent Application No. 61/659,807 filed on Jun. 14, 2012 and titled "FLOOR MAT SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", U.S. Provisional Patent Application No. 61/659,810 filed on Jun. 14, 2012 and titled "SYSTEMS, COMPUTER MEDIUM AND COMPUTER-IMPLEMENTED METHODS FOR MONITORING AND IMPROVING BIOMETRIC HEALTH OF EMPLOYEES", U.S. Provisional Patent Application No. 61/659,818 filed on Jun. 14, 2012 and titled "SYSTEMS, COMPUTER MEDIUM AND COMPUTER-IMPLEMENTED METHODS FOR MONITORING AND IMPROVING BIOMECHANICAL HEALTH OF EMPLOYEES", U.S. Provisional Patent Application No. 61/659,824 filed on Jun. 14, 2012 and titled "SYSTEMS, COMPUTER MEDIUM AND COMPUTER-IMPLEMENTED METHODS FOR COACHING EMPLOYEES BASED UPON MONITORED HEALTH CONDITIONS USING AN AVATAR", U.S. Provisional Patent Application No. 61/664,387 filed on Jun. 26, 2012 and titled "SYSTEMS, COMPUTER MEDIUM AND COMPUTER-IMPLEMENTED METHODS FOR MONITORING HEALTH OF EMPLOYEES USING MOBILE DEVICES", and U.S. Provisional Patent Application No. 61/664,414 filed on Jun. 26, 2012 and titled "SYSTEMS, COMPUTER MEDIUM AND COMPUTER-IMPLEMENTED METHODS FOR MONITORING HEALTH AND ERGONOMIC STATUS OF DRIVERS OF VEHICLES", the disclosures of which are each hereby incorporated by reference in their entireties.

FIELD OF INVENTION

The present invention relates generally to health monitoring and more particularly to systems, machines, non-transitory computer medium having computer program instructions stored thereon, and computer-implemented methods for providing health information to employees.

BACKGROUND OF THE INVENTION

A major concern among employers is the issue of presenteeism, or the phenomena that, while employees may be at work, health problems such as, lower back pain, fatigue, high blood pressure and obesity, keep them from working optimally, and cause a rapid rise in employee healthcare costs. Unfortunately, even if employees are made aware of sound health and ergonomic practices, they often slip back into poor health and ergonomic practices while engrossed in work. For example, although the employee may know they need to avoid lifting a heavy objects to reduce the risk of a back injury (e.g., based on an annual health awareness presentation), the employee may simply forget while they are engrossed in their daily work activities and lift a heavy object.

The current state of the art solution is to notify an employee of health conditions and poor ergonomics based on workplace health programs that require the employee to actively participate the in periodic health tests. For example, health programs may monitor the employee using health tests that are conducted at discrete testing times (e.g., quarterly or annual health tests) and, only then, provide the employee with test results. Thus, existing health programs may require the employee to expend effort just to take part in the program, decreasing the likelihood the employee will even engage the health program, much less continue the health program for an extended period of time. Moreover, the infrequent nature of the health tests may provide results that are based on a few discrete time periods throughout the year and, thus, are not capable of providing frequent (e.g., real-time) feedback that can be used by the employee to dynamically adjusted their day-to-day actions. As a result, employees may not be aware of the health consequences that result from their actions during the work day and, even when the employees are aware of the consequences of their actions (e.g., based on quarterly or annual health tests), the employees may simply forget to follow good health practices while they are engrossed in work and are not focused on the impact of their actions on their health.

SUMMARY OF THE INVENTION

Applicant has recognized several shortcomings associated with existing health programs, and, in view of these shortcomings, has recognized the need for a health monitoring system that enables health data to be collected from employees in their work environment while also providing feedback that can aid the employee in accomplishing their work duties in a safe and healthy manner. Applicant has recognized that traditional health programs and related testing systems may only provide a snap-shot of the employee's health at a time of testing, but may not be capable of taking into account dynamic changes in the employee's health while they are working in their day-to-day work environment. Thus, traditional health systems are unable to provide real-time feedback to the employee that can be used by the employee to make informed decisions regarding their actions throughout the work day. For example, traditional health system do not provide employees with a real-time summary of their current health status, inform the employee regarding the consequences of their actions immediately after the employee engages in the actions (or even before the employee engage in the actions), or provide suggestions to improve the employee's health based on their current situation. As a result of employees being uniformed about the health consequences of their actions, the employees may engage in activities that are detrimental to their health. In view of the foregoing, various embodiments of the present invention advantageously provide systems, machines, non-transitory computer medium having computer program instructions stored thereon, and computer-implemented methods for monitoring the health of employees in their work environment and providing real-time feedback to the employee via an augmented reality display.

In some embodiments, provided is a system for providing real-time feedback of health information to an employee when the employee is engaged in their work duties. The system including a set of one or more health sensors configured to be provided on or near the employee when the employee is engaged in work duties. The one or more health sensors including at least one of biometric sensors configured to sense biometric characteristics of the employee and biomechanic sensors configured to sense biomechanic characteristics of the employee. The one or more health sensors configured to output health data corresponding to at least one of the biometric characteristics and biomechanic characteristics sensed by the set of one or more health sensors. The system also including an augmented reality display device configured to provide the employee with an augmented reality view including a real world view of a surrounding environment and health status information for the employee overlaid on the real world view of the surrounding environment. The system also including health server configured to receive, via a communications network, the health data output by the set of one or more health sensors, process the health data received to identify the health status information for the employee, and serve, via the communications network for display via the augmented reality display device, augmented reality content that includes the health status information for the employee to be overlaid on the real world view of the surrounding environment such that the employee is provided with an augmented reality view including the real world view of the surrounding environment having an overlay of the health status information for the employee based at least in part on the health data collected via the set of one or more health sensors configured to be provided on or near the employee when the employee is engaged in work duties.

In certain embodiments the system includes a mobile communications device configured to collect the health data from the set of one or more health sensors, forward the health data to the health server, receive the augmented reality content from the server, and provide the augmented reality content to the augmented reality display device for display to the employee.

In some embodiments, provided is a system for providing feedback of health information to an employee when the employee is engaged in their work duties. The system including a set of one or more health sensors configured to be provided on or near the employee when the employee is engaged in their work duties. The one or more health sensors including at least one of biometric sensors configured to sense biometric characteristics of the employee and biomechanic sensors configured to sense biomechanic characteristics of the employee. The one or more health sensors configured to output health data corresponding to at least one of biometric characteristics and biomechanic characteristics sensed by the set of one or more health sensor. The system also including an augmented reality display configured to provide the employee with an augmented reality view including a real world view of a surrounding environment and health status information for the employee overlaid on the real world view of the surrounding environment. The system also including an augmented reality processor configured to receive the health data output by the one or more health sensors, process the health data received to identify the health status information for the employee, and provide, for display via the augmented reality display, augmented reality content including the health status information such that the employee is provided with an augmented reality view including the real world view of the surrounding environment having an overlay of the health status information for the employee based at least in part on the health data collected via the set of one or more health sensors configured to be provided on or near the employee when the employee is engaged in work duties.

In certain embodiments, processing the health data received to identify the health status information for the employee includes processing the health data to determine a health characteristic for the employee, and wherein the augmented reality content includes the health characteristic for the employee such that the employee is provided with an augmented reality view including the real world view of the surrounding environment having an overlay of the health characteristic for the employee.

In some embodiments, processing the health data received to identify the health status information for the employee includes identifying an action taken by the employee, and determining a predicted consequence based at least in part on the action taken by the employee. The augmented reality content including the predicted consequence such that the employee is provided with an augmented reality view including the real world view of the surrounding environment having an overlay of the predicted consequence based at least in part on an action taken by the employee.

In certain embodiments, the predicted consequence includes a consequence to the employee's physical health or mental health.

In some embodiments, processing the health data received to identify the health status information for the employee includes processing the health data to predict an action to be taken by the employee and determining a predicted consequence based at least in part on the predicted action to be taken by the employee. The augmented reality content including the predicted consequence such that the employee is provided with an augmented reality view including the real world view of the surrounding environment including an overlay of the predicted consequence based at least in part on the predicted action to be taken by the employee, wherein the predicted consequence is configured to be displayed to the employee prior to the employee actually taking the predicted action.

In certain embodiments, at least one of the health sensors includes a neural sensor configured to sense brain activity of the employee, and processing the health data to predict an action to be taken by the employee includes predicting the action based at least in part on the brain activity of the employee.

In some embodiments, the augmented reality display includes a head-up display configured to be viewable by the employee when the employee is engaged in work duties.

In certain embodiments, the augmented reality display includes a head-up display provided in a safety helmet worn by the employee and configured to be viewable by the employee when the employee is engaged in work duties.

In some embodiments, the augmented reality display includes a head-up display provided in eyewear worn by the employee and configured to be viewable by the employee when the employee is engaged in work duties.

In certain embodiments, the set of one or more health sensors includes at least one of at least one of a temperature sensor configured to output temperature data indicative of a body temperature of the employee, a blood condition sensor configured to output blood condition data indicative of a blood oxygenation level of the employee, a blood pressure sensor configured to output blood pressure data indicative of a blood pressure of the employee, a body fat sensor configured to output body fat data indicative of a body fat of the employee, a respiration sensor configured to output respiration data indicative of a respiration rate of the employee, a neural sensor configured to output neural data indicative of brain activity of the employee, a force sensor configured to output force data indicative of a body weight of the employee or force exerted by the employee, a position sensor configured to output position data indicative of a body position of the employee, and a camera sensor configured to output image data indicative of at least one of a biometric or biomechanic characteristic of the employee.

In some embodiments, provided is a computer implemented method for providing feedback of health information to an employee when the employee is engaged in their work duties. The method including receiving health data output by a set of one or more health sensors provided on or near the employee when the employee is engaged in work duties. The one or more health sensors including at least one of biometric sensors configured to sense biometric characteristics of the employee and biomechanic sensors configured to sense biomechanic characteristics of the employee, the health data corresponding to at least one of biometric characteristics and biomechanic characteristics sensed by the set of one or more health sensors. The method including processing the health data received to identify health status information for the employee, and providing for display via an augmented reality display, augmented reality content including the health status information. The augmented reality display providing the employee with an augmented reality view including a real world view of a surrounding environment and health status information for the employee overlaid on the real world view of the surrounding environment such that the employee is provided with an augmented reality view including a real world view of the surrounding environment having an overlay of the health status information for the employee based at least in part on the health data collected via the set of one or more health sensors provided on or near the employee when the employee is engaged in work duties.

Accordingly, as described herein below, embodiments of the system, computer program instructions and associated computer-implemented methods allow for monitoring of employees' health and for providing health information to the employees.

BRIEF DESCRIPTION OF THE DRAWINGS

So that the manner in which the features and advantages of the invention, as well as others, which will become apparent, may be understood in more detail, a more particular description of the invention briefly summarized above may be had by reference to the embodiments thereof, which are illustrated in the appended drawings, which form a part of this specification. It is to be noted, however, that the drawings illustrate only various embodiments of the invention and are therefore not to be considered limiting of the invention's scope as it may include other effective embodiments as well.

DETAILED DESCRIPTION

Figure 1:
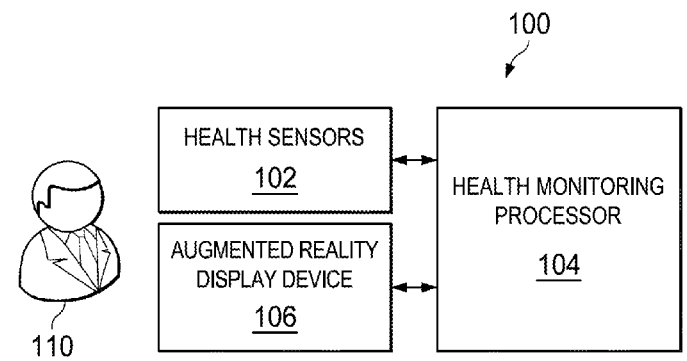
FIG. 1 is a block diagram that illustrates an employee health information system in accordance with one more embodiments of the present invention.

The present invention will now be described more fully hereinafter with reference to the accompanying drawings in which exemplary embodiments of the invention are shown. This invention may, however, be embodied in many different forms and should not be construed as limited to the illustrated embodiments set forth herein, rather, these exemplary embodiments are provided so that this disclosure will be thorough and complete, and will fully convey the scope of the invention to those skilled in the art.

In some embodiments, provided is a health monitoring system that provides a user (e.g., an employee) with feedback regarding their health (e.g., health information). In certain embodiments, the health monitoring system includes an augmented reality ("AR") display that provides for displaying health information in an employee's view of the real world. In some embodiments, the augmented reality ("AR") display includes the health information overlaid onto the user's field of view ("FOV") of the real world to provide a head-up display of the health information. Such embodiments may enable the user to view the health information while being engaged in various activities.

In certain embodiments, the health information displayed includes one or more health summaries (e.g., a listing of health characteristics, conditions, risk and/or the like for the employee) and/or one or more health alerts (e.g., a message or graphic intended to alert the employee to a health characteristics, conditions, risk and/or the like that may need attention). In some embodiments, the health alert includes information to encourage the employee to take actions that improve the employee's health and/or to discourage actions that may have a negative impact on the employee's health. In certain embodiments, the health alert may lists potential consequences to actions taken by the employee and/or predicted actions that are expected to be taken by the employee. In some embodiments, the health alert may provide coaching/suggestions (e.g., suggests alternative actions) for improving the employee's health. Thus, some embodiments may help to prevent the employee from engaging in actions that may have a negative impact on their health.

In certain embodiments, the health information is based on current health data for the employee such that the health information provides real-time feedback to the employee regarding their health. In some embodiments, the health data is collected via various health sensors (e.g., biometric and/or biomechanic health sensors) that are located on or near the employee (e.g., worn by the employee, located in a mobile device carried by the employee and/or located in the employee's workstation) while the employee is engaged in their work duties. Such embodiments may provide for collecting health data throughout the employee's workday, including when working at a desk, a remote jobsite and/or traveling.

In certain embodiments, the health data can be used to assess various biometric and biomechanic characteristics (e.g., characteristics, conditions and risks) of the employee, such as the employee's body weight, body temperature, body fat percentage, heart rate, blood pressure, blood glucose level, blood oxygenation level, body position/posture, eye fatigue, neural activity, emotions, thoughts, facial movements/expressions, motor skills, physical exertion, and the like. In some embodiments, the health data can be used to determine actions that have been taken by the employee and/or predict actions that may be taken by the employee. Thus, the health data may be indicative of the employee's health and actions while the employee is engaged in their day-to-day work activities and may enable monitoring of dynamic/real-time changes in the employee's health and actions throughout the work day.

Embodiments of the health monitoring system may provide a work environment that promotes employee involvement in monitoring of their health via a non-intrusive (e.g., passive) health testing environment. Moreover, embodiments of the health monitoring system may provide real-time feedback regarding the employee's health (e.g., via an augmented reality (AR) display) that can enable the employee to make informed decisions regarding their actions throughout the work day.

FIG. 1 is a block diagram that illustrates an employee health information system ("system") 100 in accordance with one more embodiments of the present invention. As depicted, system 100 may include a set of one or more health sensors ("sensors") 102, health monitoring processor 104 and an augmented reality (AR) display device ("AR display") 106.

In some embodiments, sensors 102 are employed to collect health data for an employee 110. The health data may be processed by health monitoring processor 104 to generate health information for the employee that is displayed to the employee via AR display 106. For example, sensors 102 may include biometric and/or biomechanic sensors that are used to sense/measure biometric and/or biomechanic characteristics of employee 110. Health data corresponding to the biometric and/or biomechanic characteristics sensed/measured may be forwarded to health monitoring processor 104 which, in turn, processes the received health data to generate health information for the employee. The health information may be displayed to the employee via AR display 106.

In some embodiments, the health information includes a health profile for the employee based at least in part on the collected health data. For example, the health information may include a health profile for the employee. The health profile may include biometric and/or biomechanic health characteristics, health conditions, and/or health risks for the employee determined using the collected health data.

In some embodiments, the health information includes a potential health consequence for the employee based at least on part on the collected health data, the employee's current health profile and/or actions that have been taken (or are predicted to be taken by the employee). For example, where it is determined that the employee has lifted a heavy item, the health information may include an identified health consequence of a high risk that the user will experience a back injury.

In some embodiments, an action to be taken by the employee is predicted based at least in part on the collected health data. For example, where the health data includes neural data indicative of the brain activity of the employee, the neural data may be used to identify thoughts of the employee, including the employee's thoughts about engaging in action in the future. In some embodiments, the identified thoughts regarding engaging in action in the future are used to predict an action by the employee and the predicted action is used to identify/predict a corresponding predicted consequence if the action were to be taken. For example, where the identified employee thought is "lift the heavy box", the thought may be used to predict that the user will engage in an action of "lifting a heavy box" and identify a predicted consequence including a high risk that the user will experience a back injury if they take the predicted action of "lifting a heavy box".

In some embodiments, augmented reality (AR) display 106 provides a view of a physical real world environment having elements that are augmented by computer generated sensory input such as sound data, video data, graphic data, or the like. Such a display may enable a user to see the real world in combination with simultaneously viewing the additional computer generated sensory input. In some embodiments, the augmented reality AR display 106 provides for overlaying information on a user's view of the real word. For example, data that may be useful to the user may be overlaid onto the user's field of view such that the user is able to view the data simultaneously while viewing the real world.

In some embodiments, AR display 106 is used to present some or all of the health information to the user. For example, AR display 106 may enable a summary of the health profile for the employee to be displayed in the employee's field of view. Thus, the employee may be able to assess their health status without having to look away from whatever they are currently working on or are otherwise focused on. Such an embodiment may be of particular use, for example, where the employee is engaged in a critical work duty that requires a great deal of attention, but where it is also critical, or at least desired, that the employee monitor their current health status.

As a further example, AR display 106 may enable an identified health consequence for the employee to be displayed in the employee's field of view. Thus, the employee may be provided real-time feedback with regard to the consequences of their actions. Such an embodiment may be of particular use, for example, where the employee is engaged in an action that may negatively affect their health, and the real-time display of the potential consequences in their field of view can help to discourage the employee from engaging in the action or similar actions.

As a further example, AR display 106 may enable predicted health consequences for the employee to be displayed in the employee's field of view. Thus, the employee may be provided real-time feedback with regard to the consequences of their predicted actions even before they actually take the action. Such an embodiment may be of particular use, for example, where the employee is about to engage in an action that may negatively affect their health, and the real-time display of the predicted consequences can help to discourage the employee from engaging in the action or similar actions.

Although some embodiments are described with regard to discouraging the employee with regard to actions that may have negative health consequences, it will be appreciated by those skilled in the art that other embodiments may include health information that encourages an employee to engage in actions that have a positive impact on their health. For example, where it has been determined that the employee has engaged in thirty minutes of exercise, the health information may include a health alert that states "Great Work! You have just burned 500 calories. Try to keep doing at least thirty minutes of exercise each day." Such positive alerts may help to provide encouragement to keep the employee engaged in a healthy lifestyle.

Figure 2:
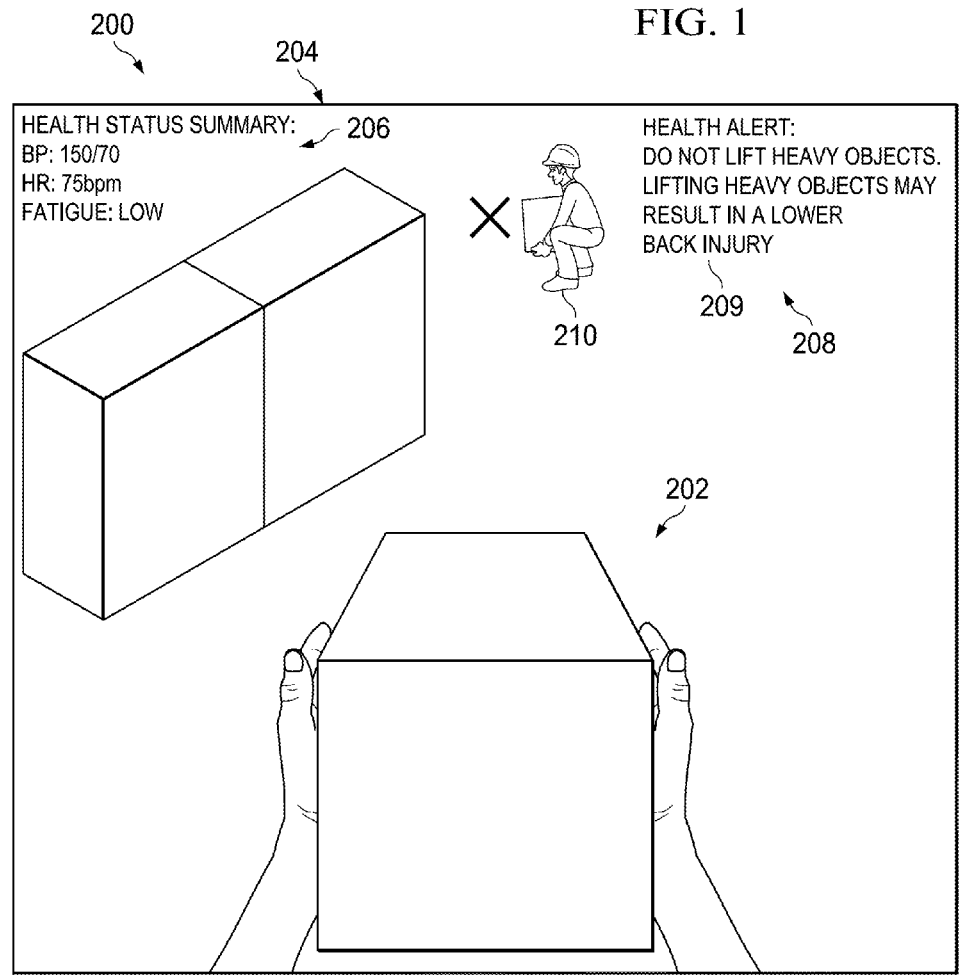
FIG. 2 illustrates an exemplary augmented reality ("AR") view provided by an augmented reality display device in accordance with one or more embodiments of the present invention.

FIG. 2 illustrates an exemplary augmented reality (AR) view 200 provided by AR display device 106 in accordance with one or more embodiments of the present invention. As depicted, AR view 200 may include a field of view ("FOV") 202 that is visible to the employee. FOV 202 may include how the employee normally views the real world. Although FOV 202 is illustrated using a bounding box for the purpose of illustration, it will be appreciated by those skilled in the art that the FOV may include the entirety of a user's field of view, including the upper, lower, right and, left peripheral edges of a person's normal FOV.

In some embodiments, AR view 200 includes health information 204 overlaid onto field of view 202. For example, as depicted, health information 204 may include text, graphics (e.g., icons), or other information used to communicate health information to the employee. The health information may be overlaid in FOV 202 such that it appears as if health information 204 is written on a transparent window through which the employee is viewing the real world.

In some embodiments, health information 204 includes a health status summary 206 that includes one or more health characteristics, health conditions, and/or health risks for the employee. For example, in the illustrated embodiment, the health status summary 206 includes a listing of the employee's current blood pressure ("BP"), heart rate ("HR") and fatigue level. As discussed herein, the content of the health status summary 206 may be based on the collected health data and/or a determined health profile for the employee.

Health status information 204 may include a health alert 208 that provides health information that urgently needs to be communicated to the employee. For example, in the illustrated embodiment, the health alert 208 includes an alert message 209 that states "Do not lift heavy objects" and "Lifting heavy objects may result in a lower back injury", accompanied by an alert icon 210 (e.g., an avatar) providing a graphic depiction indicative of a warning regarding lifting of heavy objects. In some embodiments, health alert 208 is conspicuous such that it catches the employee's attention. For example, alert icon 210 may include a blinking/flashing icon intended to catch the employee's attention and/or direct their attention to message 209. In some embodiments, the area where health alert 209 may be blank or include a default message/icon (e.g., a green check icon with the message "No alerts") when there is no current health alert that needs to be displayed.

Health alerts 208 may be tailored to the particular health information for the employee. As discussed herein, the content of health alerts 208 may be based on the collected health data, the health profile for the employee, actions determined to have been taken by the employee, predicted actions expected to be taken by the employee, and corresponding consequences related thereto. For example, where it has been determined that the user has lifted a heavy object based on the health data collected (e.g., based on the force data acquired via force sensors integrated into the employee's work gloves and/or work boots) and the health consequence of a lower back injury is associated with lifting heavy objects, an alert icon similar to that of alert icon 210 may be displayed along with an alert message that states "Do not lift heavy objects. Lifting heavy objects may result in a lower back injury" and/or a coaching suggestion to alleviate the consequence such as the message "Lift heavy objects by bending at your knees, not your back" accompanied by an animated avatar that illustrates the proper technique for lifting heavy objects by bending at your knees.

As another example, where the collected health data includes neural data indicative of the employee's intention to lift a heavy object and the health consequence of a lower back injury is associated with lifting heavy objects, a similar alert icon 210 may be displayed along with an alert message that states "Do not lift heavy objects. Lifting heavy objects may result in a lower back injury" and/or a coaching suggestion to alleviate the consequence such as "Lift heavy object by bending at your knees, not your back" accompanied by an animated avatar that illustrates the proper technique for lifting heavy objects by bending at your knees.

Although certain embodiments have been described with regard to lifting heavy objects for illustrative purposes, it will be appreciated by those skilled in the art that similar techniques may be used for identifying and displaying health information for any variety of actions and associated health consequences. For example, where the health data indicates that the employee has consumed one-thousand calories of their fifteen-hundred daily calorie intake goal (e.g., based on user logs of food they have consumed that day and a calorie intake goal of their health profile), an alert icon including depiction of food may be displayed along with an alert message that states "You have consumed 1000 calories of your 1500 daily calorie limit" and/or a coaching suggestion, such as "Try to avoid high calorie foods for the remainder of the day." As yet another example, where the health data indicates that the employee is fatigued (e.g., based on a level of fatigue determined using the collected health data), a blinking/flashing alert icon may be displayed along with an alert message that states "You are currently fatigued" and/or a coaching suggestion such as "Take a short break from your work duties."

Such embodiments (e.g., those embodiments including providing a health status summary and/or health alerts) can help inform the employee regarding their health during periods when the employee would otherwise not be aware of their current health status (e.g., while engrossed in a work duty that does not provide an opportunity to monitor their health via traditional health testing or the like). Thus, such embodiments may enable the employee to assess their health in real-time throughout the work day, and dynamically change their work habits and actions to engage in a healthier lifestyle.

AR display 106 may include a "head-up" display that superimposes (e.g., overlays) health information onto the employee's FOV. In such an embodiment, the resulting display may include a head-up view including the real-world view having information (e.g., health information) overlaid/superimposed thereon. In some embodiments, AR display 106 includes a head-mounted display ("HMD"). A HMD may be physically coupled to the employee's head such that the HMD moves in unison with the movement of the employee's head and/or eyes such that the displayed information remains in the user's FOV as they move their head and look in various directions. In some embodiments, the HMD includes a lens that is disposed in front of the eyes of the employee and that passes real world images through the lens and reflects the overlay data into the user's eyes using the lens. Thus, the overlay data (e.g., the health information) may be overlaid in the employee's FOV such that it appears as if the overlay data is written on a transparent window through which the employee is viewing the real world. In some embodiments, an HMD includes sensors that track movement of the lens (e.g., in six degrees of freedom) such that the FOV at which the employee is looking can be tracked. Such tracking can be used to determine what the employee is looking at and/or where it is relative to the employee's FOV. In some embodiments, the lens of the HMD is integrated into eyewear for the employee. For example, the lens of the HMD may include a lens of eye glasses, safety goggles/glasses, a transparent safety shield and/or the like worn by the employee during their work duties and/or other times. Thus, for example, when looking through the lens of eye glasses, safety goggles/glasses, a transparent safety shield and/or the like that are HMD's the employee may see a FOV having health information reflected thereon. Thus, the employee may be provided with a view of the real work that is similar to that of view 200 of FIG. 2.

In some embodiments, AR display 106 includes a virtual retinal display ("VRD"). A VRD may include a beam of light projects an image onto the retina of the employee. The image may include the overlay data. Thus, the overlay data (e.g., the health information) may be overlaid in the employee's FOV such that it appears as if the overlay data is written on a transparent window through which the employee is viewing the real world. In such an embodiment, the image data may be projected directly onto the employee's eye/retina, as opposed to being reflected via a separate lens.

In some embodiments, AR display 106 includes a handheld display ("HHD"). A HHD may include a device that can be held by the employee in their hand, such as a cellular phone, a personal digital assistant, a tablet computer, camera, or the like. The HHD may include a display screen that provides an image corresponding to the FOV behind/beyond the device such that it appears as if the employee is looking through the display screen of the HHD. The image may be captured by a camera facing in the opposite direction of the display screen. The display screen may be populated with an image representing the FOV and overlay data superimposed on the image. The HHD may include sensors (e.g., gyroscopes) that track position and/or orientation of the HHD that can be used to determine a position of the HHD relative to the real world environment in which it is located.

Figure 3A:
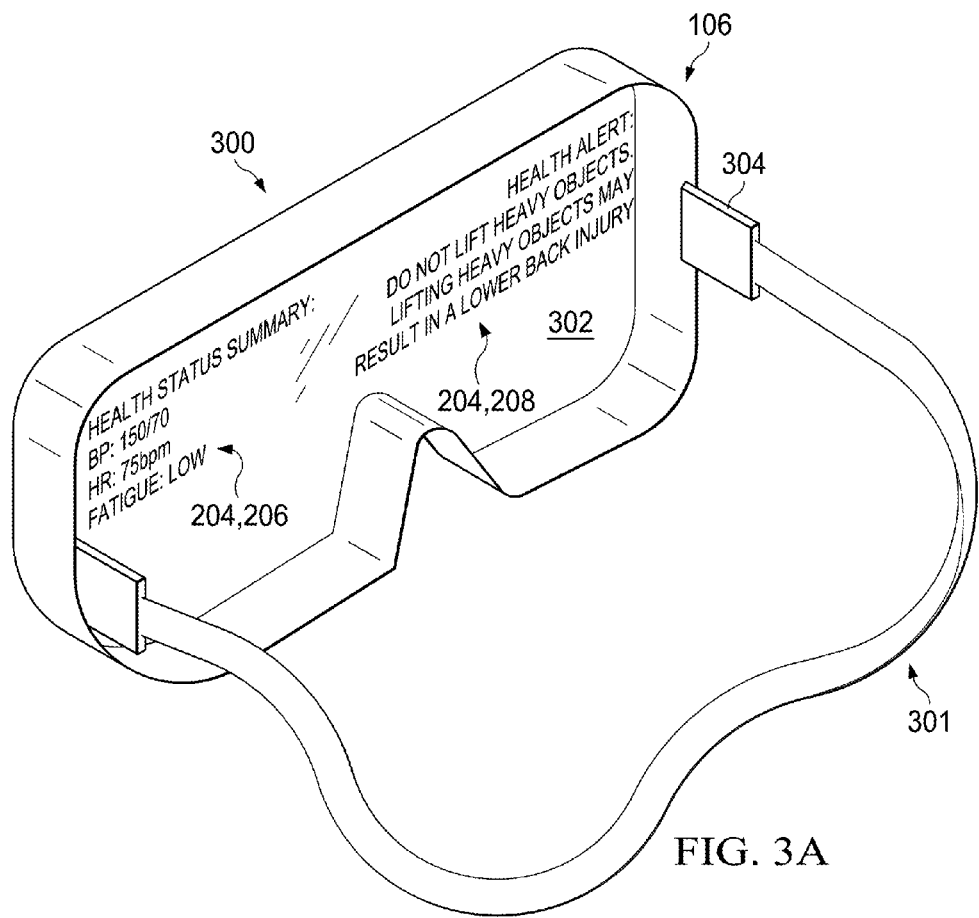
FIG. 3A illustrates an AR display system including an AR display device integrated within a pair of safety goggles in accordance with one or more embodiments of the present invention.

FIG. 3A illustrates an AR display system 300 including an AR display device 106 integrated within a pair of safety goggles 301 in accordance with one or more embodiments of the present invention. Safety goggles 300 include a pair of lenses 302, and an image projector 304. During use, image projector 304 may project an image (e.g., an image of health content 204) onto an interior side of lenses 302 that is reflected toward the employee's eyes such that the image is viewable by the employee while wearing safety goggles 300, thereby providing the employee with a head-up display on the interior of lenses 302 of safety goggles 300. The image may include, for example, health content 204 including health status summary 206, health alert 208 and/or the like. Although the illustrated embodiment includes a pair of safety goggles, it will be appreciated by those skilled in the art that other embodiments may include an AR display integrated in other eyewear, such as eye glasses, safety glasses, a transparent safety shield and/or the like worn by the employee.

Figure 3B:
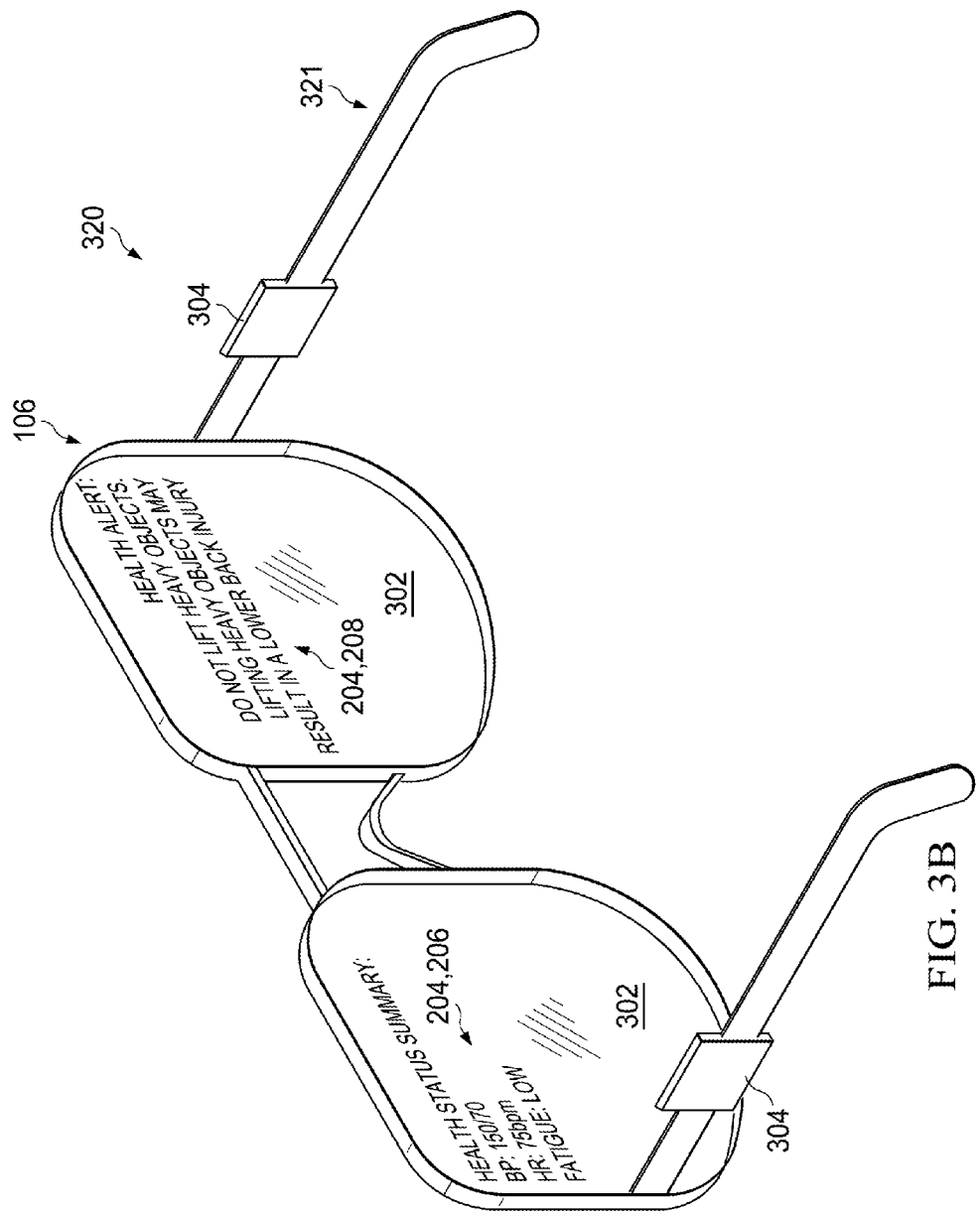
FIG. 3B illustrates an AR display system including an AR display device integrated within a pair of glasses in accordance with one or more embodiments of the present invention.

FIG. 3B illustrates an AR display system 320 including an AR display device 106 integrated within a pair of glasses 321 (e.g., safety glasses, prescription glasses, sunglasses, or the like) in accordance with one or more embodiments of the present invention. Safety glasses 321 include a pair of lenses 302 and an image projector 304. During use, image projector 304 may project an image (e.g., an image of health content 204) onto an interior side of lenses 302 that is reflected toward the employee's eyes such that the image is viewable by the employee while wearing safety glasses 320, thereby providing the employee with a head-up display on the interior of lenses 302 of safety glasses 320. The image may include, for example, health content 204 including health status summary 206, health alert 208 and/or the like.

Figure 3C:
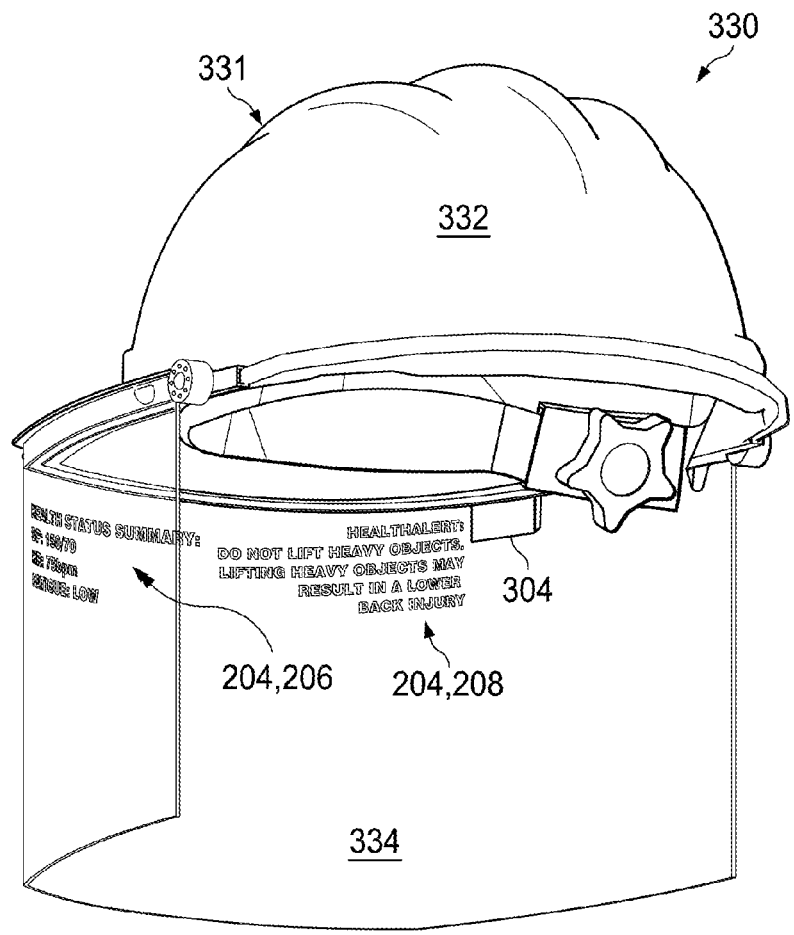
FIG. 3C illustrates an AR display system including an AR display device integrated within a safety helmet in accordance with one or more embodiments of the present invention.

FIG. 3C illustrates an AR display system 330 including an AR display device 106 integrated within a safety helmet 331 (e.g., a hard-hat) in accordance with one or more embodiments of the present invention. Safety helmet 331 includes a helmet portion 332 having a transparent safety shield/lens 334 extending downward from a front portion of the helmet 332. When worn by the employee, the shield 334 may extend in front of the employee's eye to protect them from debris or the like. The employee may view the real world look through the shield. During use, an image projector 304 may project an image (e.g., an image of health content 204) onto an interior side of shield 334 that is reflected toward the employee's eyes such that the image is viewable by the employee while wearing safety helmet 330, thereby providing the employee with a head-up display on the interior of shield 334 of safety helmet 330. The image may include, for example, health content 204 including health status summary 206, health alert 208 and/or the like.

Figure 4:
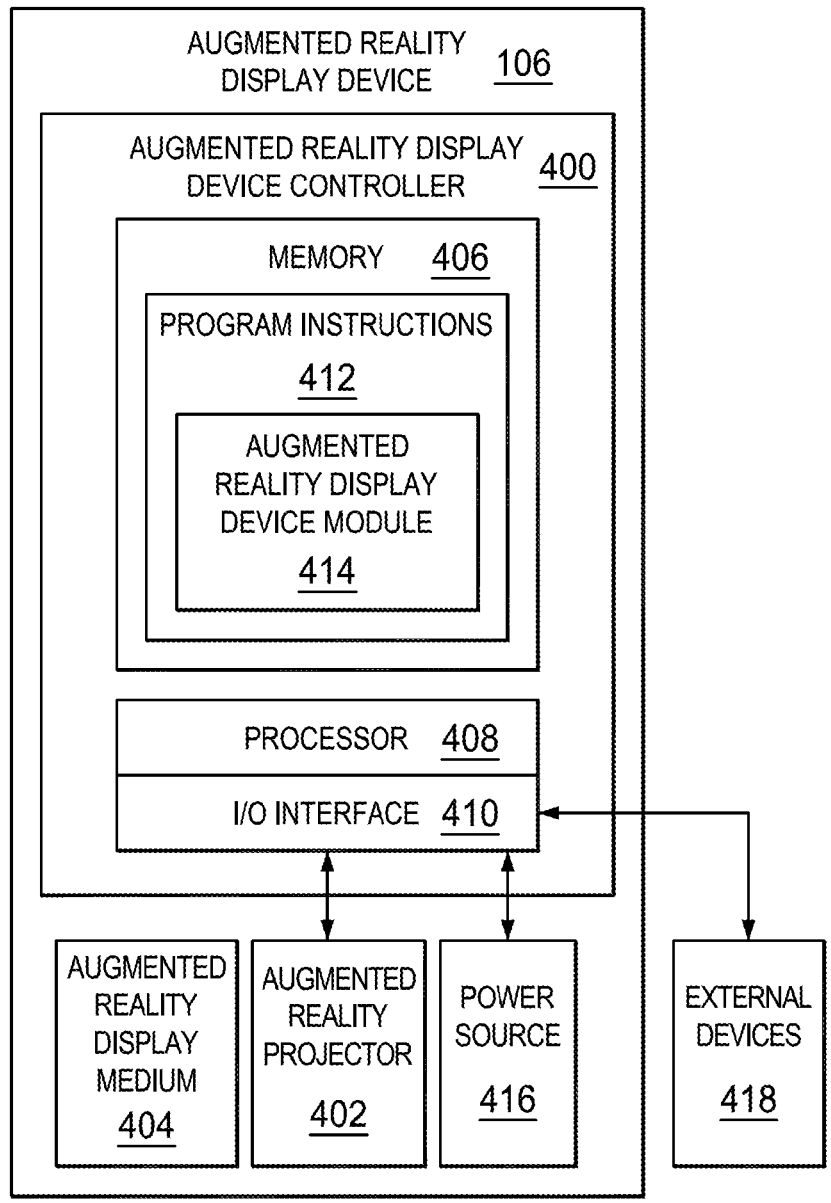
FIG. 4 is a block diagram that illustrates components of AR display device in accordance with one or more embodiments of the present invention.

FIG. 4 is a block diagram that illustrates components of AR display device 106 in accordance with one or more embodiments of the present invention. In some embodiments, AR display device 106 includes an AR display device controller 400 for controlling the operational aspects of AR display device 106. For example, where the AR display device includes an AR projector 402, the AR display device controller 400 may provide for receiving AR content (e.g., health content) to be overlaid on a field of view, supplying AR image data corresponding to the received AR content to AR projector 402 (e.g., the same as or similar to projector 304) for projecting the image onto an AR display medium 404 (e.g., 302 lenses, the employee's retina, or the like), allocating power to AR projector 402, and/or the like. In some embodiments, the AR display device controller 400 includes a memory 406, a processor 408 and an input/output (I/O) interface 410.

Memory 406 may include non-volatile memory (e.g., flash memory, ROM, PROM, EPROM, EEPROM memory), volatile memory (e.g., random access memory (RAM), static random access memory (SRAM), synchronous dynamic RAM (SDRAM)), bulk storage memory (e.g., CD-ROM and/or DVD-ROM, hard-drives), or the like. Memory 406 may include a non-transitory computer readable storage medium having program instructions 412 stored thereon that are executable by a computer processor (e.g., processor 408) to cause the functional operations (e.g., methods/routines/processes) described herein with regard to the AR display device 106. Program instructions 412 may include an AR display device module 414 including program instructions that are executable by the processor 408 to provide some or all of the functionality described herein with regard to AR display device 106.

Processor 408 may be any suitable processor capable of executing/performing program instructions. Processor 408 may include a central processing unit (CPU) that carries out program instructions (e.g., program instructions of AR display device module 414) to perform arithmetical, logical, and input/output operations of AR display device 106, including those described herein.

I/O interface 410 may provide an interface for connection of one or more I/O devices to AR display device 106. I/O devices may include AR projector 402, a power source 416 (e.g., battery), external devices 418 (e.g., health monitoring processor 104), and/or the like. External devices 418 may be connected to I/O interface 410 via a wired or wireless connection. For example, external devices 418 (e.g., health monitoring processor 104) may be connected to the I/O interface via wireless connection to a network.

During use, AR display device 106 may receive AR content to be overlaid on a field of view, processor 408 may process the AR content and provide corresponding AR image data to AR projector 402, and AR projector 402 may project an image corresponding to the AR content onto AR display medium 404 such that the AR content is overlaid in the field of view of the employee.

Figure 5:
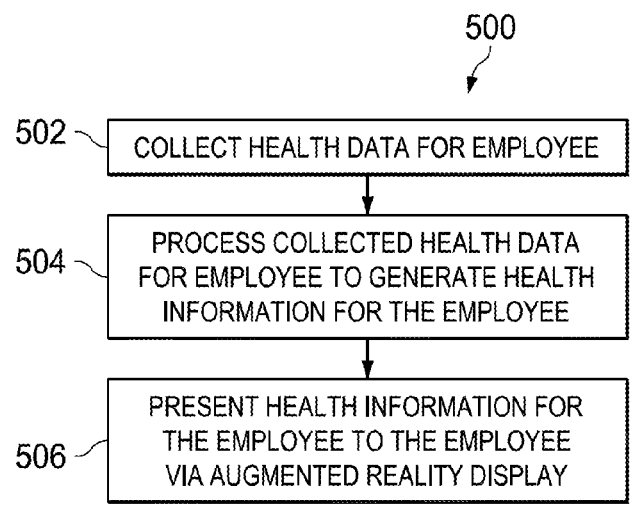
FIG. 5 is a flowchart that illustrates a method for providing health information to an employee via an AR display in accordance with one or more embodiments of the present invention.

FIG. 5 is a flowchart that illustrates a method 500 for providing health information to an employee via an augmented reality (AR) display in accordance with one or more embodiments of the present invention. Method 500 may include collecting health data for the employee, as depicted at block 502. In some embodiments, collecting health data for the employee includes health monitoring processor 104 collecting the health data for the employee sensed by health sensors 102. For example, health monitoring processor 104 may collect health data (e.g., body temperature, blood pressure, heart rate, etc. for the employee) that is sensed by corresponding health sensors 102 disposed on or near the employee (e.g., in the employee's workstation, worn by the employee, integrated with the employees clothing, safety equipment, integrated with a mobile device carried by the employee, and/or the like) while the employee is engaged in their work duties.

Method 500 may include processing the collected health data for the employee to generate health information for the employee, as depicted at block 504. In some embodiments, processing the collected health data includes health monitoring processor 104 processing the collected health data to generate health information, including for example, a health profile for the employee, to identify actions taken by the employee, to predict actions that may be taken by the employee, to identify health consequences of the actions, and/or the like. For example, processing the collected health data to generate a health profile may include health monitoring processor 104 processing the collected data to generate a health profile that includes health characteristics for the employee (e.g., health characteristics and health conditions based on the health characteristics), health risks for the employee, health plans for the employee, and/or the like. In some embodiments, the actions taken by the employee are determined base based on the health data. For example, health monitoring processor 104 may determine that the employee has lifted a heavy object based on health data that includes force data returned from sensors integrated into the employee's work gloves and/or work boots that is indicative of a relatively large force exerted by the employee's hands and/or feet. In some embodiments, the predicted actions for the employee are determined base based on the health data. For example, where the health data includes neural data indicative of the employ thought of "lift the heavy box", the thought may be used to predict that the user will engage in the action of "lifting a heavy box". In some embodiments, health consequences are based on the health data and/or the identified actions. For example, health monitoring processor 104 may identify a back injury as a consequence based on the action of "lifting a heavy box" being associated with back injuries.

Method 500 may include presenting the health information for the employee to the employee via an augmented reality (AR) display, as depicted at block 506. In some embodiment, presenting the health information for the employee to the employee via an augmented reality (AR) display includes health monitoring processor 104 providing health information content that is overlaid onto the field of view of the employee. For example, AR display device 106 may render the health information content for display such that the field of view is overlaid with a health status summary (e.g., that includes some or all of the determined health characteristics for the employee or other information of the employee's health profile) and/or a health alert that includes health information that urgently needs to be communicated to the employee (see FIG. 2).

In some embodiments, the process described with regard to method 500 is conducted continuously such that the employee is presented with a real-time display of their health information. For example, health data may be collected as fast as possible or at regular intervals (e.g., every half-second, one second, thirty-seconds, one minute, two minutes, five minutes, or the like) such that continuous a stream of health data is continually/regularly collected and processed by health monitoring processor 104. As a result, in some embodiments, the employee is provided with real-time AR display of health information that includes a delay that is attributable to the time required to acquire the health data, process the health data to generate health information, and to render the corresponding health information content for display via AR display device 106. Such real-time presentation may be of particular use when it is critical that the employ receive a warning immediately, such as displaying a predicted consequence of a predicted action to discourage the employee from taking the action before the employee has time to actually engage in the action. Even where the process is conducted at regular intervals of greater length (e.g., one minute, two minutes, five minutes, or more) such embodiments may be particularly useful as they provide the employee with substantially real-time feedback that enables the employee to assess their actions throughout the work day make dynamic adjustments during the work day to improve their health.

In some embodiments, the collection of health data, processing of the health data, and/or providing for the display of health information via an augmented reality (AR) display interface may be provided in the context of an employee health monitoring system. For example, health data may be collected from mobile devices and/or computer workstations configured to collect health data from sensors located on or near the employee (e.g., worn by the employee, integrated within a mobile device carried by the employee, and/or located in the employee's workstation), the health data may be forwarded to a health server for processing to generate health information for the employee, and the server may serve health information content (e.g., including health status summaries, health alerts, or the like) for display to the employee via an AR display device (e.g., eye glasses, safety goggles/glasses, a transparent safety shield and/or the like worn by the employee) such that the employee is provide with a head-up display of the health information.

Although certain embodiments are described with regard to various devices completing various tasks relating to collecting health data, processing the health data and presenting health information, it will be appreciated by those skilled in the art that other embodiments may include a single device or multiple other devices providing similar functionality. For example, an employee's mobile device and/or computer workstation may be employed to collect health data from the health sensors, process the collected to generate health information for the employee, and/or serve health content (e.g., including health status summaries, health alerts, or the like) for display to the employee via an AR display device. In some embodiments, the mobile device may include a handheld display ("HHD") that can display an augmented reality (AR) view including the health content overlaid on a field of view (FOV).

Figure 6:
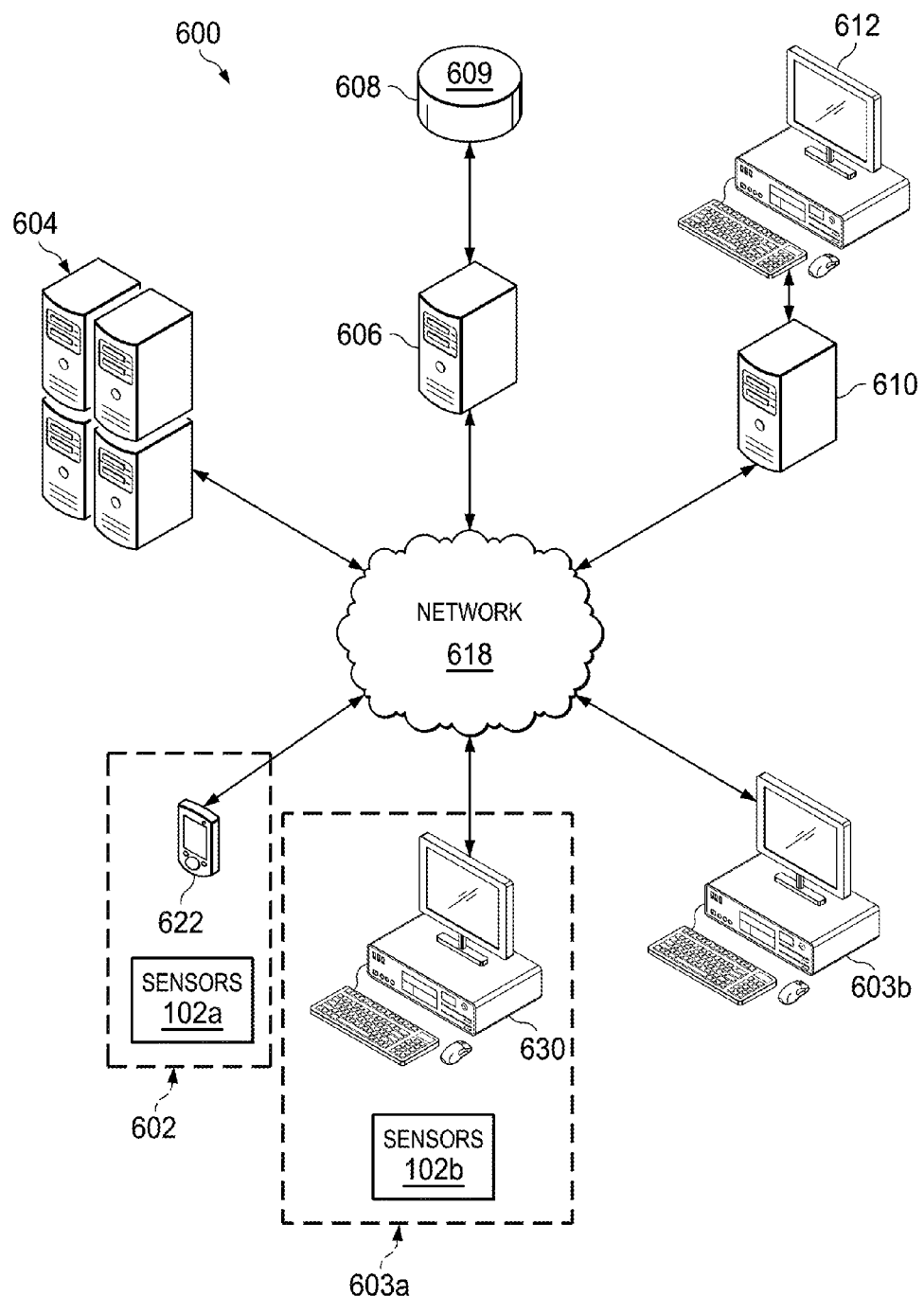
FIG. 6 illustrates an employee heath monitoring system in accordance with one more embodiments of the present invention.

FIG. 6 illustrates an employee heath monitoring system ("system") 600 in accordance with one more embodiments of the present invention. As depicted, system 600 may include one or more mobile employee health monitoring systems ("mobile health monitoring system") 602, workstations 603 (e.g., one or more employee workstations 603*a* and employer workstations 603*b*), a health server ("server") 604, a file server 606 coupled to a datastore 608 (e.g., storing health information 609 (e.g., personal profile information, health profile information, actions, consequences, and/or the like) for one or more employees), and a web server 610 connected to one or more remote workstations 612. In some embodiments, mobile employee health monitoring system 602 may include one or more health sensors 102 (e.g., mobile health sensors 102*a*) and one or more employee mobile devices ("mobile devices") 622. In some embodiments, employee workstation 603*a* may include one or more health sensors 102 (e.g., workstation health sensors 102*b*) and one or more employee computers ("employee computers") 630. In some embodiments, workstations 603*a*, 603*b* and 612 may include a networked computer or similar network access terminal. In some embodiments, the entities of system 600 may be communicatively coupled via a network 618.

In some embodiments, network 618 may include an element or system that facilitates communications between entities of system 600. For example, network 618 may include an electronic communications network, such as the Internet, a local area network ("LAN"), a wide area ("WAN"), a wireless local area network ("WLAN"), a cellular communications network, and/or the like. In some embodiments, network 618 may include a single network or combination of networks. For example, employee mobile devices 622, workstations 603, server 604, file server 606, and/or web server 610, may be networked using a private/LAN, with remote workstations 612 (e.g., employee home computers, emergency personnel computer devices, of the like) connected to web server 604 via a WAN. In some embodiments, the employee mobile device 622 may be connected to network 618 via another network node. For example, mobile device 622 may include a remote device (e.g., a cellular phone) connected to network 618 via web server 610 and a cellular communications network.

In some embodiments, mobile device 622 includes a mobile computing device. For example, mobile device 622 may include a mobile computer, such as a laptop computer, a tablet computer, a personal digital assistant ("PDA"), a cellular phone, or the like. In some embodiments, the mobile device includes a mobile communications device capable of communicating information via network 618. Mobile device 622 may be capable of connecting to and/or communicating via a LAN, a WLAN, a cellular network, and/or the like.

As described in more detail below, mobile device 622 and/or employee computer 630 may include devices employed to collect employee health data for use in monitoring an employee's health. In some embodiments, mobile device 622 and/or employee computer 630 may collect measurements from one or more health sensors 102. For example, mobile device 622 may collect measurements from one or more of mobile health sensors 102*a* and/or employee computer 630 may collect measurements from one or more of workstation health sensors 102*b*. Mobile device 622 and/or employee computer 630 may forward health data corresponding to the sensed measurements to health server 604 for use in monitoring the employee's health. For example, server 604 may generate a health profile for employee 110 (e.g., health characteristics, conditions, risks, plans, and/or the like for the employee) using the health data collected via sensors 102, mobile device 622 and/or employee computer 630. In some embodiments, mobile device 622 and/or employee computer 630 may be employed to display information relating to the health profile for the employee. For example, mobile device 622 and/or employee computer 630 may display a heath report including some or all of the health profile information for the employee such that the employee may receive feedback relating to their health via mobile device 622 and/or employee computer 630. Such a system 600 may provide for monitoring the health of the employee while they work in or travel between various work environments. For example, system 600 may enable the collection of health data while the employee is working in the field (e.g., on worksite such as an oil and gas production platform, a manufacturing plant, a refinery, a construction site, and/or the like), when they are situated in a workstation (e.g., an employee's office employee's office, cubicle, assigned station on an assembly/manufacturing line, or the like), and/or when they are traveling (e.g. traveling between worksites, driving a delivery truck, and/or the like). Thus, for example, the health data collected via health sensors 102b may be used to monitor the employee's health while the employee is located at workstation 603a, and the health data collected via the health sensors 102a of mobile health monitoring system 602 may be used to monitor the employee's health while the employee is not located at the workstation 603a (e.g., traveling or working at a remote worksite). Although some embodiments are described with regard to a health profile based on health data collected via sensors 102, mobile device 622 and/or employee computer 630, other embodiments may include a health profile based on health data collected from any variety of sources as will be understood by those skilled in the art.

In some embodiments, the health data may include measurements that can be used to assess various biometric aspects of the employee's health, such as one or more of body temperature, body weight, body fat, heart rate, respiratory rate, blood pressure, blood oxygen saturation ("blood oxygenation"), blood glucose level, neural/brain activity, and/or the like. In some embodiments, the health data may include measurements that can be used to assess various biomechanic aspects of the employee's health, such as one or more of body position, posture, muscle tension, eye fatigue, facial expression, motor skills, and/or the like. Sensors that are used to acquire measurements for use in assessing various biometric aspects of the employee's health may be referred to as "biometric sensors". Sensors that are used to acquire measurements for use in assessing various biomechanic aspects of the employee's health may be referred to as "biomechanic sensors". Sensors that provide are used to acquire measurements for use in assessing both biometric and biomechanic aspects of the employee's health may be referred to as "biometric" and/or "biomechanic" sensors.

As discussed in more detail below, in some embodiments, mobile device 622 and/or employee computer 630 may provide for collecting health data from various sensors 102 and/or forwarding corresponding health data to server 604 for use in monitoring an employee's health. For example, in response to determining that employee's health data needs to be collected (e.g., based on a request from server 604, a request from the employee, a predetermined test schedule, or the like), mobile device 622 and/or employee computer 630 may monitor the sensors 102a and/or 102b to collect health data (e.g., collect measurements) therefrom, and may forward corresponding health data to server 604 for use in monitoring the health of the employee. Although certain embodiments are described with regard to the mobile device 622 and/or employee computer 630 collecting the health data measurements and forwarding corresponding health data to server 604, in other embodiments, some or all of the health data may be provided directly to server 604 (i.e., without having to pass the data through mobile device 622 and/or employee computer 630). For example, sensors 102 may be communicatively coupled to network 618 (e.g., via a WLAN) such that they can transmit heath data directly to server 604 via the network 618.

Figure 7A:
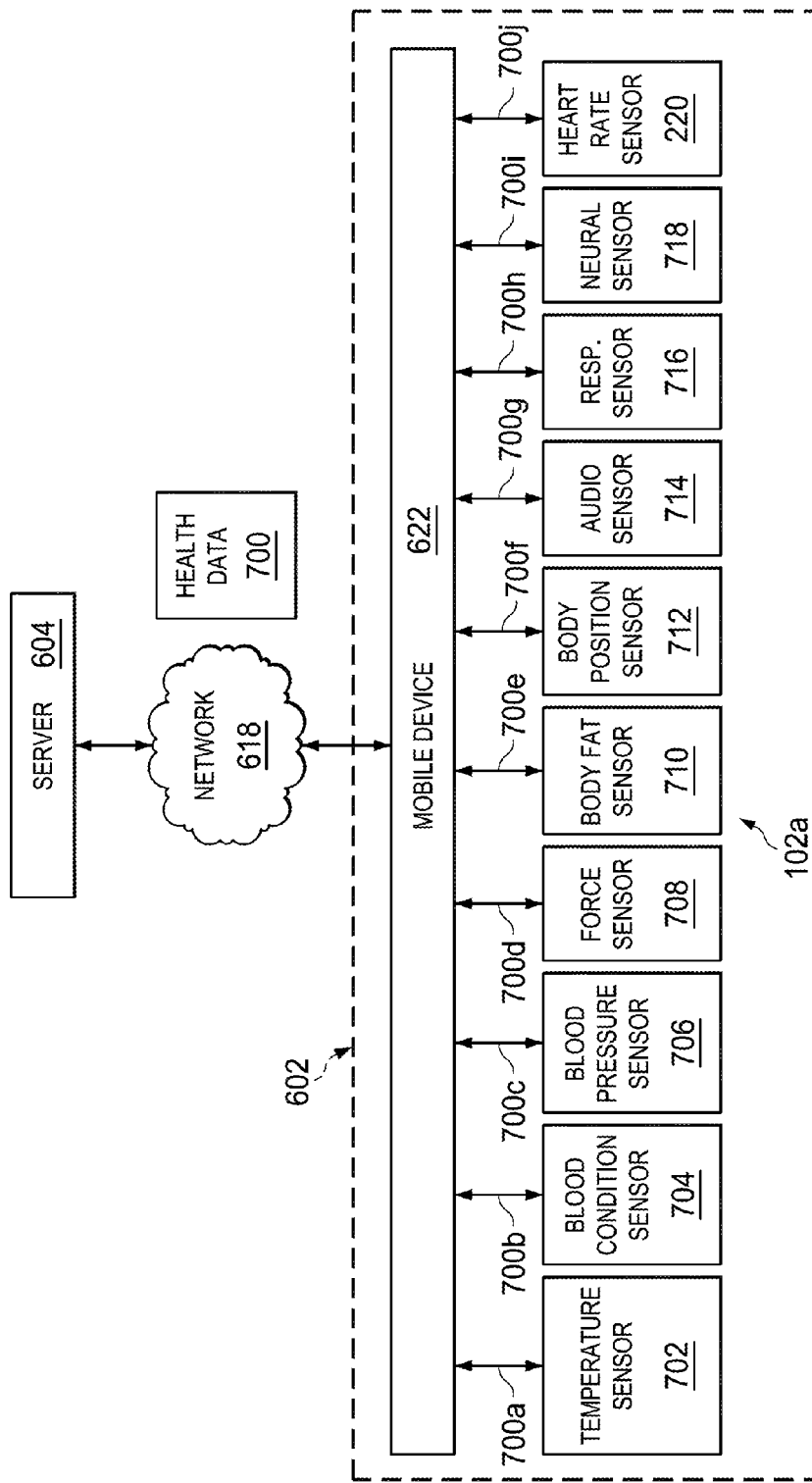
FIG. 7A is a block diagram that illustrates a mobile health monitoring system connected to a server via a network in accordance with one or more embodiments of the present invention.
Figure 7B:
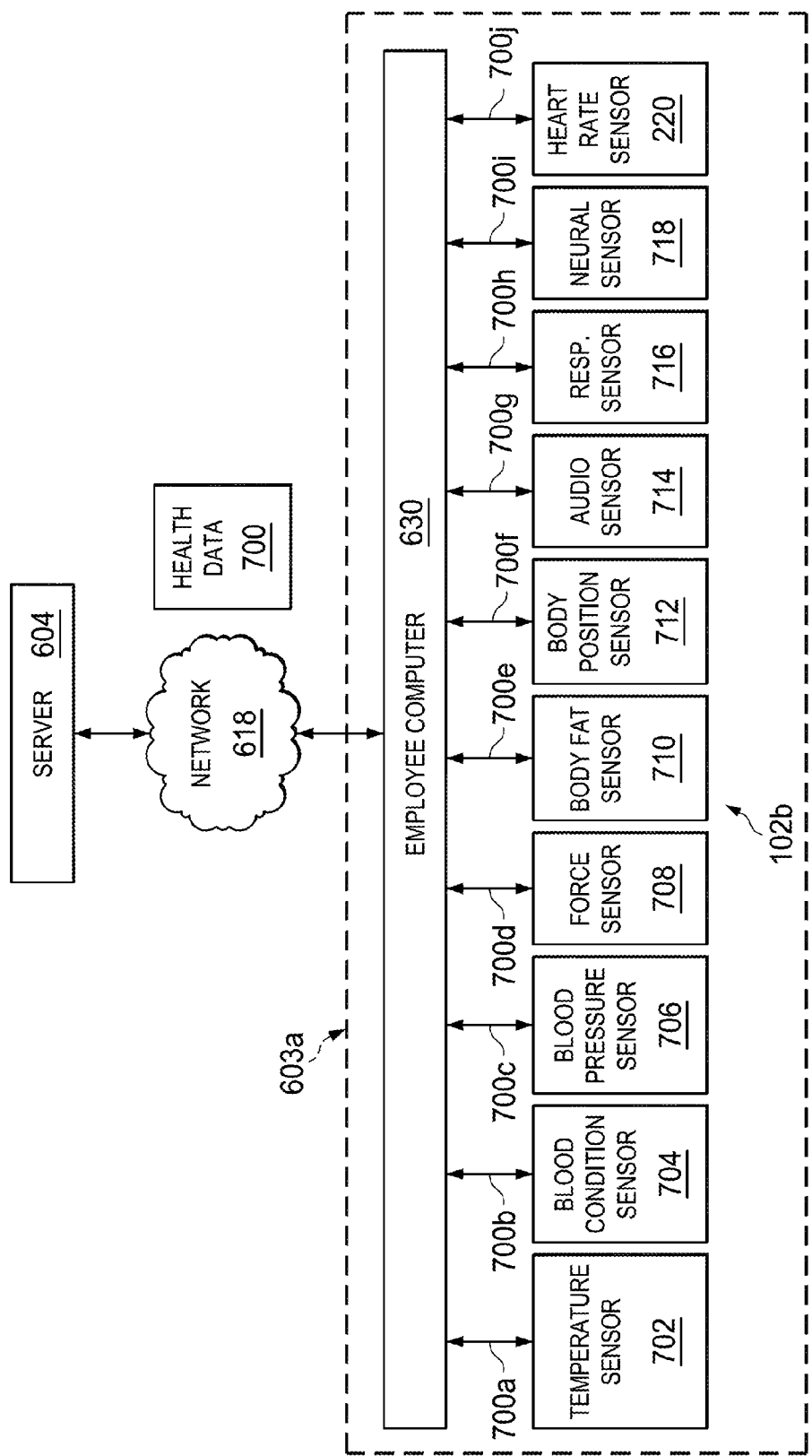
FIG. 7B is a block diagram that illustrates a health monitoring workstation connected to a server via a network in accordance with one or more embodiments of the present invention.

FIGS. 7A and 7B are block diagrams that illustrates a mobile health monitoring system 602 and workstation 603a, respectively, connected to server 604 via the network 618 in accordance with one or more embodiments of the present invention. In some embodiments, mobile device 622 and/or employee computer 630 are communicatively coupled to one or more of sensors 102a and/or 102b for collecting employee health data 700. For example, mobile device 622 and/or employee computer 630 may be communicatively coupled to one or more temperature sensors (e.g., thermocouples, infrared ("IR") sensors, etc.) 702, one or more blood condition sensors (e.g., pulse oximeters) 704, one or more blood pressure sensors (e.g., a blood pressure cuff) 706, one or more force sensors (e.g., force transducers) 708, one or more body fat sensors (e.g., conductive contacts) 710, one or more body position sensors (e.g., three-dimensional ("3D") image/video camera) 712, one or more audio sensors (e.g., microphone) 714, one or more respiration sensors 716, one or more neural sensors 718, one or more heart rate sensors 720 (e.g., a heart rate monitor) and/or the like for collecting corresponding health data 700 (e.g., health measurements) therefrom. In some embodiments, health data 700 may include temperature data 700a, blood condition data 700b, blood pressure data 700c, force data 700d, body fat data 700e, body position data 700f, audio data 700g, respiration data 700h, neural data 700i and/or heart rate data 700j, collected from the corresponding sensors 102a and/or 102b. Health data 700 corresponding to the measurements may be provided to server 604 for use in monitoring the employee's health.

In some embodiments, mobile device 622 and/or employee computer 630 are communicatively coupled to sensors 102a and/or 102b via a wired connection. For example, some or all of the sensors 102a and/or 102b may include a communication cable extending between each of the respective sensors and mobile device 622 and/or employee computer 630. In some embodiments, mobile device 622 and/or employee computer 630 may be communicatively coupled to sensors 102a and/or 102b via a wireless connection. For example, some or all of sensors 102a and/or 102b may communicate with mobile device 622 and/or employee computer 630 via a wireless connection such as a Bluetooth connection, a WLAN of network 618, and/or the like). In some embodiments, heath data 700 (e.g., 700a-700j) is transmitted from the respective sensors 102a and/or 102b to mobile device 622 and/or employee computer 630 via the wired or wireless connections. In some embodiments, health data 700 is transferred between devices of system 600 via a non-transitory storage medium such as a universal serial bus ("USB") memory stick (e.g., a flash drive). For example, health data 700 acquired from sensors 102a and/or 102b may be downloaded from sensors 102a and/or 102b, from mobile device 622 and/or from employee computer 630 to a USB memory stick and may be uploaded from the USB memory stick to another device of system 100, such mobile device 622, employee computer 630, employer workstation 603b, remote workstation 612, and/or sever 604.

Figure 8:
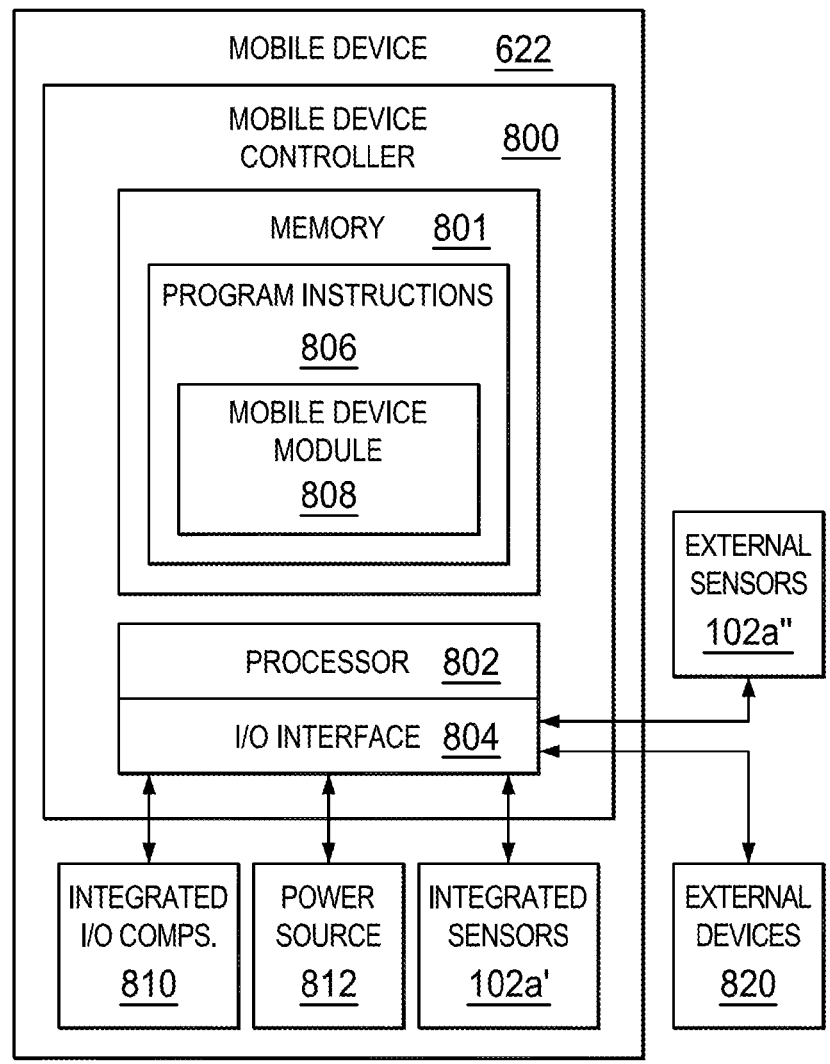
FIG. 8 is a block diagram that illustrates components of mobile device in accordance with one or more embodiments of the present invention.

FIG. 8 is a block diagram that illustrates components of mobile device 622 in accordance with one or more embodiments of the present invention. In some embodiments, mobile device 622 includes a mobile device controller 800 for controlling the operational aspects of mobile device 622. For example, mobile device controller 800 may provide for allocating power to integrated devices, collecting health data 700 from the various sensors 102a and/or transmitting the collected health data 700 to server 604. In some embodiments, the mobile device controller includes a memory 801, a processor 802 and an input/output (I/O) interface 804.

Memory 801 may include non-volatile memory (e.g., flash memory, ROM, PROM, EPROM, EEPROM memory), volatile memory (e.g., random access memory (RAM), static random access memory (SRAM), synchronous dynamic RAM (SDRAM)), bulk storage memory (e.g., CD-ROM and/or DVD-ROM, hard-drives), or the like. Memory 801 may include a non-transitory computer readable storage medium having program instructions 806 stored thereon that are executable by a computer processor (e.g., processor 802) to cause the functional operations (e.g., methods/routines/processes) described herein with regard to mobile device 622. The program instructions 806 may include a mobile device module 808 including program instructions that are executable by processor 802 to provide some or all of the functionality described herein with regard to mobile device 622.

Processor 802 may be any suitable processor capable of executing/performing program instructions. Processor 802 may include a central processing unit (CPU) that carries out program instructions (e.g., of mobile device module 808) to perform arithmetical, logical, and input/output operations of mobile device 622, including those described herein.

I/O interface 804 may provide an interface for connection of one or more I/O devices to mobile device 622. I/O devices may include integrated I/O components (e.g., buttons, microphone, speaker, graphical display (e.g., a touch screen), cameras, and/or the like) 810, a power source 812 (e.g., a battery), integrated sensors 102a', external devices 820 (e.g., server 604), and/or the like. External devices 820 may be connected to I/O interface 804 via a wired or wireless connection. For example, external devices 820 (e.g., server 604) may be connected to the I/O interface via wireless connection to network 618. In some embodiments, integrated sensors 102a' include sensors 102a that are physically integrated within mobile device 622. For example, integrated sensors 102a' may include conductive contacts integrated into the exterior of mobile device 622 such that a measurement (e.g., temperature measurement, a resistance measurement indicative of body fat, and/or the like) can be acquired via the conductive contacts while the user is grasping the exterior of mobile device 622. In some embodiments, external sensors 102a" include sensors 102a that are remote from mobile device 622. For example, external sensors 102a" may include temperature sensors 712, blood pressure sensors 706, or the like that are worn by the employee to take measurements at various locations on the employee's body.

Figure 9:
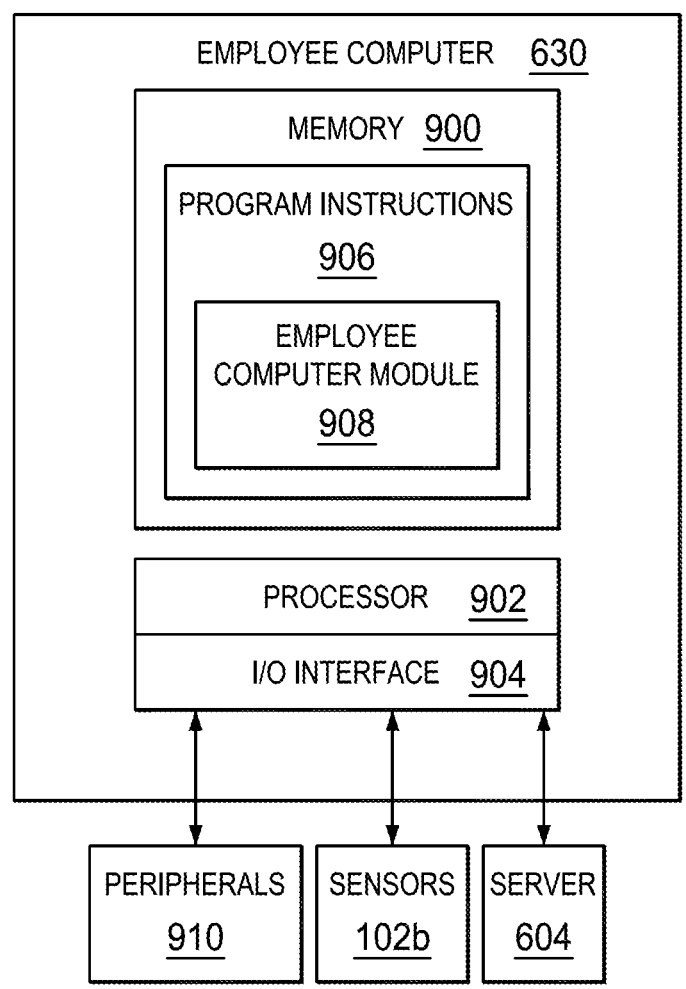
FIG. 9 is a block diagram that illustrates components of employee computer in accordance with one or more embodiments of the present invention.

FIG. 9 is a block diagram that illustrates components of employee computer 630 in accordance with one or more embodiments of the present invention. In some embodiments, employee computer 630 includes a memory 900, a processor 902 and an input/output (I/O) interface 904.

Memory 900 may include non-volatile memory (e.g., flash memory, ROM, PROM, EPROM, EEPROM memory), volatile memory (e.g., random access memory (RAM), static random access memory (SRAM), synchronous dynamic RAM (SDRAM)), bulk storage memory (e.g., CD-ROM and/or DVD-ROM, hard-drives), or the like. Memory 900 may include a non-transitory computer readable storage medium having program instructions 906 stored thereon that are executable by a computer processor (e.g., processor 902) to cause the functional operations (e.g., methods/routines/processes) described herein with regard to employee computer 630. The program instructions 906 may include an employee computer module 908 including program instructions that are executable by processor 902 to provide some or all of the functionality described herein with regard to employee computer 630.

Processor 902 may be any suitable processor capable of executing/performing program instructions. Processor 902 may include a central processing unit (CPU) that carries out program instructions (e.g., of employee computer module 908) to perform arithmetical, logical, and input/output operations of employee computer 630, including those described herein.

I/O interface 904 may provide an interface for connection of one or more I/O devices to employee computer 630. I/O devices may include peripherals 910, sensors 102b, server 604, and/or the like. Peripherals 910 may include, for example, graphical user interface displays (e.g., a cathode ray tube (CRT) or liquid crystal display (LCD) monitor), pointing devices (e.g., a computer mouse or trackball), keyboards, keypads, touchpads, scanning devices, voice recognition devices, gesture recognition devices, printers, audio speakers, microphones, cameras, and/or the like. I/O devices (e.g., peripherals 910, sensors 102b, and server 604) may be connected to the I/O interface 904 via a wired or wireless connection.

Mobile device 622 and/or employee computer 630 may be employed to collect health data 700 from the various sensors 102 (e.g., mobile sensors 102a and/or workstation sensors 102b) and/or forward corresponding health data 700 to server 604 for use in monitoring the employee's health. For example, in response to determining that health data 700 (e.g., temperature data 700a, blood condition data 700b, blood pressure data 700c, position data 700d, body fat data 700e, 3D position data 700f, audio data 700g, respiration data 700h, neural data 700i and/or heart rate data 700j) needs to be collected, mobile device 622 and/or employee computer 630 may employ, or otherwise monitor, one or more of the particular sensors 102 capable of sensing/measuring the needed health data 700 such that the needed health data 700 is transmitted from the various sensors 102 to mobile device 622 and/or employee computer 630, mobile device 622 and/or employee computer 630 collect/store the needed health data 700 (e.g., store/queue the acquired health data 700 in memory 801 and/or 900), and/or mobile device 622 may forward health data 700 to server 604 for use in monitoring the employee's health.

In some embodiments, mobile device 622 and/or employee computer 630 process the raw/acquired health data to generate corresponding processed health data. For example, where mobile device 622 and/or employee computer 630 receives raw health data (e.g., temperature data 700a including a voltage indicative of a sensed temperature), mobile device 622 and/or employee computer 630 may process the raw health data to generate a corresponding value (e.g., using a look-up table, equation or the like to identify a temperature value corresponding to the voltage) that may be included in health data 700 transmitted to server 604. Accordingly, in some embodiments, health data 700 may include the raw/acquired health data (e.g., a voltage value) and/or the processed health data corresponding thereto (e.g., the temperature value corresponding to the voltage value). Similar processing may be provided for the other types of health data.

In some embodiments, mobile device 622 and/or employee computer 630 forward health data 700 as the corresponding health data is received. For example, mobile device 622 and/or or employee computer 630 may receive health data 700 from sensors 102a and/or 102b and immediately forward health data 700 with little to no delay such that a continuous stream of health data 700 is provided to server 604 for use in monitoring the employee's health. In some embodiments, mobile device 622 and/or employee computer 630 may store (e.g., queue or buffer) health data 700 for transmission at a later time. For example, where a test routine requires that mobile device 622 and/or employee computer 630 transmit a batch of health data 700 at the end of a test cycle, on a regular interval (e.g., every ten minutes), or the like, health data 700 may be stored in memory 801 and/or 900 as a batch of health data 700 that is queued-up and/or buffered for transmission to server 604 at the end of the test cycle, at the regular interval, or the like.

In some embodiments, a temperature sensor 702 includes thermocouples, IR sensors, or the like. During use, temperature sensor 702 may transmit health data 700 indicative of a temperature sensed by the temperature sensor 702 (e.g., a temperature measurement). For example, where a temperature sensor 702 is positioned to acquire the employee's body temperature at a given location (e.g., at their hand, wrist, head, chest or the like), mobile device 622 and/or employee computer 630 may receive, from the temperature sensor 702, the temperature data 700a indicative of the body temperature (e.g., 37° C. (98.6° F.)) at the given location.

In some embodiments, a blood condition sensor 704 includes pulse oximeters, blood glucose testing devices, and/or the like. The blood condition sensor 204 may include, for example, the OctiveTech™ 300IH Pulse Oximeter manufactured by Nellcor™ or the BCI™ 3301 Hand Held Pulse Oximeter manufactured by Smiths Medical™. During use, the mobile device 622 and/or employee computer 630 may receive health data 700 indicative of blood characteristics sensed by blood condition sensor 704. For example, where a pulse oximeter is positioned about the employee's fingertip, mobile device 622 and/or employee computer 630 may receive, from the pule oximeter, blood condition data 700b indicative of various aspects of the employee's blood, such as the employee's blood oxygenation level at the employee's fingertip (e.g., 95% oxygenation).

In some embodiments, a blood pressure sensor 706 includes blood pressure cuffs and/or the like. The blood pressure sensor 706 may include, for example, the UA-789PC Extra Large Cuff sold by LifeSource™ and the CMS-08A Professional Upper Arm Blood Pressure Monitor manufactured by CMS™. During use, mobile device 622 and/or employee computer 630 may receive health data 700 indicative of the employee's blood pressure sensed by blood pressure sensor 706. For example, where a blood pressure cuff is positioned about the employee's wrist/arm, mobile device 622 and/or employee computer 630 may receive, from the blood pressure cuff, blood pressure data 700c indicative of the employee's blood pressure (e.g., 90/60 mmHg) sensed at the employee's wrist/arm.

In some embodiments, a force sensor 708 includes force transducers, such as strain gauges, load cells and/or the like. During use, mobile device 622 and/or employee computer 630 may receive health data 700 indicative of the force sensed by force sensor 708. For example, where load cells are positioned in the employee's footwear (e.g., in the employee's right and left work boots) or on the floor of the employee's workstation 603a, and the employee is standing, mobile device 622 and/or employee computer 630 may receive, from the load cells, force data 700d indicative of the forces exerted by the employee's feet. Such force data 700d may be used to calculate a weight of the employee (e.g., 56.5 kg (124.6 lbs.) a body position of the employee or the like. As a further example, where load cells are positioned in the employee's hand wear (e.g., in the employee's right and left work gloves) and the employee is lifting an object, mobile device 622 and/or employee computer 630 may receive, from the load cell, force data 700d indicative of the forces exerted by the employee's hands. Such force data 700d may be used to determine the weight of an object being lifted and/or the physical exertion by the employee.

In some embodiments, a body fat sensor 710 includes conductive contacts that can be used to sense resistivity in the employee's body tissue and/or the like. During use, mobile device 622 and/or employee computer 630 may receive health data 700 indicative of the employee's body fat sensed by body fat sensor 710. For example, where conductive contacts are integrated within the right and left sides of mobile device 622 and the employee grasp the right and left sides of the mobile device with their right and left hands, respectively, such that their hands contact the conductive contacts, mobile device 622 may receive, from the conductive contacts, body fat data 700e including a resistance measurement across the conductive contacts that is indicative of the body fat of the employee. Where conductive contacts are integrated within the right and left sides of a seat of the employee's chair and the employee is seated in the chair, such that their right and left upper leg/buttocks contact the conductive contacts, mobile device 622 and/or employee computer 630 may receive, from the conductive contacts, body fat data 700e including a resistance measurement across the conductive contacts that is indicative of the body fat of the employee.

In some embodiments, a body position sensor 712 includes a camera (e.g., a two-dimensional still/video camera, a three-dimensional ("3D") still/video camera, and/or the like that can be used to sense the employee's body position. During use, mobile device 622 and/or employee computer 630 may receive health data 700 indicative of the physical position of the employee as sensed by the body position sensor 712. For example, where a body position sensor 712 includes a 3D video camera positioned such that the employee's body is within its field of view, mobile device 622 and/or employee computer 630 may receive, from the 3D camera, body position data 700f (e.g., a three-dimensional video image) indicative of the position (e.g., head, arm, hand, torso, leg, and feet position and/or posture) of the employee. In some embodiments, the image/video data may be used to track the eye movement of the employee. For example, where the employee's head is in the field of view of the video camera, body position data 700f may include images that can be used to track the eye position of the employee, the employee's eye blink rate, the employee's pupil dilatation and/or the like. In some embodiments, a 3D camera may include a device such as the Kinect™ manufactured by Microsoft. Such a 3D camera may include a software development kit that provides for employing the camera as a biomechanical sensor for determining various biometric aspects of the employee, including body position. Though a specific 3D video camera device is described herein, other such cameras may be manufactured that can be adapted for use in the instant system as will be understood by those skilled in the art. For example, any camera may be employed that is capable of capturing 3D body images such that movements may be "sensed" and corresponding data extrapolated for use in monitoring the health of the employee (e.g., via a posture analysis, eye fatigue analysis, etc.).

In some embodiments, a body position sensor 712 includes one or more positioning devices (e.g., RFID sensors) that can be used to locate a relative or absolute position of the employee. For example, where a positioning device is provided in the employee's chair, boots, work gloves, helmet, elbow pads, knee pads, and/or belt, body position data 700f may include signals and/or coordinates indicative of the location of each of the positioning devices such that a location of the employee's hands, feet, head, elbows, knees, and/or waist can be determined. Such location information may be used to determine the employee's body position, including an analysis of their posture. In some embodiments, position sensor 712 may include a combination of different types of positions sensors (e.g., a 3D camera, positioning devices, and/or the like) that can be used in combination to determine the employee's body position.

In some embodiments, an audio sensor 714 includes a microphone or the like for acquiring audio data (e.g., words spoken by the employee). During use, mobile device 622 and/or employee computer 630 may receive health data 700 indicative of the audio data sensed by audio sensor 714. For example, where audio sensor 714 includes a microphone, the mobile device 622 and/or employee computer 630 may receive, from audio sensor 714, audio data 700g (e.g., an audio feed) indicative of words spoken by the employee.

In some embodiments, respiration sensor 716 includes a device for sensing the employee's respiration rate (e.g., number of breaths taken within a set amount of time, typically sixty seconds. During use, mobile device 622 and/or employee computer 630 may receive health data 700 indicative of the respiration rate ("RR") of the employee sensed by respiration sensor 716. For example, mobile device 622 and/or employee computer 630 may receive, from respiration sensor 716, respiration data 700h indicative of number of breaths taken by the employee over sixty seconds (e.g., 15 breaths per minute).

In some embodiments, neural sensor 718 includes a device (e.g., an electrode) for sensing brain activity (e.g., neural activity) of the employee. In some embodiments, neural sensors 718 may employ electroencephalography ("EEG") to measure neuro-signal voltage fluctuations resulting from ionic current flows within the neurons of the brain. EEG may refer to recording of the brain's spontaneous electrical activity over a short period of time (e.g., twenty-forty minutes) from a plurality of neural sensors 718 disposed on the employee's scalp. For example, a plurality of neural sensor 718 (e.g., sixteen neural sensors/channels) may be disposed about the employee's scalp to detect neuro-signals (e.g., including alpha, beta, gamma, and delta waves) that can be used to determine the employee's brain state, including their emotional state (e.g., happy, sad, excited, etc.), thoughts (e.g., cognitive thoughts, subconscious thoughts, intent, etc.), facial movements (e.g., facial expressions), motor functions and/or the like. During use, mobile device 622 and/or employee computer 630 may receive health data 700 indicative of the employee's neural activity sensed by neural sensors 718. For example, mobile device 622 and/or employee computer 630 may receive, from neural sensors 718, neural data 700i indicative of the sensed neuro-signals.

In some embodiments, a heart rate sensor 720 may include a heart rate monitor. During use, mobile device 622 and/or employee computer 630 may receive health data 700 indicative of the employee's heart rate sensed by heart rate sensor 720. For example, where a heart rate monitor is positioned about the employee's torso, mobile device 622 and/or employee computer 630 may receive, from the heart rate monitor, heart rate data 700j indicative of the employee's hear rate (e.g., 80 beats per minute ("BPM")).

In some embodiments, some or all of sensors 102 may be located at or near the employee 110 (e.g., worn by the employee 110) and/or physically integrated with mobile device 622. For example, various ones of sensors 102 may be provided in the employee's apparel, such as their clothing (e.g., shirt and pants, gloves, etc.), footwear (e.g., work boots), head wear (e.g., a safety helmet), and eyewear (e.g., safety glasses) and/or various ones of sensors 102 may be located in mobile device 622.

Figure 10:
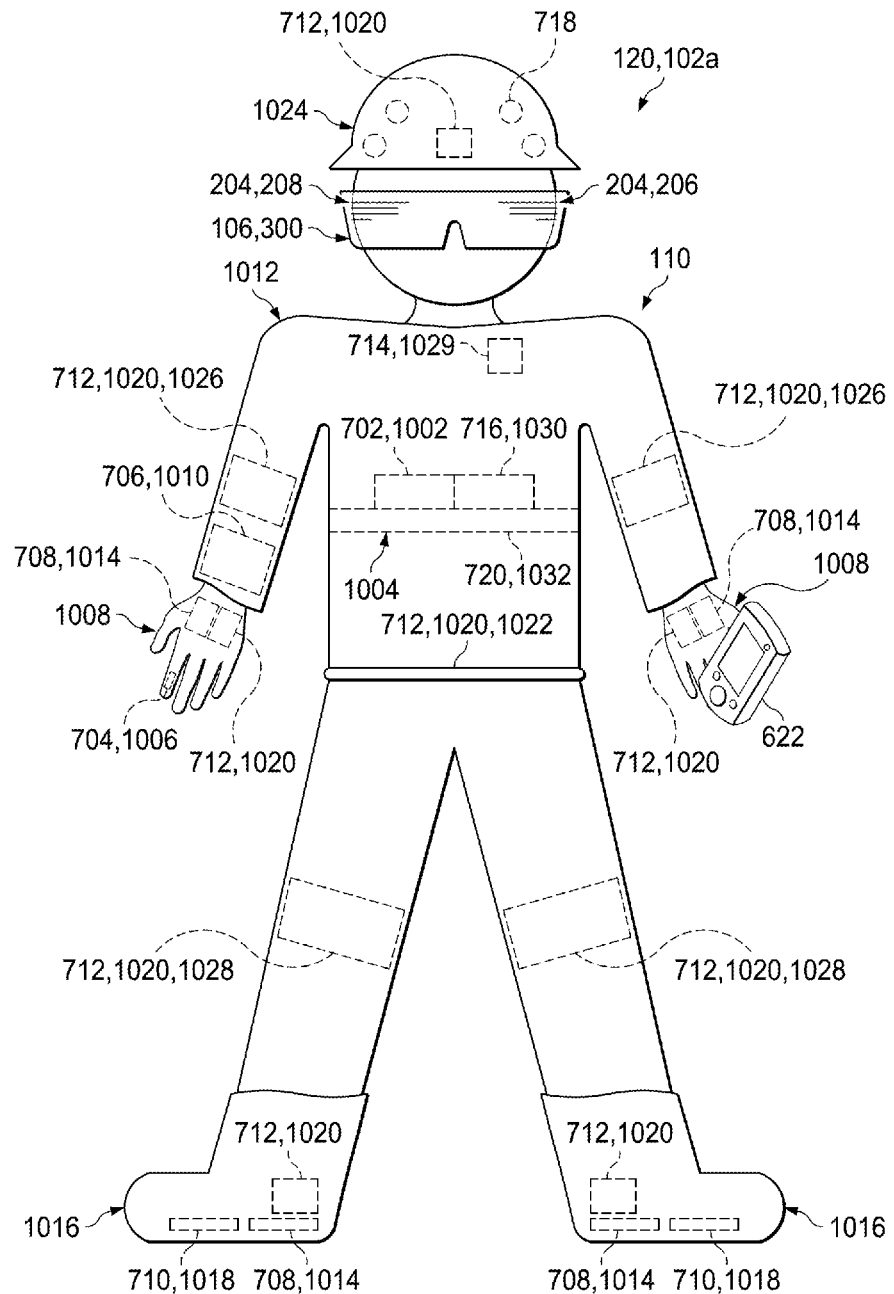
FIG. 10 is a diagram that illustrates an employee wearing various sensors in accordance with one or more embodiment of the present invention.

FIG. 10 is a diagram that illustrates employee 110 wearing various sensors 102 in accordance with one or more embodiment of the present invention. In some embodiments, sensors 102 include mobile sensors 102a and/or workstation sensors 102b. In some embodiments, a temperature sensor 702 is disposed at the employee's chest. For example, temperature sensor 702 may include a thermometer/thermocouple 1002 secured around the employee's torso via a strap 1004. Other embodiments may include any number of temperature sensors provided in any number of suitable locations such as the employee's hand, wrist, arms, back, head, feet and/or the like.

In some embodiments, a blood condition sensor 704 is disposed at the employee's finger. For example, blood condition sensor 704 may include a pulse oximeter 1006 integrated with a finger portion of work gloves 1008 worn by the employee. Other embodiments may include any number of blood condition sensors provided in any number of suitable locations such as the employee's earlobe, toe and/or the like.

In some embodiments, a blood pressure sensor 706 is disposed at the employee's arm/wrist. For example, blood pressure sensor 706 may include a blood pressure cuff 1010 secured about the employee's wrist. In some embodiments, blood pressure cuff 1010 may be integrated into a sleeve 1012 of the employee's shirt. Other embodiments may include any number of blood pressure sensors provided in any number of suitable locations such as the employee's upper-arm and/or the like.

In some embodiments, force sensors 708 are disposed at the employee's hands and/or feet. For example, force sensors 708 may include force transducers 1014 integrated within the palm portion of work gloves 1008 worn by the employee. Such force transducers 1014 may enable a determination of a force exerted by the employee's hands (e.g., while lifting an object). As a further example, force sensors 708 may include force transducers 1014 integrated within the sole portion of work boots 1016 worn by the employee. Such force transducers 1014 may enable a determination of a force exerted on the employee's foot which can, for example, be used to determine the employee's weight. Other embodiments may include any number of force sensors provided in any number of suitable locations such as the employee's back, buttocks area and/or the like.

In some embodiments, body fat sensors 710 are disposed at the employee's feet. For example, body fat sensors 710 may include conductive contacts 1018 integrated within the sole portion of the work boots 1016 worn by the employee. The conductive contacts may contact the sole of the employee's feet. Such body fat sensors 710 may enable a determination of a resistance across the employee's feet that is indicative of their body fat percentage. Other embodiments may include any number of body fat sensors provided in any number of suitable locations such as the employee's hands, chest, back, buttocks area and/or the like.

In some embodiments, body position sensors 712 are disposed at the employee's hands, feet, head, waist, and/or the like. For example, body position sensors 712 may include positioning devices 1020 integrated within the palm portion of work gloves 1008, integrated within work boots 1016, a belt 1022, a safety helmet 1024, elbow pads 1026, and/or knee pads 1028 worn by the employee. Such positioning devices 1020 may enable a determination of the absolute or relative positions of the employee's hands, feet, waist, head, knees and elbows. Other embodiments may include any number of locations sensors provided in any number of suitable locations such as the employee's torso/chest, back, shoulders, chin, buttocks area and/or the like.

In some embodiments, an audio sensor 714 is provided near the employee's mouth. For example, audio sensor 714 may include a microphone/speaker 1029 secured at or near of the employee's shirt collar. Other embodiments may include any number of audio sensor sensors provided in any number of suitable locations.

In some embodiments, a respiration sensor 716 is disposed at the employee's chest. For example, respiration sensor 716 may include a respiratory motion sensor 1030 secured around the employee's torso via the strap 1004. Other embodiments may include any number of respiration sensor sensors provided in any number of suitable locations.

In some embodiments, one or more neural sensors 718 are disposed about the employee's head/scalp. In some embodiments, a safety helmet 1024 includes a plurality of neural sensors 718 (e.g., sixteen neural sensors 718) integrated therein (e.g., coupled to an interior of helmet 1024 such that the contact the employee's head while the employee is wearing helmet 1024). Helmet 1024 may provide for positioning of neural sensors 718 in discrete neural sensor locations about the employee's head while helmet 1024 is being worn by the employee. Other embodiments may include any number of neural sensor sensors provided in any number of suitable locations.

In some embodiments, a heart rate sensor 720 is disposed about the employee's chest. For example, heart rate sensor 720 may include a heart rate monitor 1032 secured around the employee's torso/chest via strap 1004 and including two conductive contacts for sensing the employee's heart rate. Other embodiments may include any number of heart rate sensors provided in any number of suitable locations.

Employee 110 may also wear safety eyewear, such as glasses, safety glasses, safety goggles, a shield or the like). In some embodiments, the safety eyewear includes an AR display device 106. For example, in the illustrated embodiment, the eyewear includes goggles 300 having health information 204 (e.g., including health status summary 206 and health alert 208) projected thereon such that they are visible in the employee's FOV through goggles 300.

In some embodiments, some or all of the sensors 102 may be located throughout the employee's workstation 102 and surrounding workstation environment. For example, various ones of the sensors 102 may be located at or near the employee's desk, chair, computer, or the like.

Figure 11:
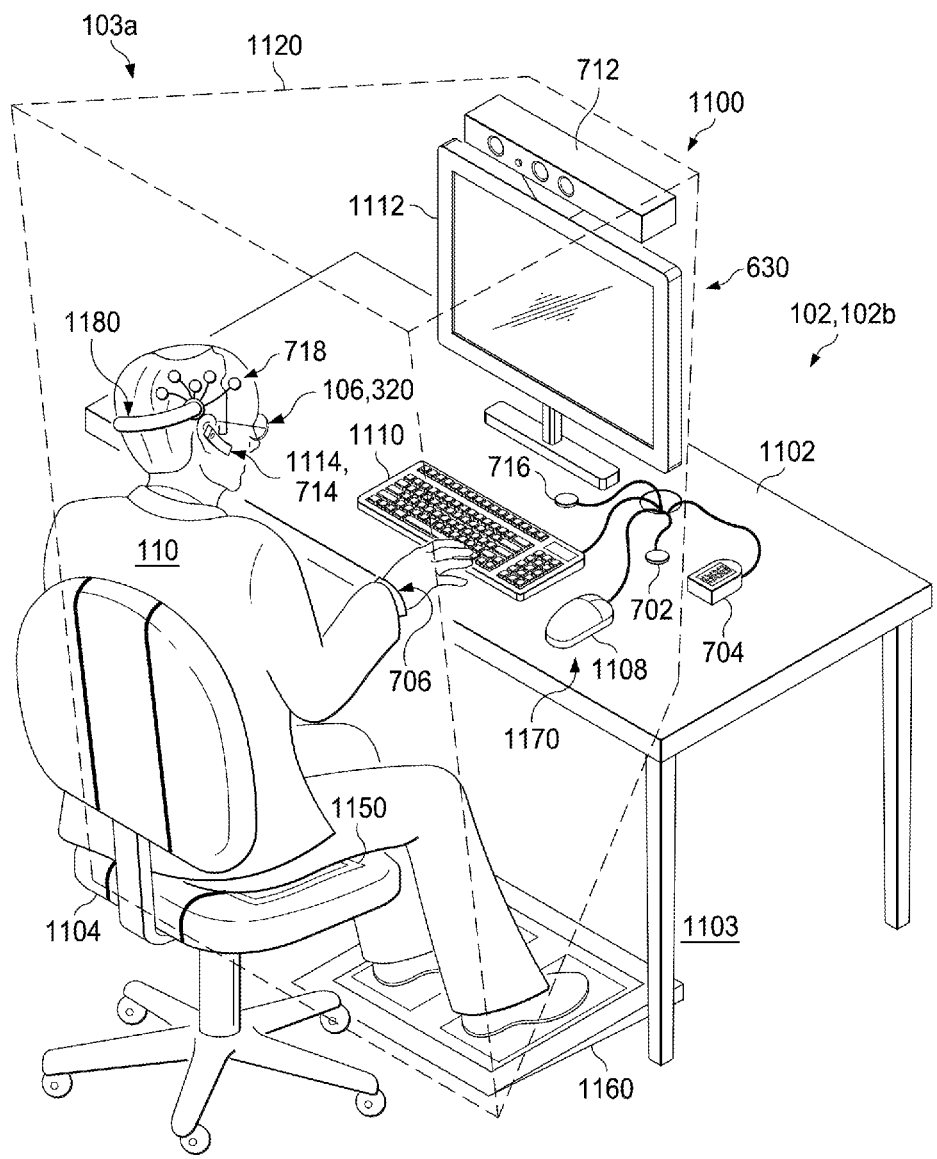
FIG. 11 is a diagram that illustrates an exemplary workstation environment in accordance with one or more embodiments of the present invention.

FIG. 11 is a diagram that illustrates an exemplary workstation environment 1100 in accordance with one or more embodiments of the present invention. In some embodiments, workstation environment 1100 includes a location at which employee 110 spends some or all of their work day (e.g., eight hours or more). For example, workstation environment 1100 may include the employee's office, the employee's cubicle, the employee's assigned station on an assembly/manufacturing line, or the like. In some embodiments, workstation environment 1100 includes employee workstation 603a. Workstation 603a may include devices, furniture and the like that facilitate the employee in accomplishing their work duties. For example, the workstation 603a may include a workstation surface 1102 (e.g., a desk), floor 1103, a chair 1104, and employee computer 630. In some embodiments, employee computer 630 may include various peripherals, such as a computer mouse ("mouse") 1108, a computer keyboard 1110, a computer display (e.g., computer monitor) 1112, an audio headset (e.g., a Bluetooth headset including a speaker and/or a microphone) 1114, or the like.

In some embodiments, the area around workstation 603a may define a workstation zone 1120. In some embodiments, workstation zone 1120 includes an area (e.g., a three-dimensional region) in which the employee typically resides during some or all of their workday. For example, as depicted by the dashed lines of FIG. 11, workstation zone 1120 may include the region immediately in front of computer display 1112 and including the location of the employee's chair 1104. As employee 110 may be expected to spend a great deal of time within zone 1120, the zone 1120 may be a region in which it is desirable to gather information (e.g., health data) relating to the employee's actions and general health while located therein. Workstation 603a may include one or more of sensors 102 (e.g., workstation sensors 102b) for acquiring health data relating to the employee's actions and general health while located in or near zone 1120. In some embodiments, various sensors 102 are integrated with areas/components of workstation 603a. For example, one or more temperature sensors 702, body fat sensors 710, force sensors 208, and/or the like may be integrated with chair 1104 (e.g., via a chair pad system ("chair pad") 1150 disposed on or integrated with the employee's chair 1104). As another example, one or more temperature sensors 702, body fat sensors 710, force sensors 208, and/or the like may be integrated with floor 1103 underfoot of the employee (e.g., via a floor mat system ("floor pad") 460 disposed on or integrated with floor 1103 of workstation environment 603a). As yet another example, one or more temperature sensors 702, blood condition sensors 704, blood pressure sensors 706 and/or the like may be integrated with mouse 1108 or other peripheral devices of employee computer 630 (e.g., via a mouse system 1170). As another example, one or more neural sensors 718 may be integrated into a neuro-headset system ("neuro-headset") 1180 worn on the head of the employee. In some embodiments, neural sensors 718 may include dry electrodes that can be used to sense neuro signals. Such dry electrodes may require minimal or no skin preparation for disposing the electrode contact on the employee's scalp. As described herein, neural sensor 218 maybe provided via a headset and/or in various surfaces that contact/support the employee's head, such as a headrest of a chair/seat. FIG. 5 is a is a block diagram that illustrates a workstation 102 including integrated sensors 102 in accordance with one or more embodiments of the present invention. Such an integration of sensors 102 within the workstation environment may help to reduce the physical profile of sensors 102, reduce distractions to employee 110 that may otherwise be caused by the presence of sensors 102 and/or enhance the ease of use to the employee 110 by allowing health data 700 to be acquired while the employee is engaging in their day-to-day work duties. For example, sensors 102 may be able to passively acquire health data 700 without requiring the employee to take special efforts to engage in a health test.

Employee 110 may also wear eyewear, such as glasses, safety glasses, safety goggles, a face shield or the like). In some embodiments, the eyewear includes an AR display device 106. For example, in the illustrated embodiment, the eyewear includes eyeglasses 321 having health information 204 (e.g., including health status summary 206 and health alert 208) projected on a lenses thereof such that they are visible in the employee's FOV through glasses 320.

Figure 12:
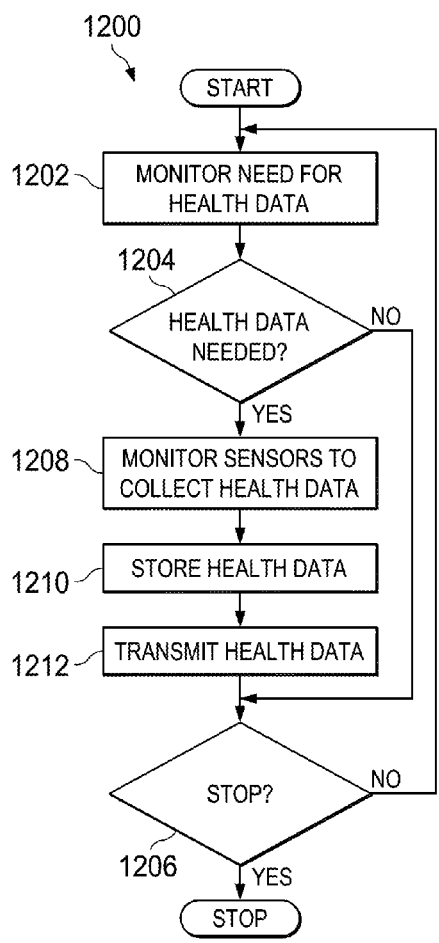
FIG. 12 is a flowchart that illustrates a method of collecting health data in accordance with one or more embodiments of the present invention.

FIG. 12 is a flowchart that illustrates a method 1200 of collecting health data 700 (temperature data 700a, blood condition data 700b, blood pressure data 700c, force data 700d, body fat data 700e, body position data 700f, audio data 700g, respiration data 700h, neural data 700i and/or heart rate data 700j) in accordance with one or more embodiments of the present invention. Method 1200 may be executed by mobile device 622 and/or employee computer 630 to provide for collecting health data 700 by the mobile device 122 and/or employee computer 630.

Method 1200 may include monitoring the need for health data 700, as depicted at block 1202. In some embodiments, monitoring the need for health data may include determining whether or not there is a need to collect health data 700 from one or more of the sensors 102. In some embodiments, the need for health data 700 is identified based on a request from another component of system 600. For example, mobile device 622 and/or employee computer 630 may determine that there is a need to collect health data 700 in response to a request for health data (e.g., a request to initiate a health test and/or a query for the health data 700) received from server 604 and/or the employee 110 (e.g., via a user request to start a health test).

In some embodiments, the need for health data 700 is identified based on a corresponding health monitoring test schedule/routine. For example, where a health test schedule requires collection of health data 700 at 12:00 pm, it may be determined that health data 700 is needed if the current time is 12:00 pm. As another example, where a health test schedule requires the continuous collection of a batch of health data 700 from 8:00 am-6:00 pm, it may be determined that health data 700 is needed if the current time is in the range of 8:00 am-6:00 pm. As yet another example, where a health test schedule requires the repeated collection of health data 700 at an hourly interval from 8:00 am-6:00 pm, it may be determined that health data 700 is needed if the current time is 8:00 am, 9:00 am, and so forth. It will be appreciated that these test schedules are exemplary, and other embodiments may include any suitable test schedule.

Where it is determined that health data 700 is not needed, at block 1204, method 1200 may include proceeding to determining whether or not the routine should be stopped, as depicted at block 1206. In some embodiments, it may be determined that the test routine should be stopped based on an instruction to stop from another device of system 600. For example, mobile device 622 and/or employee computer 630 may determine that they should stop execution of the health monitoring test routine in response to an instruction from server 604 and/or the employee 110 to stop the health test routine (e.g., an employee request to terminate the health test submitted via an interactive health monitoring dashboard as discussed in more detail below). Where it is determined that the execution of the health monitoring test routine should be stopped, the health test routine may be stopped.

Where it is determined that health data 700 is needed, at block 1204, method 1200 may include proceeding to monitoring of sensors 102 to collect health data 700, as depicted at block 1208. In some embodiments, monitoring sensors 102 to collect health data 700 includes monitoring the particular sensors 102 that provide the particular health data 700 needed. For example, where the heath data 700 needed includes the employee's body temperature, monitoring sensors 102 to collect health data 700 may include, mobile device 622 and/or employee computer 630 monitoring one or more of temperature sensors 202 (e.g., the thermometer/thermocouple 1002) to collect corresponding temperature measurements (e.g., temperature data 700*a*). Similar techniques may be employed for collecting other forms of health data 700 from the various sensors 102 (e.g., mobile sensors 102*a* and/or workstation sensors 102*b*) of system 600. For example, mobile device 622 and/or employee computer 630 may collect temperature data 700*a*, blood condition data 700*b*, blood pressure data 700*c*, force data 700*d*, body fat data 700*e*, body position data 700*f*, audio data 700*g*, respiration data 700*h*, neural data 700*i* and/or heart rate data 700*j*, from the corresponding one or more temperature sensors 702, one or more blood condition sensors 704, one or more blood pressure sensors 706, one or more force sensors 708, one or more body fat sensors 710, one or more body position sensors 712, one or more audio sensors 714, one or more respiration sensors 716, one or more neural sensors 718, and/or one or more heart rate sensors 720 of health monitoring system 600, in a similar manner.

Method 1200 may include storing health data 700, as depicted at block 1210. In some embodiments, storing health data 700 may include storing the collected health data 700 in local or remote memory. For example, mobile device 622 and/or employee computer 630 may store the collected health data 700 in local memory 801 and/or 900. In some embodiments, storing heath data 700 may include buffering/queuing health data 700 for transmission at a later time.

Method 1200 may include transmitting health data 700, as depicted at block 1212. In some embodiments, transmitting health data 700 may include transmitting health data 700 to another component/entity of system 600. For example, mobile device 622 may transmit health data 700 (e.g., health data 700 stored in memory 801 and/or 900) to server 604 for use in monitoring the health of the employee 110. In some embodiments, health data 700 may be transmitted from mobile device 622 and/or employee computer 630 to server 604 via network 618.

In some embodiments, the transmission of health data 700 may be regulated based on a corresponding schedule for sending/transmitting health data. For example, where a health test routine requires collection of health data at 12:00 pm, health data 700 may be collected and transmitted at or about 12:00 pm. As further example, where a health test routine requires the continuous collection and transmission of health data from 8:00 am-6:00 pm, health data 700 may be collected and transmitted from 8:00 am-6:00 pm such that a substantially continuous stream of health data 700 is transmitted (e.g., from sensors 102 to mobile device 622 and/or employee computer 630, and/or from mobile device 622 and/or employee computer 630 to server 604) for use in monitoring the employee's health. As a further example, where a health test schedule requires the continuous collection of health data from 8:00 am-6:00 pm and the transmission of health data in batches at hourly intervals, health data 700 may be collected and stored from 8:00 am-6:00 pm, with batches of health data 700 for each preceding hour transmitted at or about 9:00 am, 10:00 am and so forth.

In some embodiments, after transmitting the health data collected, method 1200 may progress to block 1206 to determine whether or not the acquisition of health data should continue. Accordingly, mobile device 622 and/or employee computer 630 may collect health data 700 from the various sensors 102 as required for use in monitoring the health of employees.

It will be appreciated that the method 1200 is an exemplary embodiment of methods that may be employed in accordance with techniques described herein. The method 1200 may be may be modified to facilitate variations of its implementations and uses. The method 1200 may be implemented in software, hardware, or a combination thereof. Some or all of the method 1200 may be implemented by one or more of the modules/applications described herein, such as mobile device module 808 and/or employee computer module 908. The order of method 1200 may be changed, and various elements may be added, reordered, combined, omitted, modified, etc.

Server 604 (see FIG. 6) may include a network entity that serves requests by other network entities as will be understood by those skilled in the art. For example, sever 604 may serve request by client entities, such as mobile device 622, employee computer 630, employer workstation 603b, and/or the like via network 618. Server 604 may host a content site, such as a website, a file transfer protocol (FTP) site, an Internet search website or other source of network content. In some embodiments, server 604 hosts one or more applications, such an employee health monitoring application. Some or all of the employee health monitoring application may be executed locally on server 604 and/or remotely by various other network entities, such as mobile device 622, employee computer 630, employer workstation 603b, remote workstations 612, and/or the like. For example, server 604 may cause the execution of remote applications/processes (e.g., an application executing the method 1200) on mobile device 622 and/or employee computer 630 to collect health data 700 from the employee, execute a local application (e.g., a health monitoring application) to conduct processing of the collected health data 700 for use in monitoring the employee's health and serving health content (e.g., a health report) for display on mobile device 622, employee computer 630, employer workstation 603b, remote workstations 612, and/or the like.

File server 606 may be employed by the system to manage employee health information 609 as will be understood by those skilled in the art. For example, file server 606 may manage access to database 608 by the other network entities, including server 604. File server 606 may execute a database management system, e.g. a set of software programs that controls the organization, storage, management, and retrieval of data in database 608, such as health information 609. Database 608 may include an employee information database. For example, database 608 may store employee health information 609 and/or an employee access information (e.g., user credential data and permissions data) that can be used to verifying user's right to access various features of system 600 and/or health information 609. File server 606 and/or database 609 may include network attached storage ("NAS"), storage area networks ("SAN"), or direct access storage ("DAS"), or any combination thereof. In some embodiments, a database server can be used to store database 608 instead of or in addition to file server 606.

Mobile device 622, employee computer 630, employer workstation 603b, remote workstations 612 may include personal computers (PC) as is known in the art. The computers may run UNIX, Linux, Windows®, or some other operating system compatible with the networked systems discussed herein. In some embodiments, mobile device 622, employee computer 630, employer workstation 603b, remote workstations 612 may include remote terminals that enable a user to interact with various processes being controlled by server 604. For example, the operations described herein with regard to mobile device 622 and/or employee computer 630 may be executed by server 604, and the mobile device 122, the employee computer 126, the employer workstation 603b, and/or the remote workstations 112 may include network terminals that provide for user interaction with the operations provided by server 604. Moreover, mobile device 622, employee computer 630, employer workstation 603b, remote workstations 612 may provide access to computer program instructions stored on server 604. For example, a health monitoring application running on server 604 may be accessible via Mobile device 622, employee computer 630, employer workstation 603b, remote workstations 612 such that the employee may provide access credentials to login to their account, server 604 may verify their credentials/permissions, and the employee may be able to enter/edit their health information 609 via mobile device 622, employee computer 630, employer workstation 603b, remote workstations 612. Health information provided via Mobile device 622, employee computer 630, employer workstation 603b, remote workstations 612 can be forwarded via server 604 to file server 606 for use in updating the employee's health information 609 stored in database 608. In some embodiments, Mobile device 622, employee computer 630, employer workstation 603b, remote workstations 612 can interface with different servers (e.g., web or network servers 604, 606 or 610) for accessing health information 609 via communications network 618.

Employer workstation 603b may provide an employer (e.g., the employee's manager, the employee's human resources manager, or the like) access to employee health information 609 for one or more employees. For example, the employer may be provided regular reports and/or alerts regarding the health of some or all of their employees, may proactively initiate review of employee health information 609 for some or all of their employees, and/or initiate health test for some or all of their employees via employer workstations 603b. In some embodiments, the employer may access such features via an interactive dashboard displayed to the employer. Thus, for example, an employer may determine whether a health condition is affecting a given employee, determine whether or not an employee is following their health plan, determine whether some or all employees of a group (e.g., at a certain facility) are experiencing similar symptoms indicative of a group wide health concern (e.g., a high percentage of employees at a given facility have developed asthma, chronic obstructive pulmonary disease ("COPD"), or other chronic condition) via an interactive health dashboard.

Figure 13:
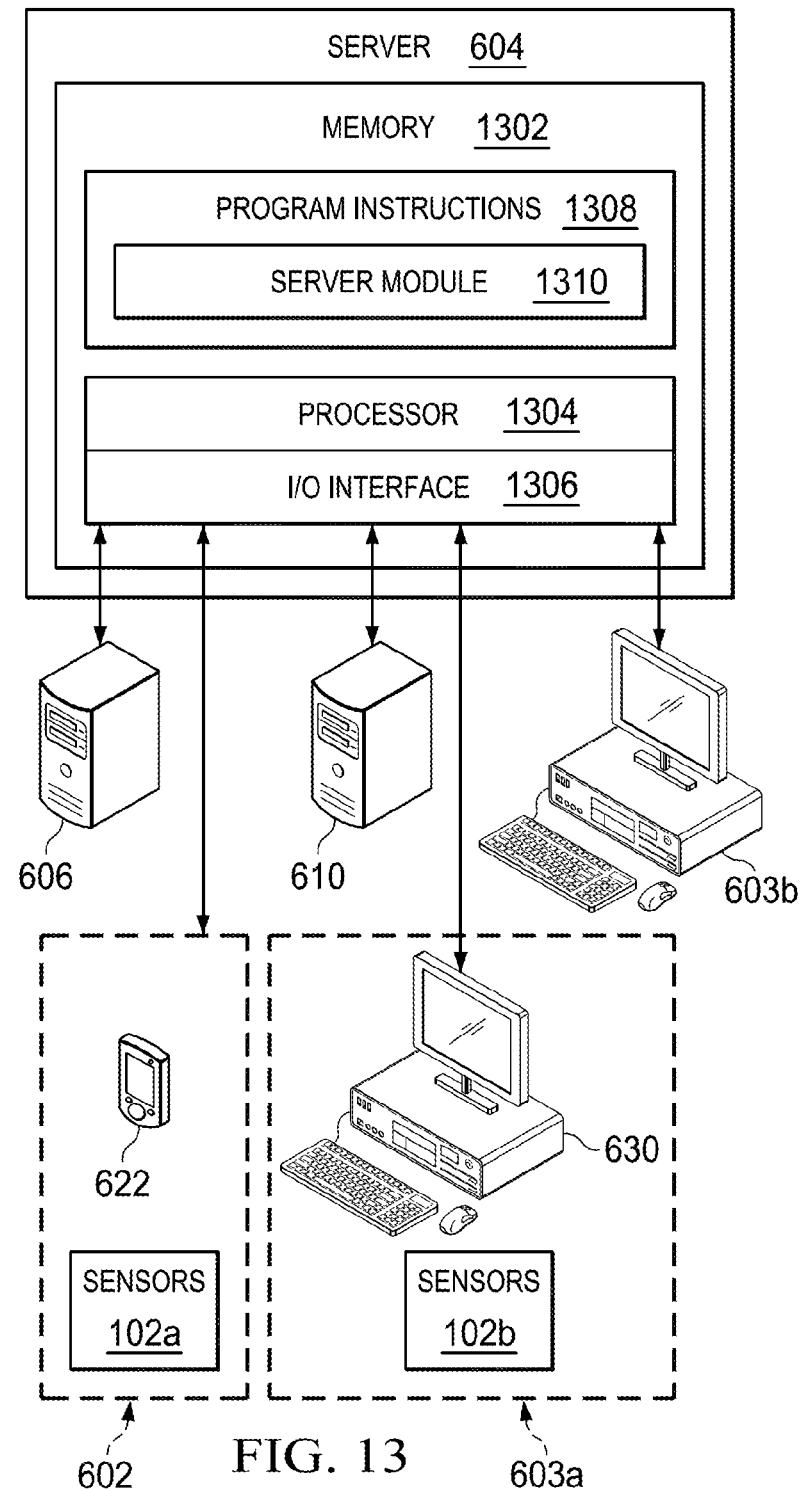
FIG. 13 is a block diagram illustrating components of a server in accordance with one or more embodiments of the present invention.

FIG. 13 is a block diagram illustrating components of server 604 in accordance with one or more embodiments of the present invention. In some embodiments, server 604 includes a memory 1302, a processor 1304 and an input/output (I/O) interface 1306.

Memory 1302 may include non-volatile memory (e.g., flash memory, ROM, PROM, EPROM, EEPROM memory), volatile memory (e.g., random access memory (RAM), static random access memory (SRAM), synchronous dynamic RAM (SDRAM)), bulk storage memory (e.g., CD-ROM and/or DVD-ROM, hard-drives), or the like. Memory 1302 may include a non-transitory computer readable storage medium having program instructions 1308 stored thereon that are executable by a computer processor (e.g., processor 1304) to cause the functional operations described herein with regard to server 604. Program instructions 1308 may include a server module 1310 including program instructions that are executable by processor 1304 to provide some or all of the functionality described herein with regard to server 604.

Processor 1304 may be any suitable processor capable of executing/performing program instructions. Processor 1304 may include a central processing unit (CPU) that carries out program instructions (e.g., of server module 1310) to perform arithmetical, logical, input/output and other operations of server 604. Processor 1304 can be any commercially available processor, or plurality of processors, adapted for use in server 604, such as Intel® Xeon® multicore processors manufactured by Intel Corporation, Intel® micro-architecture Nehalem manufactured by Intel Corporation, AMD Opteron™ multicore processors manufactured by AMD Corporation, or the like. As one skilled in the art will appreciate, processor 1304 may also include components that allow server 604 to be connected to peripherals (e.g., a display and keyboard that would allow direct access to the processor and the memory 1302, and/or application executing via server 604).

I/O interface 1306 may provide an interface for connection of one or more I/O devices to server 604. The I/O devices may include other network devices, such as the file server 606, web server 610, mobile device 622, employee workstation 603a (e.g., computer 630), employer workstation 603b, sensors 102, and/or the like. The I/O devices may be communicatively coupled to the I/O interface 1306 via a wired or wireless connection.

Figure 14:
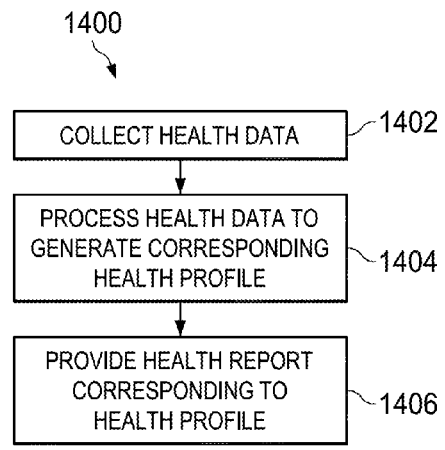
FIG. 14 is a flowchart that illustrates a method of monitoring an employee's health in accordance with one or more embodiments of the present invention.

In some embodiments, server 604 uses the collected health data 700 to monitor the employee's health. FIG. 14 is a flowchart that illustrates a method 1400 of monitoring the employee's health in accordance with one or more embodiments of the present invention.

Figure 15:
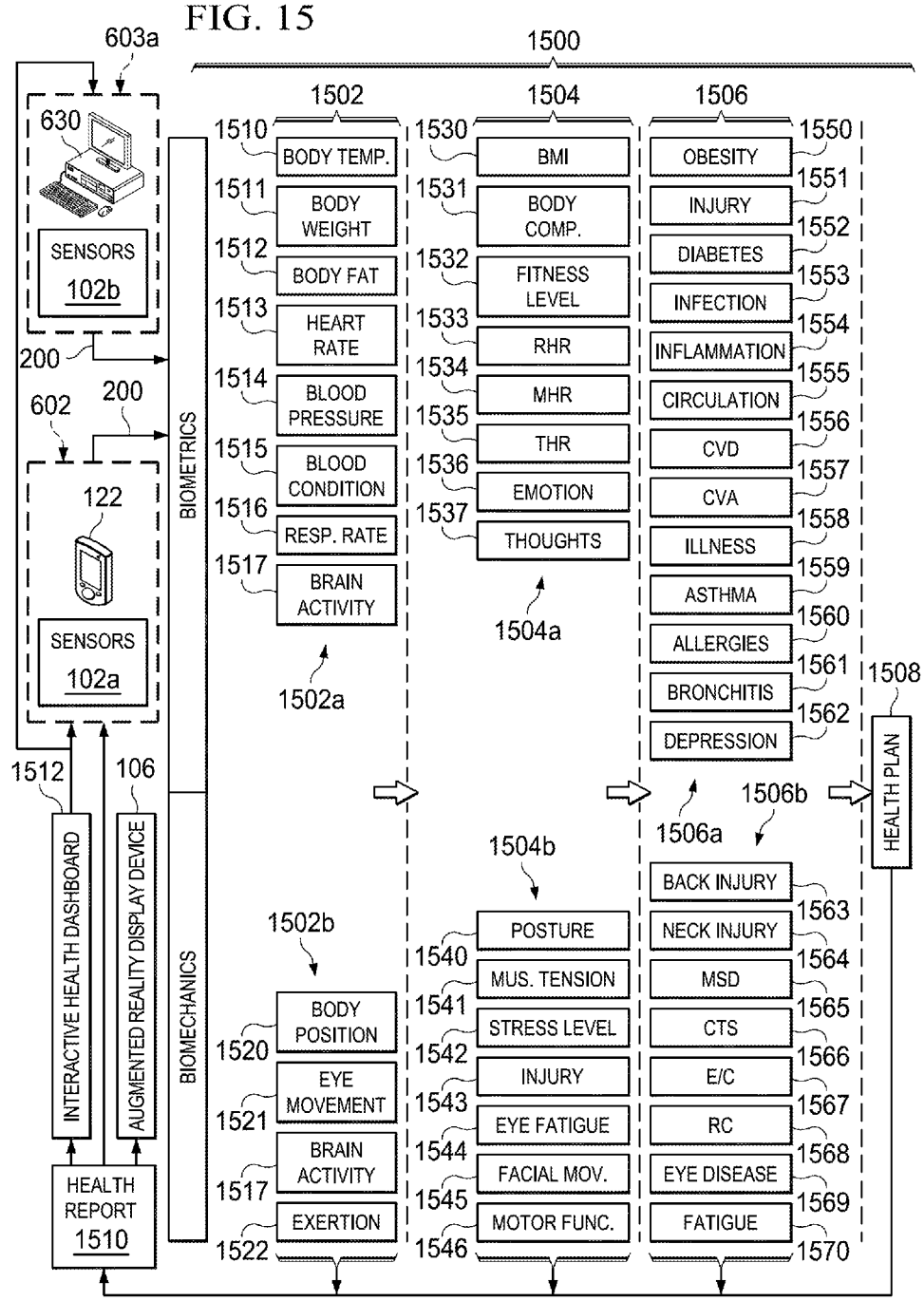
FIG. 15 is a block diagram illustrating dataflow within a health monitoring system in accordance with one or more embodiments of the present invention.

Method 1400 may include collecting health data 700, as depicted at block 1402. In some embodiments, collecting health data may include collecting health data 700 from other entities of system 100. For example, server 604 may collect health data 700 (e.g., temperature data 700a, blood condition data 700b, blood pressure data 700c, force data 700d, body fat data 700e, body position data 700f, audio data 700g, respiration data 700h, neural data 700i and/or heart rate data 700j) for the employee via the various sensors 102 (e.g., via mobile sensors 102a and/or mobile device 622 of the mobile health monitoring system 102 and/or workstation sensors 102b and/or employee computer 630 of workstation 103a) (See FIG. 15 including a block diagram illustrating dataflow within system 600 in accordance with one or more embodiments of the present invention).

In some embodiments, monitoring the health sensors to collect health data includes executing a single measurement by some or all of the sensors 102. For example, some or all of the sensors 102 may be employed to record a single measurement in sequence (e.g., one after the other) or in parallel (e.g., at the same time) and transmit corresponding health data 700 to mobile device 622 and/or employee computer 630. As described herein, mobile device 622 and/or employee computer 630 may collect the measurements from sensors 102 and transmit corresponding health data 700 to server 604 for use in monitoring the employee's health.

In some embodiments, monitoring the health sensors to collect health data includes executing multiple measurements by some or all of sensors 102. For example, some or all of sensors 102 may be employed to record a set of measurements (e.g., one per minute) over a given period of time (e.g., 5 minutes, 1 hour, 8 hours, or the like) and transmit corresponding health data 700 to mobile device 622 and/or employee computer 630. As described herein, the mobile device 622 and/or employee computer 630 may collect the measurements from sensors 102 and transmit corresponding health data 700 to server 604 for use in monitoring the employee's health.

In some embodiments, the health data is collected via health test that are initiated by server 604. For example, server 604 may execute a health monitoring routine that requires health data to be collected according to a given test schedule/routine (e.g., health data to be sensed/collected from 8 am-6 pm, health data to be sensed/collected hourly from 8 am to 6 pm, and/or the like), server 604 may determine that health data 700 is required based on the schedule, and, in response to determining that health data 700 is required, server 604 may query mobile device 622, employee computer 630 and/or sensors 102 for health data 700 according to the schedule. Where a test schedule/routine requires collection of health data from 8 am to 6 pm, server 604 may send, to mobile device 622 and/or employee computer 630 at 8 am, a first request to initiate collection and forwarding of health data 700 to server 604, and send, to mobile device 622 and/or employee computer 630 at 6 pm, a second request to terminate collection and forwarding of health data 700 to server 604. In such an embodiment, mobile device 622 and/or employee computer 630 may continually acquire and forward health data 700 to server 604 from 8 am to 6 pm. Server 604 may transmit similar requests in accordance with any suitable test schedule/routine. For example, where a test schedule/routine requires collection of health data hourly from 8 am to 6 pm, server 604 may send, to mobile device 622 and/or employee computer 630 at each of 8 am, 9 am, 10 am, and so forth, a request to collect and forward health data 700 to server 604. In such an embodiment, mobile device 622 and/or employee computer 630 may collect and forward a set of health data 700 to server 604 each hour from 8 am to 6 pm (e.g. at 8 am, 9 am, 10 am, and so forth).

In some embodiments, server 604 initiates a health test based on an external request/event, such as a request generated by a user. For example, where an employee or an employer is interacting with an interactive health dashboard for a given employee that enables the user to request to run an health test and the user requests to run a health test, server 604 may determine that health data is required based on the request and, in response to determining that health data is required, server 604 may query mobile device 622 and/or employee computer 630 for the health data. In such an embodiment, mobile device 622 and/or employee computer 630 may collect and forward a set of health data 700 to server 604 at or near the time of the user's request to conduct a health test. Thus, server 604 may initiate health test automatically (e.g., based on a test schedule/routine) and/or in response to external request (e.g., a user initiated request from an employee, an employer, or other user).

In some embodiments, the health data for one or more employees may be logged over time. For example, health data 700 may be collected for each employee of a group of employees, and health information 609 for each of the employees may be updated to reflect the health data collected. Thus, a log of health data for each of the employees may be generated. In some embodiment, the log of health data for a given employee may be used to generate a profile for the employee. For example, the logged health data 700 may be used to generate health profiles and/or reports that are based on current/recent health data 700 (e.g., health data 700 collected within a minute, hour, day, week, month, or the like) and/or historical health data 700 (e.g., health data 700 collected more than a minute, hour, day, week, moth, year, or the like prior). In some embodiments, health information 609 for the employee includes a record/log of the employee's health information. For example, health information 609 may include, for each employee, employee personal profile data (e.g., name, age, etc.), historical/current employee health profile data (e.g., health data, characteristics, conditions, plans) and/or employee activity data (e.g., a log of exercises, food consumed, etc.), and so forth.

Method 1400 may include processing the collected health data to generate one or more corresponding health profiles 1500 (See FIG. 15), as depicted at block 1404. In some embodiments, health profile 1500 is generated by server 604 based on the processing of the collected health data 700. Health profile 1500 may include health characteristics 1502, health conditions 1504, health risks 1506, and/or health plans 1508 for the employee.

In some embodiments, health characteristics 1502 include a first level of health profile data that is derived from the collected health data 700. For example, server 604 may process the collected health data 700 (e.g., biometric health data and/or biometric health data) to identify various biometric health characteristics 1502a and/or biomechanic health characteristics 1502b for the employee. Biometric health characteristics 1502a may include, for example, the employee's sensed body temperature 1510, body weight 1511, body fat 1512, heart rate 1513, blood pressure 1514, blood condition (e.g., blood oxygenation, blood glucose level, etc.) 1515, respiration rate 1516, neural/brain activity 1517, and/or the like. Biomechanic health characteristics 1502b may include, for example, the employee's sensed body position 1520 (e.g., the employee's physical positioning and/or movement of the employee's head, torso, arms, hands, legs, feet, and/or the like), eye movement (e.g., focal point, blink rate, pupil dilation of the eye, and/or the like) 1521, neural/brain activity 1517, physical exertion 1522, and/or the like.

In some embodiments, the health characteristics 1502 may be provided directly via health data 700. For example, heart rate data 700i may include a determined value for heart rate (e.g., 80 beats per minute ("BPM"). A similar value may be provided for some or all of the other health characteristics 1502. In some embodiments, health characteristics 1502 may be extrapolated/calculated from health data 700. For example, health data 700 may include a set of measurement indicative of heart beats over a period of time (e.g., a log of blood pressure data 700c indicative of twenty heart beats over fifteen seconds) and server 604 may process the set of measurement to determine the corresponding hear rate value (e.g., a heart rate of 80 BPM). A similar determination may be made for some or all of the other health characteristics 1502. For example, health data 700 may be received and/or processed in a similar manner to determine values for some or all the other health characteristics 1502 (e.g., based on received values, data sets, and/or the like).

In some embodiments, body weight 1511 is based on the force data 700d collected via one or more force sensors 208. Force data 700d indicative of the forces sensed by the force transducers 1014 may be used to determine the employee's weight. For example, where the right and left force transducers 1014 in the employee's boots 1016 each sense a force of about 23 kg (62 lbs.) the forces may be added together to determine a body weight for the employee of about 56.5 kg (124.6 lbs.). As a further example, where force transducers 1014 in the employee's chair 1104, located in chair pad 1150 and/or floor mat 1160 sense forces totaling about 56.5 kg (124.6 lbs.), the forces may be used to determine a body weight for the employee of about 56.5 kg (124.6 lbs.).

In some embodiments, body fat 1512 is based on body fat data 700e collected via one or more body fat sensors 710. For example, the body fat 1512 may be determined using bioelectrical impedance analysis (BIA) of the impedance/resistance sensed by the body fat sensor 710. Ideally, male employees will have a body fat measurement of about 8-17% and female employees will have a measurement between about 10-21%. The body fat 1512 may include a body fat percentage which is determined as the total weight of the person's fat divided by the person's weight.

In some embodiments, heart rate 1513 is based on heart rate data 700j collected via one or more heart rate sensors 720. For example, heart rate 1513 may be determined using the number of heart beats sensed over a given period of time, typically sixty seconds. In some embodiments, heart rate 1513 is based on blood pressure data 700c collected via one or more of the blood pressure sensors 706. For example, heart rate 1513 may be determined using the rate of pulsations of blood pressure which may correspond to the heart rate.

In some embodiments, blood pressure 1514 is based on blood pressure data 700c collected via one or more blood pressure sensors 706. Blood pressure 1514 may be determined using blood pressure data 700c which is indicative of pressure pulsations due to blood flow. For example, blood pressure 1514 may be determined based on a maximum blood pressure detected (e.g., the "systolic" blood pressure) and the minimum blood pressure detected (e.g., the "diastolic" blood pressure) via a blood pressure cuff. Blood pressure 1514 may be recorded as the systolic blood pressure over the diastolic blood pressure (e.g., 90/60 mmHg).

In some embodiments, blood condition 1515 is based on blood condition data 700b collected via one or more of blood condition sensors 704. For example, the blood oxygenation, blood glucose level, and/or the like may be determined from blood condition data 700b provided by a pulse oximeter or similar blood conditions sensor.

In some embodiments, respiratory rate 1516 is based on respiration data 700h collected via one or more respiration sensors 716. For example, the respiration rate may be determined based on a number of employee breaths sensed by respiration sensor 716 over a given period of time. For example, where respiration data 700h indicates that the employee has taken four breaths in fifteen seconds, the employees respiration rate 1516 may be determined as sixteen breaths per minute ($V_f$).

In some embodiments, brain activity 1517 is based on neural data 700i collected via one or more neural sensors 718. In some embodiments, brain activity 1517 includes a log of neuro-signals (e.g., including alpha, beta, gamma, and delta waves) that are indicative of the employee's brain state, including the employee's emotional state, thoughts (e.g., cognitive thoughts, subconscious thoughts, and intent), facial movements (e.g., facial expressions), motor functions and/or the like. Brain activity 1517 may include or otherwise be extrapolated from the neural data 700i. Brain activity 1517 may be both of biometric and biomechanic characteristics based at least on its use in determining various biometric and biomechanic health profile data (e.g., various biometric and biomechanic conditions and risks).

In some embodiments, body position 1520 is based on body position data 700f collected via one or more body position sensors 712. For example, the body position data 700f collected from a camera and/or the positioning devices may be used to determine the relative and/or absolute position of the employee's head, torso, arms, elbows, hands, legs, knees, feet, waist and/or the like. In some embodiments, the employee's body position 1520 is determined using body position data 700f. In some embodiments, the employee's body position is determined based on forces sensed by various ones of the force sensors 708. For example, it may be determined that the employee is standing when a force approximately equal to the employee's body weight is sensed by the force transducers 1014 and/or force transducers in floor mat 1160.

In some embodiments, physical exertion 1522 is based on force data 700d collected via one or more of the force sensors 708. For example, the force data 700d indicative of the forces sensed by the force transducers 1014 integrated into the employee's gloves and/or boots may be used to determine a physical exertion by the employee to lift/move an object.

In some embodiments, one or more of health characteristics 1502 may be used to determine one or more health conditions 1504. Health conditions 1504 may include a second level of health profile data that is derived from the one or more health characteristics 1502 and/or collected health data 700. For example, server 604 may process the health characteristics 1502 and/or the collected health data 700 to extrapolate various biometric health conditions 1504a and/or biomechanic health conditions 1504b for the employee. Biometric health conditions 1504a may include, for example, a body mass index ("BMI") 1530, a body composition 1531, a fitness level 1532, a resting heart rate ("RHR") 1533, a maximum heart rate ("MHR") 1534, a target heart rate ("THR") 1535, emotions 1536, thoughts 1537, and/or the like for the employee. Biomechanic health conditions 1504b may include, for example, posture ("posture analysis") 1540, muscle tension 1541, a stress level 1542, a physical injury 1543, an eye fatigue level 1544, facial movements 1545, motor functions (e.g., gestures) 1546, and/or the like for the employee.

In some embodiments a health condition 1504 may be determined based on one or more health characteristics 1502 and/or other data (e.g., the employee's personal profile). For example, BMI 1530 and/or body composition 1531 may be extrapolated from body weight 1511 and body fat 1512. Fitness level 1532 may be based on weight 1511, heart rate 1513, and/or blood pressure 1514. Resting heart rate 1533, maximum heart rate 1534, and/or target heart rate 1535 may be based on the heart rate 1513 and/or the employee's age. Emotions 1536 and/or thoughts 1537 may be based on the employee's brain activity 1517. Posture 1540 and muscle tension 1541 may be based on the observed body position 1520 of the employee (e.g., physical positioning and movement of the head, torso, arms, hands, legs, feet, and/or the like) and/or physical exertion 1522. Stress level 1541 may be based on the observed body position 1520, eye movement 1521 and/or brain activity 1517 for the employee. Physical injury 1543 may be based on the observed body position 1520, eye movement 1521, brain activity 1517 and/or physical exertion 1522 for the employee. Eye fatigue 1544 may be based on the observed eye movement 1521 of the employee. Facial movements 1545 and/or motor functions 1546 may be determined based on brain activity 1517.

BMI 1530 may be the individual's body mass (m) divided by the square of their height (h). In some embodiments, BMI 1530 is determined using the following equation:

$$BMI = m*703/h^2 \qquad (1)$$

Where "m" is the employee's mass (in kg. or lbs.) and "h" is the employee's height (in meters or inches). From this equation, server 604 can determine whether the employee is of average weight (e.g., having a BMI in the range of about 18.5-25), overweight (e.g., having a BMI in the range of about 25-30), or obese (e.g., having a BMI over about 30).

Body composition 1531 may indicate a percentage of bone, fat and/or muscle in the employee's body. In some embodiments, body composition 1531 is determined based at least on the body fat percentage and the body weight 1511.

In some embodiments, fitness level 1532 is indicative of the employee's body's ability to withstand a physical workload and/or recover in a timely manner. Fitness level 1532 may be based on the employee's heart rate. For example, an employee may be determined to have a good fitness level if their resting heart rate 1534 is under about 100 BPM.

In some embodiments, respiratory rate 1516 is indicative of the number of breaths taken within a set amount of time (e.g., 60 seconds). In some embodiments, resting heart rate (RHR) 1533 is the measured heart rate (HR) 1513 taken at a period of low activity by the employee (e.g., while seated in chair 1104 and not engaging in any strenuous work activities). The maximum heart rate (MHR) 1534 may be determined using the following equation:

$$MHR = 205.8 - (0.685 \times age) \qquad (2)$$

Where "age" is the age of the employee in years. Target heart rate (THR) 1535 may be calculated using the following formula, the "Karvonen method":

$$THR = ((MHR - RHR) \times \%intensity) + RHR \qquad (3)$$

Where intensity is a percentage, typically about 65%-85%. Target heart rate 1535, resting heart rate 1533 and maximum heart rate 1534 may be provided to the employee to aid the employee in safe exercise regimens, the formulation of a health plan, and the determination of whether the employee has met its health plan goals for the day, e.g., whether the employee has reached their target heart rate 1535 by the distance and length of time the employee has indicated to the program it has exercised. Also, if the employee's resting heart rate 1533 is above 100 beats per minute, for example, the system may provide the employee with a health alert/warning regarding the risks for cardiovascular disease, stroke, or obesity via health dashboard 1512, the health report 1510, AR display 106, and/or the like.

In some embodiments, the employee's emotions 1536, thoughts 1537, facial movements 1545 and/or motor functions 1546 may be determined based on the sensed neuro signals (e.g., brain activity 1517). For example, a plurality of predetermined brain wave patterns may be associated with corresponding emotions, thoughts, facial movements and/or motor functions. During processing of brain activity 1517, the sensed/observed neuro signals may be compared to the plurality of predetermined neural signal patterns to identify a match there between. Upon matching the observed neuro signals to one or more of the predetermined neural signal patterns, it may be determined that the employee is engaged in emotions (e.g., happy, sad, excited, depressed, etc.) 1536, thoughts (e.g., intent to take an action, etc.) 1537, facial movements (e.g., facial gestures such as smiling) 1545 and/or motor functions (e.g., a sequence of movements) 1546 that correspond to the matching predetermined neural signal pattern. In some embodiments, as described herein, an animated avatar may be used to mimic the employee's current emotional state and/or facial gesture. For example, when it is determined that the employee is happy and/or smiling, a displayed avatar can be animated to smile, providing the employee or other persons reviewing the employee's health (e.g., the employer) with an indication of the employee's current emotional state and/or facial expression. In some embodiments, the ability to determine the employee's thoughts may be employed to assist the employee with completing their work duties. For example, where system 600 is able to determine that the employee intends to open a word processing application on mobile device 622 and/or employee computer 630, the system 600 may launch the word processing application on mobile device 622 and/or employee computer 630 based on the determined intent to act, without any physical interaction by the employee. In some embodiments, the brain activity 1517 and/or thoughts 1537 may be used to predict an action that may be taken by the employee. For example, where the employ has the thought of "lift the heavy box", it may be determined that the employee is about to lift a heavy box.

In some embodiments, a determination of the employee's posture (e.g., be proper ergonomic position) 1540 may be based on body position 1520. For example, the employee may be determined to have good posture that where one or more of the employee's hands, wrists, and forearms are straight, in-line and roughly parallel to the floor; the employee's head is level, or bent slightly forward, forward facing, and balanced, and generally in-line with the torso; the employee's shoulders are relaxed and its upper arms hang normally at the side of the body; the employee's elbows stay in close to the body and are bent at angles between about 90 and 102 degrees; the employee's feet are fully supported by the floor or a footrest (if the employee's desk height is not adjustable); the employee's back is fully supported when sitting vertical or leaning back slightly; the employee's thighs and hips are generally parallel to the floor; and/or the employee's knees are about the same height as the hips with the feet slightly forward. Posture 1540 may include a determination of the proper alignment of the head, torso, arms, and feet when the employee is standing/sitting and the employee's deviation from the proper alignment based on the observed body position 1520. In some embodiments, the actual body position of the employee, relative to the ideal body position may be determined and posture 1540 may indicate, a percentage deviation of the actual body position to the ideal body position and/or may include suggestions for improving the employee's posture (e.g., sit up in chair with lower back firmly contacting chair lumbar support, straighten your back while standing, etc.).

In some embodiments, a level of muscle tension 1541 may be determined based on the employee's body position 1520, including, for example the employee's arm position and shoulder height (e.g., whether the employee's shoulders are raised and the arm is bent in a sub-optimum way), the employee's respiratory rate 1516, and, if multiple health tests have been taken, the length of time the employee' has engaged in physical exertion 1522. For example, it may be determined that the employee is experiencing a high level of muscle tension where the employee's arm is repetitively extended to lift objects. Using these measurements, the system can determine an estimate of the employee's muscle tension 1541 using known techniques.

In some embodiments, a level of eye fatigue 1544 may be determined based on the employee's eye movement 1521. For example, it may be determined that the employee is experiencing a higher level of eye fatigue 1544 where their blink rate has slowed to less than fifteen blinks per minute and/or the employee has been staring at substantially the same position (e.g., the display screen of the mobile device 122) for an extended period (e.g., over twenty minutes).

Although the illustrated embodiment includes exemplary sets of health characteristics 1502 and corresponding health conditions 1504 extrapolated therefrom, it will be appreciated that embodiments may include one or more of the listed health conditions 1504 being provided as health characteristics 1502 or vice versa. For example, where a sensor 102 provides a resting heart rate value, the resting heart rate may be provided as a health characteristic 1502 as opposed to a health condition 1504 extrapolated from the health characteristics 1502. Although the illustrated embodiment includes an exemplary listing of health characteristics/conditions, it will be appreciated that other embodiments may include assessing any variety of health characteristics/conditions that may be of interest to the employee, the employer and/or other users.

The biometric and/or biomechanic health characteristics 1502 and/or health conditions 1504 may be used to identify corresponding health risks 1506. Health risks 1506 may include a third level of health profile data that is derived from one or more of health conditions 1504, health characteristics 1502 and/or collected health data 700. For example, server 604 may process health conditions 1504, health characteristics 1502 and/or collected health data 700 to extrapolate various biometric health risks 1506a and/or biomechanic health risks 1506b for the employee (i.e., risks for developing the associated health condition). Biometric health risks 1506a may include, for example, risk of obesity 1550, risk of injury 1551, risk of diabetes 1552, risk of infection 1553, risk of inflammation 1554, risk of circulation problems 1555, risk of cardiovascular disease 1556, risk of a cardiovascular accidents (e.g., stroke) 1557, risk of illness (e.g., the flu) 1558, risk of developing asthma 1559, risk of developing allergies 1560, risk of developing bronchitis 1561, risk of experiencing depression 1562, and/or the like. Biomechanic health risks 1506b may include, for example, risk of back injury 1563 (e.g., upper/lower back pain), risk of neck injury 1564, risk of musculoskeletal syndrome ("MSD") 1565, risk of carpal tunnel syndrome ("CTS") 1566, risk of epicondylitis (i.e., tennis/golfer's elbow) 1567, risk of a rotator cuff injury 1568, risk of eye disease 1569, risk of physical fatigue, and/or the like.

In some embodiments a health risk may be determined based on one or more heath conditions 1504, health characteristics 1502 and/or other data (e.g., the employee's personal profile). For example, risks of obesity 1550, injury 1551, diabetes 1552, and cardiovascular disease may be based on BMI 1530 and/or body comp 1531. Risk of infection 1553, inflammation 1554, and circulation problems 1555 may be based on body temperature 1510. Risk for cardio vascular disease 1556, cardiovascular accidents 1557, and obesity 1550 may be based on fitness level 1532, blood pressure 1514, and heart rate 1513. Risk for illness 1558, asthma 1559, allergies 1560 and bronchitis 1551 may be based on respiratory rate 1516. Risk of depression 1562 may be based on the employee's emotions 1536 and thoughts 1537. Risk of risk of back injury 1563, neck injury 1564, musculoskeletal syndrome (MSD) 1565, carpal tunnel syndrome (CTS) 1566, epicondylitis 1567, rotator cuff injury 1568, and/or physical fatigue 1570 may be based on the employee's body position 1520, physical exertion 1522, posture 1540, muscle tension 1541, injury 1543, motor functions 1546, and/or the like.

In some embodiments, an employee that is obese (e.g., having a BMI over about 30) may be determined to have a high risk of diabetes 1552 (e.g., 7.37 time greater than normal), a high risk of cardiovascular disease 1556 (e.g., 2.5 time greater than normal), a high risk of cardiovascular disease 1556 (e.g., 2.5 time greater than normal), a high risk of circulation problems 1555 (e.g., 6.38 times greater than normal risk for high blood pressure), a high risk of asthma 1559 (e.g., 2.72 time greater than normal), a high risk of asthma 1559 (e.g., 2.72 time greater than normal) and other conditions, such as 1.88 times greater than normal risk for high cholesterol, 4.41 times greater than normal risk for arthritis, and so forth.

In some embodiments, it may be determined that the employee is at risk of having or already has the flu or other illness if the employee has one or more of a body temperature 1510 over 38° C. (101° F.), a respiratory rate 1533 greater than 20 respirations per minute, and a heart rate 1513 greater than 100 BPM.

In some embodiments, it may be determined that the employee is at risk for inflammation where, for example, the employee's blood pressure 1514 is elevated, the employee's heart rate 1513 is irregular and/or the body temperature 1510 is elevated above normal (e.g., above 37° C. (98.6° F.)).

In some embodiments, it may be determined that the employee is at risk for circulation problems where, for example, the employee has a low body temperature 1510 (e.g., less than 35.5° C. (96° F.) measured at the extremities) or a high respiratory rate 1533 (e.g., greater than 20 respirations per minute).

In some embodiments, it may be determined that an employee is at risk for depression where, for example, the employee's emotions 1536 and/or thoughts 1537 demonstrate a negative pattern. For example, the employee may be determined to be at risk for depression where they have been determined to have an emotion of "unhappy" for greater than 50% of an observed period of at least one week.

In some embodiments, it may be determined that an employee is at risk for physical fatigue where, for example, the employee's motor functions 1546 are below their normal level. For example, the employee may be determined to be at risk for physical fatigue where their motor function 1546 is less than 75% of its normal level for greater than one hour.

In some embodiments, it may be determined that the employee is at risk of a back injury, neck injury, rotator cuff injury, and/or physical fatigue may be based on the employee's high level of physical exertion (e.g., lifting above a predetermined threshold of 25 kg (55 lbs.)) using poor posture/body position (e.g., bending at the back as opposed to the knees).

In some embodiments, some or all of the health characteristics 1502, health conditions 1504, and/or health risks 1506 may be determined/identified using known techniques for extrapolating data. Although the illustrated embodiment includes an exemplary listing of health risks, it will be appreciated that other embodiments may include assessing any variety of health risks that may be of interest to the employee, the employer and/or other users.

In some embodiments, one or more health plans 1508 may be generated based on collected health data 700, health characteristics 1502, health conditions 1504 and/or health risks 1506. Accordingly, health plans 1508 may be based on biometric and/or biomechanic health information collected for the employee. A health plan 1508 may provide a listing of health goals (e.g., lose ten pounds, reduce calorie intake to two-thousand calories per day, etc.), suggested actions for the employee to take to reach the health goals (e.g., an exercise plan, a diet regime, suggestions such as taking breaks from using the computer, breaks from physical activity, etc.) and/or the like. In some embodiments, health plans 1508 includes a preventative health plan to help maintain and improve the employee's health over time. In some embodiments, health plans 1508 include an interactive health plan that can be modified by the employee and/or the employer, and/or that can be used to track the employee's progress relative to the plan goals, and/or the like.

In some embodiments, the health plans 1508 may be determined using a discrete health test, or formulated from a plurality of health tests (e.g., current and historical health information and/or health profile data) to determine the plan based upon a health test trend (e.g., the employee's blood pressure is rising, the employee has gained weight, the employee's BMI is higher, the employee is underweight, the employee's resting heart rate is low or high based upon activity level, etc.). In some embodiments, the health plan is generated by calculating the employee's ideal health characteristics/conditions based on the current health characteristics/conditions/risks. In some embodiments, the difference between the current and ideal health characteristics/conditions/risks is used to identify or generate a corresponding health plan 1508.

Figure 16:
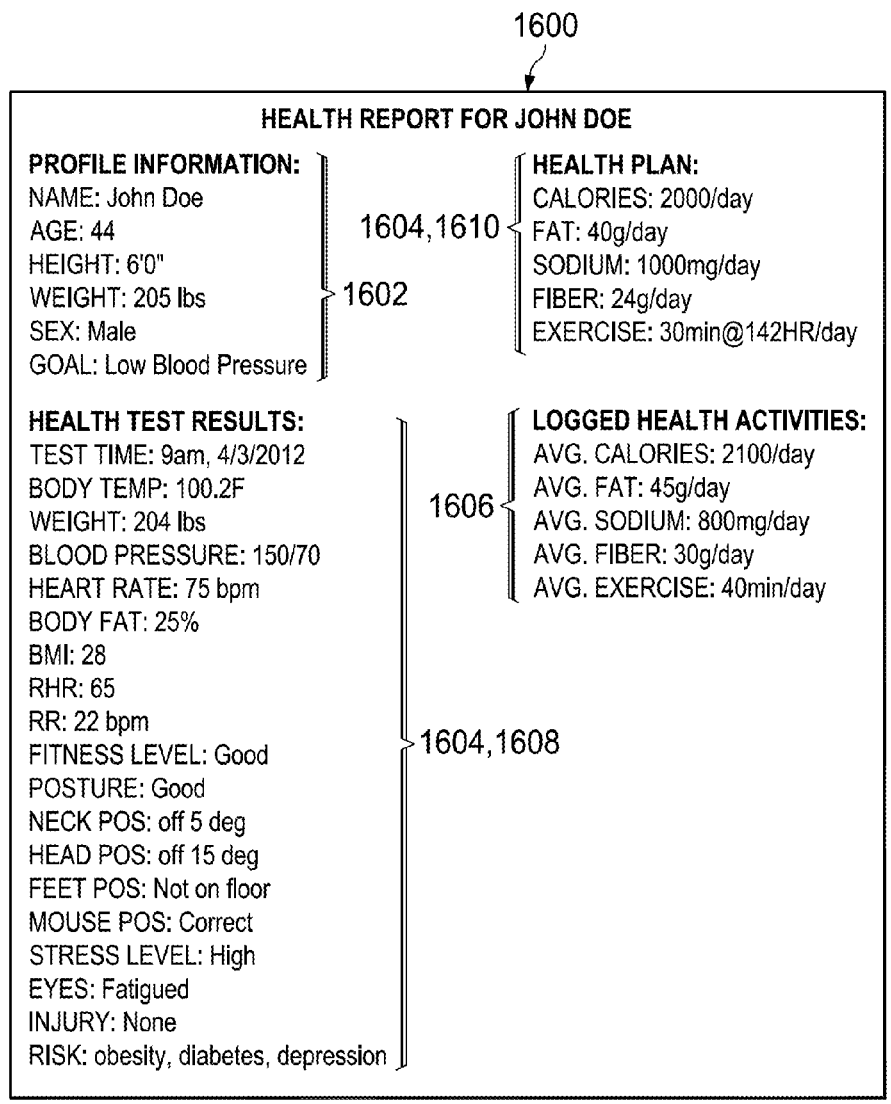
FIG. 16 illustrates an exemplary health report in accordance with one or more embodiments of the present invention.

FIG. 16 illustrates an exemplary health report 1600 in accordance with one or more embodiments of the present invention. Such a health report 1600 may be generated based on health profile 1500 and/or other health information, such as personal profile data for the employee. For example, in the illustrated embodiment, health report 1600 includes personal profile information 1602, health profile information 1604, and logged health activities 1606. The health profile information 1604 including health test result data 1608 (e.g., corresponding to health characteristics 1502, health conditions 1504, and health risk 1506 of health profile 1500) and health plan data 1610 (e.g., corresponding to health plans 1508 of health profile 1500). The logged health activities 1606 may correspond to activity entries by the employee.

Method 1400 may include providing a health report corresponding to the health profile 1406, as depicted at block 906. Providing a health report corresponding to the health profile 1406 may include providing some or all of the employee's health information (e.g., personal information and/or health profile information 1000) for display to the employee, the employer, a medical practitioner, an emergency responder, and/or the like. In some embodiments, the health profile data is provided 1406 via a health report document. For example, server 604 may serve to mobile device 622, employee computer 630 and/or employer workstation 603b for display, a heath report document that is the same or similar to that of the health report 1600 of FIG. 16. Such a report may be rendered by the receiving device for display.

In some embodiments, the health profile 1500 may be communicated via an interactive interface. For example, server 604 may serve, to mobile device 622, employee computer 630 and/or employer workstation 603b, an interactive health dashboard 1512 for communicating/displaying some or all of health profile 1500 to the employee (e.g., via the mobile device 622 and/or employee computer 630) and/or the employer (e.g., via the employer's workstation 103b). In some embodiments, interactive health dashboard 1512 may enable a user (e.g., the employee or employer) to selectively view/edit health information 609 for the employee (e.g., including the personal profile, the health profile, activity data, and/or the like for the employee). For example, an employee may login to the health dashboard 1512 via an application (e.g., a web browser or other network access application) of mobile device 622 and/or computer 630, and interact with dashboard 1512 to update their personal profile data (e.g., name, age, etc.), review their health profile, edit their health plan, enter health activity information (e.g., food they have eaten, exercises they have competed, etc.), initiate health test and so forth.

Providing the health reports 1406 (including health characteristics 1502 and conditions 1504) may help to "inform" the employee regarding their health status. Providing the health reports 1406 (including health risks 1506) may help to "protect" the employee by alerting them to health issues that may need to be addressed. Providing the health report 1406 (including the health plans 1508) may help to "reinforce" the employee by providing a course of action that suggests actions that the employee should take to reduce their risk of developing health problems.

In some embodiments, health information is provided to the employee via an augmented reality display. For example, server 604 may provide functionality similar to that described above with regard to augmented reality processor 104. In some embodiments, server collects health data 700 from health sensors 102, processes the collected health data 700 to generate health information (e.g., including a health profile 1500 for the employee, to identify actions taken by the employee, to predict actions that may be taken by the employee, to identify health consequences of the actions, and/or the like), and serves health content (e.g., health status summaries, health alerts, etc. based on the health information) for display to the employee via augmented reality display device 106.

Figure 17:
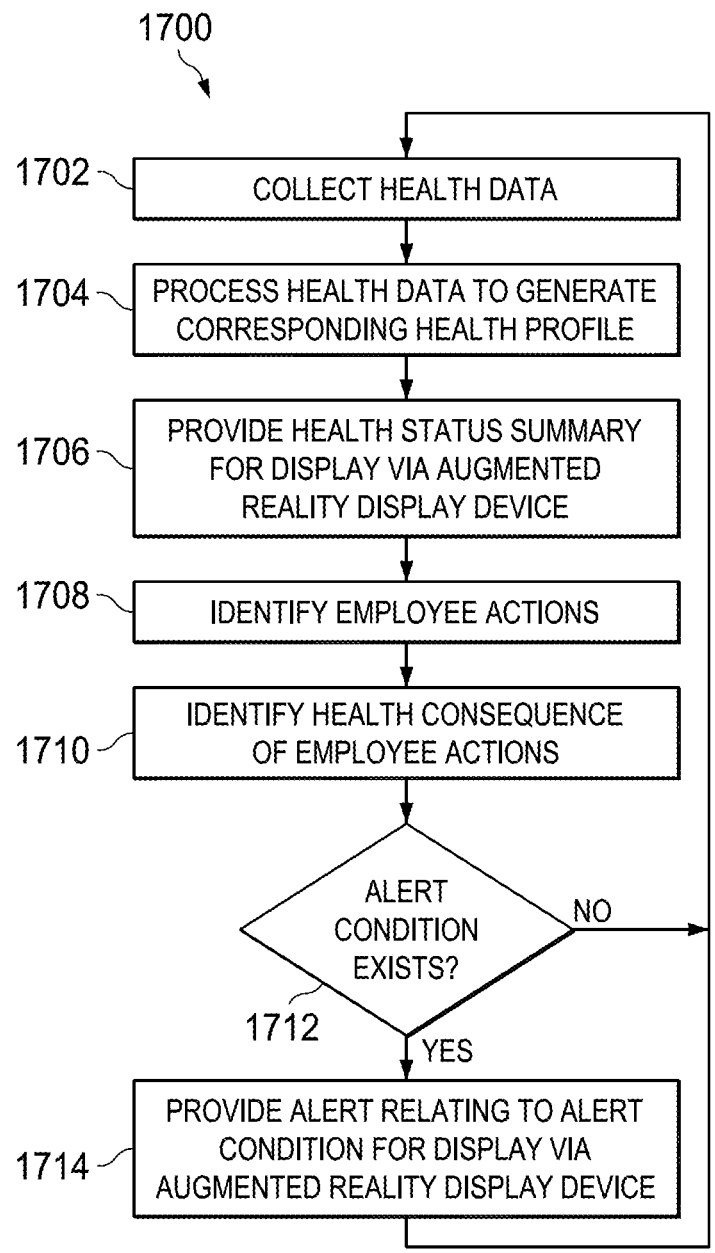
FIG. 17 is a flowchart that illustrates a method for displaying health information via an augmented reality display device in accordance with one or more embodiments of the present invention.

FIG. 17 is a flowchart that illustrates a method 1700 for displaying health information via an augmented reality (AR) display device in accordance with one or more embodiments of the present technique. Method 1700 may include collecting health data, as depicted at block 1702. Collecting health data may be the same or similar to that described with regard to block 1402 of method 1400 (See FIG. 14). For example, collecting health data may include server 604 collecting health data 700 (e.g., temperature data 700a, blood condition data 700b, blood pressure data 700c, force data 700d, body fat data 700e, body position data 700f, audio data 700g, respiration data 700h, neural data 700i and/or heart rate data 700j) for the employee via the various sensors 102 (e.g., via mobile sensors 102a and/or mobile device 622 of the mobile health monitoring system 102 and/or workstation sensors 102b and/or employee computer 630 of workstation 103a).

Method 1700 may include processing health data to generate a corresponding health profile, as depicted at block 1704. Processing health data to generate a corresponding health profile may be the same or similar to that described with regard to block 1404 of method 1400 (See FIG. 14). For example, processing health data to generate a corresponding health profile may include server 604 processing the collected health data 700 to generate a corresponding health profile 1500 including for example, health characteristics, health conditions, health risks, health plans, etc.).

Method 1700 may include providing a health status summary for display via an augmented reality display device, as depicted at block 1706. Providing a health status summary for display via an augmented reality display device may include serving content for display via the augmented reality device that includes a health status summary that includes health information for the employee, such as an indication of some or all of the health characteristics, health conditions and/or health risks for the employee. For example, server 604 may server health content including the employee's current blood pressure (BP), heart rate (HR), and respiratory rate (RR) for display via AR display device 106 (e.g., safety goggles 301, glasses 321, helmet 331 and/or the like worn by the employee) as an overlay in the employee's field of view. For example, AR display device 106 may employ AR projector 402 to project the employee's current blood pressure (BP), heart rate (HR), and respiratory rate (RR) onto an AR display medium 404 (e.g., lenses 302) to provide display of a health status summary that is the same or similar to that of health status summary 206 (See FIG. 2).

In some embodiments, the information provided by the health status summary is based on the most recent health information for the employee. For example, where the employee undergoes a health test to collected health data 700 once per hour, upon receiving the collected health data 700, server 604 may update health profile 1500 based on the most recently collected health data 700, and serve an updated health status summary such that the health status summary 206 overlaid in the employee's field of view is updated at least once per hour to display health information corresponding to the most recently collected health data 700 and/or the data of the current health profile 1500 based on the most recently collected health data 700. As a further example, where the employee undergoes continuous health test (e.g., once per second, once per minute, etc.) to collect continuous stream of health data 700, server 604 may update health profile 1500 based on the most recently collected health data 700, and serve an updated health status summary such that the health status summary 206 overlaid in the employee's field of view is updated continuously to display health information corresponding to the most recently collected health data 700 and/or the data of the current health profile 1500 based on the most recently collected health data 700. Such embodiments may enable the employee to be provided with real-time feedback regarding their current health status/profile.

Method 1700 may include identifying employee actions, as depicted at block 1708. Identifying employee actions may include identifying actions that have already been taken by the employee, that are currently being taken by the employee and/or that are predicted to be taken by the employee. In some embodiments, identifying actions that have already been taken and/or are currently being taken by the employee includes identifying actions that have been taken by the employee based on the collected health data 700, health profile 1500 and/or the like. For example, server 604 may determine that the employee has undertaken or is currently undertaking the action of lifting a heavy object based on the force transducers 1014 located in the employee's work gloves 1008 and/or boots 1016 providing force data 700d and/or a physical exertion 1522 indicative of the employee lifting a heavy object. In some embodiments, identifying predicted actions by the employee is based on the collected health data 700, health profile 1500 and/or the like. For example, server 604 may determine that the employee is about to lift a heavy object based on lifting a heavy object based on neural data 700i and/or thoughts 1537 (e.g., "lift the heavy box") that is indicative of the employee's intention to lift a heavy object. Such embodiments provide an example of actions that may be determined, and it will be appreciated that other embodiments may include identifying any variety of actions in a similar manner.

Method 1700 may include identifying health consequences of the identified employee actions, as depicted at block 1710. Identifying health consequences of the identified employee actions may include identifying health consequences of the actions already taken by the employee, being taken by the employee and/or predicted to be taken by the employee. For example, identifying health consequences of the identified employee actions may include identifying health consequences for lifting a heavy object. In some embodiments, the identified actions may have predefined consequences associated therewith. For example, lifting a heavy object may be associated with a high risk of a lower back injury. As a further example, lifting a light object may be associated with a low risk for a lower back injury or even no health consequence at all.

Method 1700 may include determining whether an alert condition exists, as depicted at block 1712 and, if it is determined that an alert condition does exists, providing a corresponding alert for the alert condition, as depicted at block 1714. Determining whether an alert condition exists may include determining whether the collected health data 700, health profile data (e.g., health characteristics 1502, health conditions 1504 and/or health risks 1506), and/or the actions/consequences rise to the level of providing warranting a health alert to the employee.

In some embodiments, such a determination is made in the course of the health test such that an immediate alert may be provided to the necessary personnel. In some embodiments, determining whether an alert condition exists includes determining whether the collected health data 700 and/or heath profile 1500 is indicative of the employee incurring a health crisis (e.g., a stroke, heart attack, etc.) and, if it determined that the employee is experiencing a health crisis, generating a corresponding alert to be displayed in the employee's field of view via AR display device 106. For example, upon server 605 determining that the employee is experiencing a stroke (e.g., based on health data 700), server 604 may serve, to AR display device 106, health content including a health alert 208 that includes an alert message 209 that states "You may be having a stroke, contact medical personnel immediately" accompanied by an alert icon 210 (e.g., an avatar) providing a graphic/icon indicative of a stroke condition for display in the employee's field of view. In some embodiments, server 604 also generates an automated alert that is transmitted to emergency response personnel, the employer, or the like to notify them of the health crisis.

In some embodiments, determining whether an alert condition exists includes determining whether the collected health data 700 and/or heath profile 1500 is indicative of the employee incurring a serious health risk (e.g., high potential for one of health risk 1006 or the like), and, if it determined that the employee is experiencing a serious health risk, generating a corresponding alert to be displayed in the employee's field of view via AR display device 106. For example, upon server 605 determining that the employee is at risk of developing diabetes (e.g., based on health data 700), server 104 may serve, to AR display device 106, health content including a health alert 208 that includes an alert message 209 that states "You are at risk for developing diabetes" for display to the employee.

In some embodiments, determining whether an alert condition exists includes determining whether a health consequence has been identified, and, if a health consequence has been identified, generating a corresponding alert to be displayed in the employee's field of view via AR display device 106. For example, upon server 604 identifying a health consequence of a high risk for a back injury as a results of the employee's action or predicted action of lifting a heavy object, server 104 may serve, to AR display device 106, health content including a health alert 208 that includes an alert message 209 that states "Do not lift heavy objects. Lifting heavy objects may result in a lower back injury" accompanied by an alert icon 210 (e.g., an avatar) providing a graphic depiction of a lower back injury for display in the employee's field of view (see FIGS. 2, 3A, 3B and 10).

In some embodiments, the determination of whether an employee is experiencing an alert condition is based on comparison of the collected health data 700, health profile data (e.g., health characteristics 1502, health conditions 1504 and/or health risks 1506), and/or the health consequences to predetermined thresholds. For example, as discussed above, it may be determined that the employee is experiencing a serious medical condition where a health characteristic 1502, condition 1504, or health consequence falls outside of a predetermined normal/threshold range (e.g., exceeds a predetermined maximum and/or minimum threshold value) such as a respiration rate 1516 outside of the normal range of 12-120 breaths per minute, blood pressure 1514 outside of the normal range of 90/60-180/120, blood oxygenation level above 90%, a posture 1238 indicative of the employee being slumped over or on the floor). In some embodiments, an abnormal characteristic or condition (i.e., outside of the normal/threshold range) may be compared to other characteristics or conditions to confirm that they are, as a whole, consistent with an emergency actually occurring before proving an alert, thereby reducing the likelihood of a false alert based on an inaccurate measurement (e.g., due to a faulty sensor 120). For example, a health alert may not be provided where the heart rate exceeds an upper limit but the other related characteristics and conditions (e.g., blood pressure and blood oxygenation) remain relatively unchanged (i.e., they are not abnormally elevated or low compared to a baseline).

It will be appreciated that methods 1400 and 1700 are exemplary embodiments of methods that may be employed in accordance with techniques described herein. The methods 1400 and 1700 may be may be modified to facilitate variations of its implementations and uses. The methods 1400 and 1700 may be implemented in software, hardware, or a combination thereof. Some or all of the methods 1400 and 1700 may be implemented by one or more of the modules/applications described herein, such as server module 1310. The order of the methods 1400 and 1700 may be changed, and various elements may be added, reordered, combined, omitted, modified, etc.

In some embodiments, some or all of methods 1400 and 1700 may be executed by the mobile device 622 and/or employee computer 130. For example, mobile device 622 and/or employee computer 130 may collect the health data 700 form sensors 102, process the health data to generate the health profile 1500 (e.g., the health characteristics 1502, conditions 1504, risks 1506 and/or plans 108), identify employee actions and consequences thereof, and/or provide for serving health content including health information 204 (e.g., including health status summaries 206 and/or health alerts 208) to AR display device 106 for display in the employee's field of view. Such an embodiment, including local execution of some or all of the methods by mobile device 622 and/or employee computer 130 that may help to reduce and/or eliminate the processing load on server 604.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification.

As used throughout this application, the word "may" is used in a permissive sense (i.e., meaning having the potential to), rather than the mandatory sense (i.e., meaning must). The words "include", "including", and "includes" mean including, but not limited to. As used throughout this application, the singular forms "a", "an" and "the" include plural referents unless the content clearly indicates otherwise. Thus, for example, reference to "an element" may include a combination of two or more elements. Unless specifically stated otherwise, as apparent from the discussion, it is appreciated that throughout this specification discussions utilizing terms such as "processing", "computing", "calculating", "determining" or the like refer to actions or processes of a specific apparatus, such as a special purpose computer or a similar special purpose electronic processing/computing device. In the context of this specification, a special purpose computer or a similar special purpose electronic processing/computing device is capable of manipulating or transforming signals, typically represented as physical electronic or magnetic quantities within memories, registers, or other information storage devices, transmission devices, or display devices of the special purpose computer or similar special purpose electronic processing/computing device.

The techniques described herein may include or otherwise be used in conjunction with techniques described in U.S. Provisional Patent Application No. 61/664,399 filed on Jun. 26, 2012 and titled "SYSTEMS, COMPUTER MEDIUM AND COMPUTER-IMPLEMENTED METHODS FOR PROVIDING HEALTH INFORMATION TO EMPLOYEES VIA AUGMENTED REALITY DISPLAY", U.S. Provisional Patent Application No. 61/504,638 filed on Jul. 5, 2011 and titled "SYSTEM, COMPUTER PROGRAM PRODUCT AND COMPUTER-IMPLEMENTED METHOD FOR IMPROVING AND MONITORING THE HEALTH AND PRODUCTIVITY OF EMPLOYEES", U.S. Provisional Patent Application No. 61/659,831 filed on Jun. 14, 2012 and titled "SYSTEMS, COMPUTER MEDIUM AND COMPUTER-IMPLEMENTED METHODS FOR MONITORING AND IMPROVING HEALTH AND PRODUCTIVITY OF EMPLOYEES", U.S. Provisional Patent Application No. 61/659,790 filed on Jun. 14, 2012 and titled "SYSTEMS, COMPUTER MEDIUM AND COMPUTER-IMPLEMENTED METHODS FOR MONITORING AND IMPROVING COGNITIVE AND EMOTIVE HEALTH OF EMPLOYEES", U.S. Provisional Patent Application No. 61/659,796 filed on Jun. 14, 2012 and titled "COMPUTER MOUSE SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", U.S. Provisional Patent Application No. 61/659,800 filed on Jun. 14, 2012 and titled "CHAIR PAD SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", U.S. Provisional Patent Application No. 61/659,807 filed on Jun. 14, 2012 and titled "FLOOR MAT SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", U.S. Provisional Patent Application No. 61/659,810 filed on Jun. 14, 2012 and titled "SYSTEMS, COMPUTER MEDIUM AND COMPUTER-IMPLEMENTED METHODS FOR MONITORING AND IMPROVING BIOMETRIC HEALTH OF EMPLOYEES", U.S. Provisional Patent Application No. 61/659,818 filed on Jun. 14, 2012 and titled "SYSTEMS, COMPUTER MEDIUM AND COMPUTER-IMPLEMENTED METHODS FOR MONITORING AND IMPROVING BIOMECHANICAL HEALTH OF EMPLOYEES", U.S. Provisional Patent Application No. 61/659,824 filed on Jun. 14, 2012 and titled "SYSTEMS, COMPUTER MEDIUM AND COMPUTER-IMPLEMENTED METHODS FOR COACHING EMPLOYEES BASED UPON MONITORED HEALTH CONDITIONS USING AN AVATAR", U.S. Provisional Patent Application No. 61/664,387 filed on Jun. 26, 2012 and titled "SYSTEMS, COMPUTER MEDIUM AND COMPUTER-IMPLEMENTED METHODS FOR MONITORING HEALTH OF EMPLOYEES USING MOBILE DEVICES", and U.S. Provisional Patent Application No. 61/664,414 filed on Jun. 26, 2012 and titled "SYSTEMS, COMPUTER MEDIUM AND COMPUTER-IMPLEMENTED METHODS FOR MONITORING HEALTH AND ERGONOMIC STATUS OF DRIVERS OF VEHICLES", the disclosures of which are each hereby incorporated by reference in their entireties.

In this patent, certain U.S. patents, U.S. patent applications, or other materials (e.g., articles) have been incorporated by reference. The text of such U.S. patents, U.S. patent applications, and other materials is, however, only incorporated by reference to the extent that no conflict exists between such material and the statements and drawings set forth herein. In the event of such conflict, any such conflicting text in such incorporated by reference U.S. patents, U.S. patent applications, and other materials is specifically not incorporated by reference in this patent.

What is claimed is:

1. A system for providing real-time feedback of health information to an employee when the employee is engaged in their work duties, the system comprising:
a set of one or more health sensors configured to be provided on or near the employee when the employee is engaged in work duties, the one or more health sensors comprising at least one of biometric sensors configured to sense biometric characteristics of the employee and biomechanic sensors configured to sense biomechanic characteristics of the employee, the one or more health sensors configured to output health data corresponding to at least one of the biometric characteristics and biomechanic characteristics sensed by the set of one or more health sensors;
an augmented reality display device, the augmented reality display device including a head-mounted display (HMD); and
a health server configured to:
receive, via a communications network, the health data output by the set of one or more health sensors;
process the health data received to identify health status information for the employee, the processing comprising:
identifying an action taken by the employee or predicted to be taken by the employee; and
determining an injury that is predicted to occur as a consequence of the action; and
serve, to the augmented reality display device via the communications network, augmented reality content comprising the health status information for the employee, the health status information comprising an indication of the injury that is predicted to occur as a consequence of the action;
the augmented reality display device configured to be worn by the employee when the employee is engaged in work duties and configured to display an augmented reality view visible to the employee when the employee is engaged in work duties, and the augmented reality view comprising a head-up display of the health status information for the employee overlaid on a real world view of an environment surrounding the employee when the employee is engaged in work duties, the health status information comprising computer-generated sensory input representative of real-time health status, and the real world view comprising the employee's line-of-sight view of the employee's surroundings, wherein the augmented reality content comprises an indication of the injury that is predicted to occur as a consequence of the action such that the employee is provided with an augmented reality view comprising the real world view of the surrounding environment having an overlay of the injury that is predicted to occur as a consequence of the action.

2. A system according to claim 1, further comprising a mobile communications device configured to:
collect the health data from the set of one or more health sensors;
forward the health data to the health server;
receive the augmented reality content from the server; and
provide the augmented reality content to the augmented reality display device for display to the employee.

3. A system according to claim 1, wherein the health server is further configured to provide for display of a health report comprising an indication of the injury and one or more suggested actions the employee should take to reduce the employee's risk of developing the injury.

4. A system for providing feedback of health information to an employee when the employee is engaged in their work duties, the system comprising:
a set of one or more health sensors configured to be provided on or near the employee when the employee is engaged in their work duties, the one or more health sensors comprising at least one of biometric sensors configured to sense biometric characteristics of the employee and biomechanic sensors configured to sense biomechanic characteristics of the employee, the one or more health sensors configured to output health data corresponding to at least one of biometric characteristics and biomechanic characteristics sensed by the set of one or more health sensors;
an augmented reality display device; and
an augmented reality processor configured to:
receive the health data output by the one or more health sensors;
process the health data received to identify health status information for the employee, the processing comprising:
determining an action taken by the employee based at least in part on the health data; and
determining a predicted health consequence of the action taken by the employee;
provide, for display via the augmented reality display device, augmented reality content comprising the health status information for the employee, wherein the augmented reality content comprises the predicted health consequence; and
provide for display of a health report comprising the predicted health consequence of the action and one or more suggested actions the employee should take to reduce the employee's risk of developing health problems; and
the augmented reality display device configured to be worn by the employee when the employee is engaged in work duties and configured to display an augmented reality view visible to the employee when the employee is engaged in work duties, and the augmented reality view comprising a head-up display of the health status information for the employee overlaid on a real world view of an environment surrounding the employee when the employee is engaged in work duties, the health status information comprising computer-generated sensory input representative of real-time health status, and the real world view comprising the employee's line-of-sight view of the employee's surroundings such that the employee is provided with an augmented reality view comprising the real world view of the surrounding environment having an overlay of the predicted health consequence of the action taken by the employee.

5. A system according to claim 4, wherein processing the health data received to identify the health status information for the employee comprises processing the health data to determine a health characteristic for the employee, and wherein the augmented reality content comprises the health characteristic for the employee such that the employee is provided with an augmented reality view comprising the real world view of the surrounding environment having an overlay of the health characteristic for the employee.

6. A system according to claim 4, wherein the predicted health consequence comprises a consequence to the employee's physical health or mental health.

7. A system according to claim 4, wherein processing the health data received to identify the health status information for the employee comprises:
processing the health data to predict a second action to be taken by the employee; and
determining a second predicted health consequence of the second action,
wherein the augmented reality content comprises the second predicted health consequence such that the employee is provided with the real world view of the surrounding environment comprising an overlay of the second predicted health consequence based at least in part on the second action predicted to be taken by the employee, wherein the overlay of the second predicted health consequence is configured to be displayed to the employee prior to the employee actually taking the second action.

8. A system according to claim 7, wherein at least one of the health sensors comprises a neural sensor configured to sense brain activity of the employee, the neural sensor including a dry electrode and the brain activity indicative of one or more of alertness, fatigue, and anxiety, and wherein processing the health data to predict the second action to be taken by the employee comprises predicting the second action based at least in part on the brain activity of the employee.

9. A system according to claim 4, wherein the augmented reality display device comprises a head-up display provided in a safety helmet worn by the employee and configured to be viewable by the employee when the employee is engaged in work duties.

10. A system according to claim 4, wherein the augmented reality display comprises a head-up display provided in eyewear worn by the employee and configured to be viewable by the employee when the employee is engaged in work duties.

11. A system according to claim 4, wherein the set of one or more health sensors comprises at least one of a temperature sensor configured to output temperature data indicative of a body temperature of the employee, a blood condition sensor configured to output blood condition data indicative of a blood oxygenation level of the employee, a blood pressure sensor configured to output blood pressure data indicative of a blood pressure of the employee, a body fat sensor configured to output body fat data indicative of a body fat of the employee, a respiration sensor configured to output respiration data indicative of a respiration rate of the employee, a neural sensor configured to output neural data indicative of brain activity of the employee, a force sensor configured to output force data indicative of a body weight of the employee or force exerted by the employee, a position sensor configured to output position data indicative of a body position of the employee, and a camera sensor configured to output image data indicative of at least one of a biometric or biomechanic characteristic of the employee.

12. A method for providing real-time feedback of health information to an employee when the employee is engaged in their work duties, the method comprising:
receiving health data output by a set of one or more health sensors provided on or near the employee when the employee is engaged in work duties, the one or more health sensors comprising at least one of biometric sensors configured to sense biometric characteristics of the employee and biomechanic sensors configured to sense biomechanic characteristics of the employee, the health data corresponding to at least one of biometric characteristics and biomechanic characteristics sensed by the set of one or more health sensors;
processing the health data received to identify health status information for the employee, the processing comprising:
identifying an action taken by the employee based at least in part on the health data; and
determining a predicted health consequence of the action taken by the employee;
providing for display, via augmented reality display device worn by the employee when the employee is engaged in work duties, an augmented reality view comprising a head-up display of the health status information for the employee overlaid on a real world view of an environment surrounding the employee when the employee is engaged in work duties, the health status information comprising computer-generated sensory input representative of real-time health status, and the real world view comprising the employee's line-of-sight view of the employee's surroundings, wherein the augmented reality content comprises the predicted health consequence such that the employee is provided with an augmented reality view comprising the real world view of the surrounding environment having an overlay of the predicted health consequence of the action taken by the employee; and providing for display of a health report comprising the predicted health consequence of the action and one or more suggested actions the employee should take to reduce the employee's risk of developing health problems.

13. A method according to claim 12, wherein processing the health data received to identify the health status information for the employee comprises processing the health data to determine a health characteristic for the employee, and wherein the augmented reality content comprises the health characteristic for the employee such that the employee is provided with an augmented reality view comprising the real world view of the surrounding environment having an overlay of the health characteristic for the employee.

14. A method according to claim 12, wherein the predicted health consequence comprises a consequence to the employee's physical health or mental health.

15. A method according to claim 12, wherein processing the health data received to identify the health status information for the employee comprises:
    processing the health data to predict a second action to be taken by the employee; and
    determining a second predicted health consequence of the second action, and
    wherein the augmented reality content comprises the second predicted health consequence such that the employee is provided with an augmented reality view comprising the real world view of the surrounding environment having an overlay of the second predicted health consequence based at least in part on the second action predicted to be taken by the employee, wherein the overlay of the second predicted health consequence is displayed to the employee prior to the employee actually taking the second action.

16. A method according to claim 15, wherein at least one of the health sensors comprises a neural sensor configured to sense brain activity of the employee, wherein processing the health data to predict the second action to be taken by the employee comprises predicting the second action based at least in part on the brain activity of the employee.

17. A method according to claim 12, wherein the augmented reality display device comprises a head-up display provided in at least one of a safety helmet and eyewear worn by the employee and configured to be viewable by the employee in real time when the employee is engaged in work duties.

18. A method for providing real-time feedback of health information to an employee when the employee is engaged in their work duties, the method comprising:
    receiving health data output by a set of one or more health sensors provided on or near the employee when the employee is engaged in work duties, the one or more health sensors comprising at least one of biometric sensors configured to sense biometric characteristics of the employee and biomechanic sensors configured to sense biomechanic characteristics of the employee, the health data corresponding to at least one of biometric characteristics and biomechanic characteristics sensed by the set of one or more health sensors;
    processing the health data received to identify health status information for the employee, the processing comprising:
        predicting an action to be taken by the employee based at least in part on the health data; and
        determining a predicted health consequence of the action predicted to be taken by the employee; and
    providing for display, via augmented reality display device worn by the employee when the employee is engaged in work duties and prior to the employee actually taking the predicted action, an augmented reality view comprising a head-up display of the health status information for the employee overlaid on a real world view of an environment surrounding the employee when the employee is engaged in work duties, the health status information comprising computer-generated sensory input representative of real-time health status, and the real world view comprising the employee's line-of-sight view of the employee's surroundings, wherein the augmented reality content comprises the predicted health consequence such that the employee is provided with an augmented reality view comprising the real world view of the surrounding environment having an overlay of the predicted health consequence of the action predicted to be taken by the employee prior to the employee actually taking the action; and
    providing for display of a health report comprising the predicted health consequence of the action and one or more suggested actions the employee should take to reduce the employee's risk of developing health problems.

19. A method according to claim 18, wherein the predicted health consequence comprises a predicted physical injury of the employee.

20. A method according to claim 18, wherein at least one of the health sensors comprises a neural sensor configured to sense brain activity of the employee, and wherein predicting an action to be taken by the employee based at least in part on the health data comprises predicting the action based at least in part on the brain activity of the employee.

* * * * *